United States Patent
Andrews et al.

(10) Patent No.: US 10,610,574 B2
(45) Date of Patent: *Apr. 7, 2020

(54) ENHANCING HEALTH IN MAMMALS USING TELOMERASE REVERSE TRANSCRIPTASE GENE THERAPY

(71) Applicant: Sierra Sciences, LLC, Reno, NV (US)

(72) Inventors: William H. Andrews, Reno, NV (US); Lancer K. Brown, Sparks, NV (US); Hamid Mohammadpour, Reno, NV (US); Laura A. Briggs, Reno, NV (US)

(73) Assignee: Sierra Sciences, LLC, Reno, NV (US)

( * ) Notice: Subject to any disclaimer, the term of this patent is extended or adjusted under 35 U.S.C. 154(b) by 0 days.

This patent is subject to a terminal disclaimer.

(21) Appl. No.: 15/220,250

(22) Filed: Jul. 26, 2016

(65) Prior Publication Data
US 2017/0049861 A1 Feb. 23, 2017

Related U.S. Application Data

(63) Continuation of application No. 14/655,140, filed as application No. PCT/US2013/077619 on Dec. 23, 2013, now Pat. No. 9,453,209.

(60) Provisional application No. 61/746,438, filed on Dec. 27, 2012.

(51) Int. Cl.
| | |
|---|---|
| *C07H 21/04* | (2006.01) |
| *A61K 38/45* | (2006.01) |
| *C12N 9/12* | (2006.01) |
| *C12N 7/00* | (2006.01) |
| *A61K 48/00* | (2006.01) |
| *A61K 38/00* | (2006.01) |

(52) U.S. Cl.
CPC .............. *A61K 38/45* (2013.01); *A61K 48/00* (2013.01); *A61K 48/005* (2013.01); *A61K 48/0066* (2013.01); *C12N 7/00* (2013.01); *C12N 9/1276* (2013.01); *C12Y 207/07049* (2013.01); *A61K 38/00* (2013.01); *C12N 2710/10341* (2013.01); *C12N 2740/15041* (2013.01); *C12N 2750/14143* (2013.01)

(58) Field of Classification Search
None
See application file for complete search history.

(56) References Cited

U.S. PATENT DOCUMENTS

| | | | |
|---|---|---|---|
| 6,475,789 B1 | 11/2002 | Cech et al. | |
| 2009/0175892 A1* | 7/2009 | Langlade-Demoyen | .................. A61K 39/0011 424/185.1 |

FOREIGN PATENT DOCUMENTS

| | | |
|---|---|---|
| WO | WO0216555 A2 | 2/2002 |
| WO | WO0216657 A1 | 2/2002 |
| WO | WO0216658 A1 | 2/2002 |
| WO | WO02070668 A2 | 9/2002 |
| WO | WO02072787 A2 | 9/2002 |
| WO | WO02090570 A2 | 11/2002 |
| WO | WO02090571 A2 | 11/2002 |
| WO | WO02101010 A2 | 12/2002 |
| WO | WO03000916 A2 | 1/2003 |
| WO | WO03016474 A2 | 2/2003 |
| WO | WO03034985 A2 | 5/2003 |
| WO | WO2012001170 A1 | 1/2012 |

OTHER PUBLICATIONS

Bachand et al. (RNA 2000, 6:778-784).*
Li et al. (Cold Spring Harbor symposia on quantitative biology. vol. 71. Cold Spring Harbor Laboratory Press, 2006).*
Delluc-Clavières, Aurélie, et al. "Efficient gene transfer in skeletal muscle with AAV-derived bicistronic vector using the FGF-1 IRES." Gene therapy 15.15 (2008): 1090.*
Asokan, Aravind, David V. Schaffer, and R. Jude Samulski. "The AAV vector toolkit: poised at the clinical crossroads." Molecular Therapy 20.4 (2012): 699-708.*
Cristofari et al., Telomere length homeostasis requires that telomerase levels are limiting, The EMBO Journal (2006) 25:565-574.
De Jesus et al., Telomerase gene therapy in adult and old mice delays aging and increases longevity without increasing cancer, EMBO Mol Med (2012) 4(8): 691-704.
Vidale et al., The catalytic and the RNA subunits of human telomerase are required to immortalize equid primary fibroblasts, Chromosoma (2012) 121:475-488.
Sinn et al., Gene therapy progress and prospects: development of improved lentiviral and retroviral vectors—design, biosafety, and production, Gene Ther. Jul. 2005;12(14):1089-98.
Yamaguchi et al., Mutations in TERT, the gene for telomerase reverse transcriptase, in aplastic anemia, N Engl J Med. Apr. 7, 2005;352(14):1413-24.
Harley, Telomerase and cancer therapeutics, Nat Rev Cancer. Mar. 2008;8(3):167-79.

* cited by examiner

*Primary Examiner* — Kimberly Chong
(74) *Attorney, Agent, or Firm* — Tulip Mahaseth; Bret E. Field; Bozicevic, Field & Francis LLP

(57) ABSTRACT

Methods of treating an age-related disorder in a subject are provided. Aspects of the methods include administering to the subject a nucleic acid vector including a coding sequence for telomerase reverse transcriptase (TERT) and/or telomerase RNA (TR). Gene therapy methods are also provided. Aspects of the invention further include compositions, e.g., nucleic acid vectors and kits, etc., that find use in methods of the invention.

14 Claims, 7 Drawing Sheets

Specification includes a Sequence Listing.

SEQUENCE LISTING

<160> NUMBER OF SEQ ID NOS: 3

<210> SEQ ID NO 1
<211> LENGTH: 38420
<212> TYPE: DNA
<213> ORGANISM: Artificial Sequence
<220> FEATURE:
<223> OTHER INFORMATION: Synthetic polynucleotide
<220> FEATURE:
<221> NAME/KEY: misc_feature
<222> LOCATION: (761)..(761)
<223> OTHER INFORMATION: n is a, c, g, or t
<220> FEATURE:
<221> NAME/KEY: misc_feature
<222> LOCATION: (2450)..(2450)
<223> OTHER INFORMATION: n is a, c, g, or t

<400> SEQUENCE: 1

| | | | | | |
|---|---|---|---|---|---|
| tcacagaacc | ctagtattca | acctgccacc | tccctcccaa | cacacagagt | acacagtcct | 60 |
| ttctccccgg | ctggccttaa | aaagcatcat | atcatgggta | acagacatat | tcttaggtgt | 120 |
| tatattccac | acggtttcct | gtcgagccaa | acgctcatca | agtgatatta | ataaactccc | 180 |
| cgggcagctc | acttaagttc | atgtcgctgt | ccagctgctg | agccacaggc | tgctgtccaa | 240 |
| cttgcggttg | cttaacgggc | ggcgaaggag | aagtccacgc | ctacatgggg | ggagagtcat | 300 |
| aatcgtgcat | caggataggg | cggtggtgct | gcagcagcgc | gcgaataaac | tgctgccgcc | 360 |
| gccgctccgt | cctgcaggaa | tacaacatgg | cagtggtctc | ctcagcgatg | attcgcaccg | 420 |
| cccgcagcat | aaggcgcttg | tcctccgggc | acagcagcgc | accctgatct | cacttaaatc | 480 |
| agcacagtaa | ctgcagcaca | gcaccacaat | attgttcaaa | atcccacagt | gcaaggcgct | 540 |
| gtatccaaag | ctcatggcgg | ggaccacaga | acccacgtgg | ccatcatacc | acaagcgcag | 600 |
| gtagattaag | tggcgacccc | tcataaacac | gctggacata | aacattacct | cttttggcat | 660 |
| gttgtaattc | accacctccc | ggtaccatat | aaacctctga | ttaaacatgg | cgccatccac | 720 |
| caccatccta | aaccagctgg | ccaaaacctg | ccccgccggg | ntatacactg | cagggaaccg | 780 |
| ggacttggac | aatgacaagt | gggagagccc | aggactcgta | accatggatc | atcatgctcg | 840 |
| tcatgatatc | aatgttggca | caacacaggc | acacgtgcat | acacttcctc | aggattacaa | 900 |
| gctcctcccg | cgttagaacc | atatcccagg | gaacaaccca | ttcctgaatc | agcgtaaatc | 960 |
| ccacactgca | gggaagacct | cgcacgtaac | tcacgttgtg | cattgtcaaa | gtgttacatt | 1020 |
| cgggcagcag | cggatgatcc | tccagtatgg | tagcgcgggt | ttctgtctca | aaaggaggta | 1080 |
| gacgatccct | actgtacgga | gtgcgccgag | acaaccgaga | tcgtgttggt | cgtagtgtca | 1140 |
| tgccaaatgg | aacgccggac | gtagtcatat | ttcctgaagc | aaaaccaggt | gcgggcgtga | 1200 |
| caaacagatc | tgcgtctccg | gtctcgccgc | ttagatcgct | ctgtgtagta | gttgtagtat | 1260 |
| atccactctc | tcaaagcatc | caggcgcccc | ctggcttcgg | gttctatgta | aactccttca | 1320 |
| tgcgccgctg | ccctgataac | atccaccacc | gcagaataag | ccacacccag | ccaacctaca | 1380 |
| cattcgttct | gcgagtcaca | cacgggagga | gcgggaagag | ctggaagaac | catgtttttt | 1440 |
| tttttattcc | aaaagattat | ccaaaacctc | aaaatgaaga | tctattaagt | gaacgcgctc | 1500 |
| ccctccggtg | gcgtggtcaa | actctacagc | caaagaacag | ataatggcat | ttgtaagatg | 1560 |
| ttgcacaatg | gcttccaaaa | ggcaaacggc | cctcacgtcc | aagtggacgt | aaaggctaaa | 1620 |
| cccttcaggg | tgaatctcct | ctataaacat | tccagcacct | tcaaccatgc | ccaaataatt | 1680 |
| ctcatctcgc | caccttctca | atatatctct | aagcaaatcc | cgaatattta | agtccgggcc | 1740 |
| attgtaaaaa | atttggctcc | agagcgccct | ccaccttcag | cctcaagcag | cgaatcatga | 1800 |

```
ttgcaaaaat tcaggttcct cacagacctg tataagattc aaaagcggaa cattaacaaa    1860
aataccgcga tcccgtaggt cccttcgcag ggccagctga acataatcgt gcaggtctgc    1920
acggaccagc gcggccactt ccccgccagg aaccatgaca aaagaaccca cactgattat    1980
gacacgcata ctcggagcta tgctaaccag cgtagccccg atgtaagctt gttgcatggg    2040
cggcgatata aaatgcaagg tgctgctcaa aaatcaggc aaagcctcgc gcaaaaaga     2100
aagcacatcg tagtcatgct catgcagata aaggcaggta agctccggaa ccaccacaga    2160
aaaagacacc atttttctct caaacatgtc tgcgggtttc tgcataaaca caaaataaaa    2220
taacaaaaaa acatttaaac attagaagcc tgtcttacaa caggaaaaac aacccttata    2280
agcataagac ggactacggc catgccggcg tgaccgtaaa aaaactggtc accgtgatta    2340
aaaagcacca ccgacagctc ctcggtcagt ccggagtcat aatgtaagac tcggtaaaca    2400
catcaggttg attcacatcg gtcagtgtta aaaagcgacc gaaatagccn ggggaatac    2460
aatacccgca ggcgtagaga caacattaca gcccccatag gaggtataac aaaattaata    2520
ggagagaaaa acacataaac acctgaaaaa ccctcctgcc taggcaaaat agcaccctcc    2580
cgctccagaa caacatacag cgcttccaca gcggcagcca taacagtcag ccttaccagt    2640
aaaaagaaa acctattaaa aaaacaccac tcgacacggc accagctcaa tcagtcacag    2700
tgtaaaaaag ggccaagtgc agagcgagta tatataggac taaaaaatga cggtaacggt    2760
taaagtccac aaaaaacacc cagaaaaccg cacgcgaacc tacgcccaga acgaaagcc    2820
aaaaaaccca caacttcctc aaatcgtcac ttccgttttc ccacgttacg tcacttccca    2880
ttttaagaaa actacaattc ccaacacata caagttactc cgccctaaaa cctacgtcac    2940
ccgcccgtt cccacgcccc gcgccacgtc acaaactcca ccccctcatt atcatattgg     3000
cttcaatcca aaataaggta tattattgat gatgttaatt aacatgcatg gatccatatg    3060
cggtgtgaaa taccgcacag atgcgtaagg agaaaatacc gcatcaggcg ctcttccgct    3120
tcctcgctca ctgactcgct gcgctcggtc gttcggctgc ggcgagcggt atcagctcac    3180
tcaaaggcgg taatacggtt atccacagaa tcagggggata acgcaggaaa gaacatgtga    3240
gcaaaaggcc agcaaaaggc caggaaccgt aaaaaggccg cgttgctggc gttttccat    3300
aggctccgcc cccctgacga gcatcacaaa aatcgacgct caagtcagag gtggcgaaac    3360
ccgacaggac tataaagata ccaggcgttt ccccctggaa gctccctcgt gcgctctcct    3420
gttccgaccc tgccgcttac cggatacctg tccgcctttc tcccttcggg aagcgtggcg    3480
ctttctcata gctcacgctg taggtatctc agttcggtgt aggtcgttcg ctccaagctg    3540
ggctgtgtgc acgaaccccc cgttcagccc gaccgctgcg ccttatccgg taactatcgt    3600
cttgagtcca acccggtaag acacgactta tcgccactgg cagcagccac tggtaacagg    3660
attagcagag cgaggtatgt aggcggtgct acagagttct tgaagtggtg gcctaactac    3720
ggctacacta aaggacagt atttggtatc tgcgctctgc tgaagccagt taccttcgga    3780
aaaagagttg gtagctcttg atccggcaaa caaaccaccg ctggtagcgg tggtttttttt    3840
gtttgcaagc agcagattac gcgcagaaaa aaggatctc aagaagatcc tttgatcttt     3900
tctacggggt ctgacgctca gtggaacgaa aactcacgtt aagggatttt ggtcatgaga    3960
ttatcaaaaa ggatcttcac ctagatcctt ttaaattaaa aatgaagttt aaatcaatc     4020
taaagtatat atgagtaaac ttggtctgac agttaccaat gcttaatcag tgaggcacct    4080
atctcagcga tctgtctatt tcgttcatcc atagttgcct gactccccgt cgtgtagata    4140
```

```
actacgatac gggagggctt accatctggc cccagtgctg caatgatacc gcgagaccca    4200
cgctcaccgg ctccagattt atcagcaata aaccagccag ccggaagggc cgagcgcaga    4260
agtggtcctg caactttatc cgcctccatc cagtctatta attgttgccg ggaagctaga    4320
gtaagtagtt cgccagttaa tagtttgcgc aacgttgttg ccattgctgc agccatgaga    4380
ttatcaaaaa ggatcttcac ctagatcctt ttcacgtaga aagccagtcc gcagaaacgg    4440
tgctgacccc ggatgaatgt cagctactgg gctatctgga caagggaaaa cgcaagcgca    4500
aagagaaagc aggtagcttg cagtgggctt acatggcgat agctagactg ggcggtttta    4560
tggacagcaa gcgaaccgga attgccagct ggggcgccct ctggtaaggt tgggaagccc    4620
tgcaaagtaa actggatggc tttcttgccg ccaaggatct gatggcgcag gggatcaagc    4680
tctgatcaag agacaggatg aggatcgttt cgcatgattg aacaagatgg attgcacgca    4740
ggttctccgg ccgcttgggt ggagaggcta ttcggctatg actgggcaca acagacaatc    4800
ggctgctctg atgccgccgt gttccggctg tcagcgcagg ggcgcccggt tctttttgtc    4860
aagaccgacc tgtccggtgc cctgaatgaa ctgcaagacg aggcagcgcg gctatcgtgg    4920
ctggccacga cgggcgttcc ttgcgcagct gtgctcgacg ttgtcactga agcgggaagg    4980
gactggctgc tattgggcga agtgccgggg caggatctcc tgtcatctca ccttgctcct    5040
gccgagaaag tatccatcat ggctgatgca atgcggcggc tgcatacgct tgatccggct    5100
acctgcccat tcgaccacca agcgaaacat cgcatcgagc gagcacgtac tcggatggaa    5160
gccggtcttg tcgatcagga tgatctggac gaagagcatc aggggctcgc gccagccgaa    5220
ctgttcgcca ggctcaaggc gagcatgccc gacggcgagg atctcgtcgt gacccatggc    5280
gatgcctgct tgccgaatat catggtggaa aatggccgct tttctggatt catcgactgt    5340
ggccggctgg gtgtggcgga ccgctatcag gacatagcgt tggctacccg tgatattgct    5400
gaagagcttg gcggcgaatg ggctgaccgc ttcctcgtgc tttacggtat cgccgctccc    5460
gattcgcagc gcatcgcctt ctatcgcctt cttgacgagt tcttctgaat tttgttaaaa    5520
ttttttgttaa atcagctcat tttttaacca ataggccgaa atcggcaaca tcccttataa    5580
atcaaaagaa tagaccgcga tagggttgag tgttgttcca gtttggaaca agagtccact    5640
attaaagaac gtggactcca acgtcaaagg gcgaaaaacc gtctatcagg gcgatggccc    5700
actacgtgaa ccatcaccca aatcaagttt tttgcggtcg aggtgccgta aagctctaaa    5760
tcggaaccct aaagggagcc cccgatttag agcttgacgg ggaaagccgg cgaacgtggc    5820
gagaaaggaa gggaagaaag cgaaaggagc gggcgctagg gcgctggcaa gtgtagcggt    5880
cacgctgcgc gtaaccacca cacccgcgcg cttaatgcgc cgctacaggg cgcgtccatt    5940
cgccattcag gatcgaatta attcttaatt aacatcatca ataatatacc ttattttgga    6000
ttgaagccaa tatgataatg aggggggtgga gtttgtgacg tggcgcgggg cgtgggaacg    6060
gggcgggtga cgtagtagtg tggcggaagt gtgatgttgc aagtgtggcg gaacacatgt    6120
aagcgacgga tgtggcaaaa gtgacgtttt tggtgtgcgc cggtgtacac aggaagtgac    6180
aattttcgcg cggttttagg cggatgttgt agtaaatttg ggcgtaaccg agtaagattt    6240
ggccattttc gcgggaaaac tgaataagag gaagtgaaat ctgaataatt ttgtgttact    6300
catagcgcgt aatactggta ccgcggccgc ctcgagtcta gagatatcga attcaagctt    6360
aaggtgcacg gcccacgtgg ccactagtaa ttttttctgca gaaaacgtac ccggggatcc    6420
tctaggatcc caccgaaagg ttgctcctta acacaggcta aggaccagct tctttgggag    6480
agaacagacg caggggcggg agggaaaaag ggagaggcag acgtcacttc cccttggcgg    6540
```

```
ctctggcagc agattggtcg gttgagtggc agaaaggcag acgggactg  ggcaaggcac    6600
tgtcggtgac atcacggaca gggcgacttc tatgtagatg aggcagcgca gaggctgctg    6660
cttcgccact tgctgcttcg ccacgaagga gttcccgtgc cctgggagcg ggttcaggac    6720
cgcggatcgg aagtgagaat cccagctgtg tgtcagggct ggaaagggct cgggagtgcg    6780
cggggcaagt gaccgtgtgt gtaaagagtg aggcgtatga ggctgtgtcg gggcagagcc    6840
cgaagatccg ggttgcggag ggtgggcctg ggaggggtgg tggccatttt ttgtctaacc    6900
ctaactgaga agggcgtagg cgccgtgctt ttgctccccg cgcgctgttt ttctcgctga    6960
cttttcagcgg gcgaaaaagc ctcggcctgc cgccttccac cgttcattct agagcaaaca    7020
aaaaatgtca gctgctggcc cgttcgcccc tcccggggac ctgcggcggg tcgcctgccc    7080
agcccccgaa ccccgcctgg aggccgcggt cggcccgggg cttctccgga ggcacccact    7140
gccaccgcga agagttgggc tctgtcagcc gcgggtctct cggggggcgag ggcgaggttc    7200
aggcctttca ggccgcagga agaggaacgg agcgagtccc cgcgcgcggc gcgattccct    7260
gagctgtggg acgtgcaccc aggactcggc tcacacatgc agttcgcttt cctgttggtg    7320
gggggaacgc cgatcgtgcg catccgtcac ccctcgccgg caatgggggc ttgtgaaccc    7380
ccaaacctga ctgactgggc cagtgtgctg caaattggca ggagacgtga aggcacctcc    7440
aaagtcgact ttctggagtt tcaaaaacag accgtacgat gcattagtta ttaatagtaa    7500
tcaattacgg ggtcattagt tcatagccca tatatggagt tccgcgttac ataacttacg    7560
gtaaatggcc cgcctggctg accgcccaac gacccccgcc cattgacgtc aataatgacg    7620
tatgttccca tagtaacgcc aatagggact ttccattgac gtcaatgggt ggagtattta    7680
cggtaaactg cccacttggc agtacatcaa gtgtatcata tgccaagtac gccccctatt    7740
gacgtcaatg acggtaaatg gcccgcctgg cattatgccc agtacatgac cttatgggac    7800
tttcctactt ggcagtacat ctacgtatta gtcatcgcta ttaccatggt gatgcggttt    7860
tggcagtaca tcaatgggcg tggatagcgg tttgactcac ggggatttcc aagtctccac    7920
cccattgacg tcaatgggag tttgttttgg caccaaaatc aacgggactt tccaaaatgt    7980
cgtaacaact ccgccccatt gacgcaaatg ggcggtaggc gtgtacggtg ggaggtctat    8040
ataagcagag ctggtttagt gaaccgtcag atccgctagc ccaccatgc  cgcgcgctcc    8100
ccgctgccga ccgtgcgct  ccctgctgcg cagccactac cgcgaggtgc tgccgctggc    8160
cacgttcgtg cggcgcctgg ggccccaggg ctggcggctg gtgcagcgcg ggacccggc    8220
ggctttccgc gcgctggtgg cccagtgcct ggtgtgcgtg ccctgggacg cacggccgcc    8280
ccccgccgcc ccctccttcc gccaggtgtc ctgcctgaag gagctggtgg cccgagtgct    8340
gcagaggctg tgcgagcgcg cgcgaagaa  cgtgctggcc ttcggcttcg cgctgctgga    8400
cggggcccgc gggggccccc ccgaggcctt caccaccagc gtgcgcagct acctgcccaa    8460
cacggtgacc gacgcactgc gggggagcgg ggcgtggggg ctgctgttgc gccgcgtggg    8520
cgacgacgtg ctggttcacc tgctggcacg ctgcgcgctc tttgtgctgg tggctcccag    8580
ctgcgcctac caggtgtgcg ggccgccgct gtaccagctc ggcgctgcca ctcaggcccg    8640
gcccccgcca cacgctagtg accccgaag  gcgtctggga tgcgaacggg cctggaacca    8700
tagcgtcagg gaggccgggg tcccctggg  cctgccagcc ccgggtgcga ggaggcgcgg    8760
gggcagtgcc agccgaagtc tgccgttgcc caagaggccc aggcgtggcg ctgccctga     8820
gccggagcgg acgcccgttg ggcagggtc  ctgggcccac ccgggcagga cgcgtggacc    8880
```

```
gagtgaccgt ggtttctgtg tggtgtcacc tgccagaccc gccgaagaag ccacctcttt     8940
ggagggtgcg ctctctggca cgcgccactc ccacccatcc gtgggccgcc agcaccacgc     9000
gggcccccca tccacatcgc ggccaccacg tccctgggac acgccttgtc ccccggtgta     9060
cgccgagacc aagcacttcc tctactcctc aggcgacaag gagcagctgc ggccctcctt     9120
cctactcagc tctctgaggc ccagcctgac tggcgctcgg aggctcgtgg agaccatctt     9180
tctgggttcc aggccctgga tgccaggggac tccccgcagg ttgccccgcc tgcccccagcg     9240
ctactggcaa atgcggcccc tgtttctgga gctgcttggg aaccacgcgc agtgcccta     9300
cggggtgctc ctcaagacgc actgcccgct gcgagctgcg gtcacccccag cagccggtgt     9360
ctgtgcccgg gagaagcccc agggctctgt ggcggccccc gaggaggagg acacagaccc     9420
ccgtcgcctg gtgcagctgc tccgccagca cagcagcccc tggcaggtgt acggcttcgt     9480
gcgggcctgc ctgcgccggc tggtgccccc aggcctctgg ggctccaggc acaacgaacg     9540
ccgcttcctc aggaacacca agaagttcat ctccctgggg aagcatgcca agctctcgct     9600
gcaggagctg acgtggaaga tgagcgtgcg gggctgcgct tggctgcgca ggagcccagg     9660
ggttggctgt gttccggccg cagagcaccg tctgcgtgag gagatcctgg ccaagttcct     9720
gcactggctg atgagtgtgt acgtcgtcga gctgctcagg tctttctttt atgtcacgga     9780
gaccacgttt caaaagaaca ggctcttttt ctaccggaag agtgtctgga gcaagttgca     9840
aagcattgga atcagacagc acttgaagag ggtgcagctg cgggagctgt cggaagcaga     9900
ggtcaggcag catcgggaag ccaggcccgc cctgctgacg tccagactcc gcttcatccc     9960
caagcctgac gggctgcggc cgattgtgaa catggactac gtcgtgggag ccagaacgtt    10020
ccgcagagaa aagagggccg agcgtctcac ctccagggtg aaggcactgt tcagcgtgct    10080
caactacgag cgggcgcggc gccccggcct cctgggcgcc tctgtgctgg gcctggacga    10140
tatccacagg gcctggcgca ccttcgtgct gcgtgtgcgg gcccaggacc gccgcctga    10200
gctgtacttt gtcaaggtgg atgtgacggg cgcgtacgac accatccccc aggacaggct    10260
cacggaggtc atcgccagca tcatcaaacc ccagaacacg tactgcgtgc gtcggtatgc    10320
cgtggtccag aaggccgccc atgggcacgt ccgcaaggcc ttcaagagcc acgtctctac    10380
cttgacagac ctccagccgt acatgcgaca gttcgtggct cacctgcagg agaccagccc    10440
gctgagggat gccgtcgtca tcgagcagag ctcctccctg aatgaggcca gcagtggcct    10500
cttcgacgtc ttcctacgct tcatgtgcca ccacgccgtg cgcatcaggg gcaagtccta    10560
cgtccagtgc cagggatcc cgcagggctc catcctctcc acgctgctct gcagcctgtg    10620
ctacggcgac atggagaaca agctgtttgc ggggattcgg cgggacgggc tgctcctgcg    10680
tttggtggat gatttcttgt tggtgacacc tcacctcacc cacgcgaaaa ccttcctcag    10740
gaccctggtc cgaggtgtcc ctgagtatgg ctgcgtggtg aacttgcgga agacagtggt    10800
gaacttccct gtagaagacg aggccctggg tggcacggct tttgttcaga tgccggccca    10860
cggcctattc ccctggtgcg gcctgctgct ggatacccgg accctggagg tgcagagcga    10920
ctactccagc tatgcccgga cctccatcag agccagtctc accttcaacc gcggcttcaa    10980
ggctgggagg aacatgcgtc gcaaactctt tgggtcttg cggctgaagt gtcacagcct    11040
gtttctggat ttgcaggtga acagcctcca gacggtgtgc accaacatct acaagatcct    11100
cctgctgcag gcgtacaggt ttcacgcatg tgtgctgcag ctcccatttc atcagcaagt    11160
ttggaagaac cccacatttt tcctgcgcgt catctctgac acggcctccc tctgctactc    11220
catcctgaaa gccaagaacg cagggatgtc gctgggggcc aagggcgccg ccggccctct    11280
```

```
gccctccgag gccgtgcagt ggctgtgcca ccaagcattc ctgctcaagc tgactcgaca   11340
ccgtgtcacc tacgtgccac tcctggggtc actcaggaca gcccagacgc agctgagtcg   11400
gaagctcccg ggacgacgc tgactgccct ggaggccgca gccaacccgg cactgccctc    11460
agacttcaag accatcctgg actgagtcga aactcgcggc cgccatatgc atcctaggcc   11520
tattaatatt ccggagtata cgtagccggc taacgttaac ttgtttattg cagcttataa   11580
tggttacaaa taaagcaata gcatcacaaa tttcacaaat aaagcatttt ttcactgca    11640
ttctagttgt ggtttgtcca aactcatcaa tgtatcttaa cgcggatctg ggcgtggtta   11700
agggtgggaa agaatatata aggtgggggt cttatgtagt tttgtatctg ttttgcagca   11760
gccgccgccg ccatgagcac caactcgttt gatggaagca ttgtgagctc atatttgaca   11820
acgcgcatgc ccccatgggc cggggtgcgt cagaatgtga tgggctccag cattgatggt   11880
cgccccgtcc tgcccgcaaa ctctactacc ttgacctacg agaccgtgtc tggaacgccg   11940
ttggagactg cagcctccgc cgccgcttca gccgctgcag ccaccgcccg cgggattgtg   12000
actgactttg ctttcctgag cccgcttgca agcagtgcag cttcccgttc atccgcccgc   12060
gatgacaagt tgacggctct tttggcacaa ttggattctt tgacccggga acttaatgtc   12120
gtttctcagc agctgttgga tctgcgccag caggtttctg ccctgaaggc ttcctcccct   12180
cccaatgcgg tttaaaacat aaataaaaaa ccagactctg tttggatttg atcaagcaa    12240
gtgtcttgct gtctttattt aggggttttg cgcgcgcggt aggcccggga ccagcggtct   12300
cggtcgttga gggtcctgtg tattttttcc aggacgtggt aaaggtgact ctggatgttc   12360
agatacatgg gcataagccc gtctctgggg tggaggtagc accactgcag agcttcatgc   12420
tgcggggtgg tgttgtagat gatccagtcg tagcaggagc gctgggcgtg gtgcctaaaa   12480
atgtctttca gtagcaagct gattgccagg ggcaggccct tggtgtaagt gtttacaaag   12540
cggttaagct gggatgggtg catacgtggg gatatgagat gcatcttgga ctgtattttt   12600
aggttggcta tgttcccagc catatccctc cggggattca tgttgtgcag aaccaccagc   12660
acagtgtatc cggtgcactt gggaaatttg tcatgtagct tagaaggaaa tgcgtggaag   12720
aacttggaga cgcccttgtg acctccaaga ttttccatgc attcgtccat aatgatggca   12780
atgggcccac gggcggcggc ctgggcgaag atatttctgg gatcactaac gtcatagttg   12840
tgttccagga tgagatcgtc ataggccatt tttacaaagc gcgggcggag ggtgccagac   12900
tgcggtataa tggttccatc cggcccaggg gcgtagttac cctcacagat ttgcatttcc   12960
cacgctttga gttcagatgg ggggatcatg tctacctgcg gggcgatgaa gaaaacggtt   13020
tccggggtag gggagatcag ctgggaagaa agcaggttcc tgagcagctg cgacttaccg   13080
cagccggtgg gcccgtaaat cacacctatt accgggtgca actggtagtt aagagagctg   13140
cagctgccgt catccctgag cagggggggcc acttcgttaa gcatgtccct gactcgcatg   13200
ttttcccctga ccaaatccgc cagaaggcgc tcgccgccca gcgatagcag ttcttgcaag   13260
gaagcaaagt ttttcaacgg tttgagaccg tccgccgtag gcatgctttt gagcgtttga   13320
ccaagcagtt ccaggcggtc ccacagctcg gtcacctgct ctacggcatc tcgatccagc   13380
atatctcctc gtttcgcggg ttggggcggc tttcgctgta cggcagtagt cggtgctcgt   13440
ccagacgggc cagggtcatg tcttttccacg ggcgcagggt cctcgtcagc gtagtctggg   13500
tcacggtgaa ggggtgcgct ccgggctgcg cgctggccag ggtgcgcttg aggtggtcc    13560
tgctggtgct gaagcgctgc cggtcttcgc cctgcgcgtc ggccaggtag catttgacca   13620
```

```
tggtgtcata gtccagcccc tccgcggcgt ggcccttggc gcgcagcttg cccttggagg    13680
aggcgccgca cgaggggcag tgcagacttt tgagggcgta gagcttgggc gcgagaaata    13740
ccgattccgg ggagtaggca tccgcgccgc aggccccgca gacggtctcg cattccacga    13800
gccaggtgag ctctggccgt tcggggtcaa aaaccaggtt tcccccatgc tttttgatgc    13860
gtttcttacc tctggtttcc atgagccggt gtccacgctc ggtgacgaaa aggctgtccg    13920
tgtcccgta tacagacttg agaggcctgt cctcgagcgg tgttccgcgg tcctcctcgt     13980
atagaaactc ggaccactct gagacaaagg ctcgcgtcca ggccagcacg aaggaggcta    14040
agtgggaggg gtagcggtcg ttgtccacta ggggtccac tcgctccagg gtgtgaagac     14100
acatgtcgcc ctcttcggca tcaaggaagg tgattggttt gtaggtgtag gccacgtgac    14160
cgggtgttcc tgaaggggggg ctataaaagg gggtgggggc gcgttcgtcc tcactctctt   14220
ccgcatcgct gtctgcgagg gccagctgtt ggggtgagta ctccctctga aaagcgggca    14280
tgacttctgc gctaagattg tcagtttcca aaaacgagga ggatttgata ttcacctggc    14340
ccgcggtgat gcctttgagg gtggccgcat ccatctggtc agaaaagaca atcttttgt     14400
tgtcaagctt ggtggcaaac gacccgtaga gggcgttgga cagcaacttg gcgatggagc    14460
gcagggtttg gtttttgtcg cgatcggcgc gctccttggc cgcgatgttt agctgcacgt    14520
attcgcgcgc aacgcaccgc cattcgggaa agacggtggt gcgctcgtcg ggcaccaggt    14580
gcacgcgcca accgcggttg tgcagggtga caaggtcaac gctggtggct acctctccgc    14640
gtaggcgctc gttggtccag cagaggcggc cgcccttgcg cgagcagaat ggcggtaggg    14700
ggtctagctg cgtctcgtcc gggggtctg cgtccacggt aaagacccg ggcagcaggc      14760
gcgcgtcgaa gtagtctatc ttgcatcctt gcaagtctag cgcctgctgc catgcgcggg    14820
cggcaagcgc gcgctcgtat gggttgagtg ggggacccca tggcatgggg tgggtgagcg    14880
cggaggcgta catgccgcaa atgtcgtaaa cgtagagggg ctctctgagt attccaagat    14940
atgtagggta gcatcttcca ccgcggatgc tggcgcgcac gtaatcgtat agttcgtgcg    15000
agggagcgag gaggtcggga ccgaggttgc tacgggcggg ctgctctgct cggaagacta    15060
tctgcctgaa gatggcatgt gagttggatg atatggttgg acgctggaag acgttgaagc    15120
tggcgtctgt gagacctacc gcgtcacgca cgaaggaggc gtaggagtcg cgcagcttgt    15180
tgaccagctc ggcggtgacc tgcacgtcta gggcgcagta gtccagggtt tccttgatga    15240
tgtcatactt atcctgtccc tttttttcc acagctcgcg gttgaggaca aactcttcgc     15300
ggtctttcca gtactcttgg atcggaaacc cgtcggcctc cgaacggtaa gagcctagca    15360
tgtagaactg gttgacggcc tggtaggcgc agcatcccTT ttctacgggt agcgcgtatg    15420
cctgcgcggc cttccggagc gaggtgtggg tgagcgcaaa ggtgtccctg accatgactt    15480
tgaggtactg gtatttgaag tcagtgtcgt cgcatccgcc ctgctcccag agcaaaaagt    15540
ccgtgcgctt tttggaacgc ggatttggca gggcgaaggt gacatcgttg aagagtatct    15600
ttcccgcgcg aggcataaag ttgcgtgtga tgcgaaggg tccggcacc tcggaacggt      15660
tgttaattac ctgggcggcg agcacgatct cgtcaaagcc gttgatgttg tggcccacaa    15720
tgtaaagttc caagaagcgc gggatgcccT tgatggaagg caatttttta agttcctcgt    15780
aggtgagctc ttcaggggag ctgagcccgt gctctgaaag ggcccagtct gcaagatgag    15840
ggttggaagc gacgaatgag ctccacaggt cacgggccat tagcatttgc aggtggtcgc    15900
gaaaggtcct aaactggcga cctatggcca ttttttctgg ggtgatgcag tagaaggtaa    15960
gcgggtcttg ttcccagcgg tcccatccaa ggttcgcggc taggtctcgc gcggcagtca    16020
```

```
ctagaggctc atctccgccg aacttcatga ccagcatgaa gggcacgagc tgcttcccaa    16080
aggcccccat ccaagtatag gtctctacat cgtaggtgac aaagagacgc tcggtgcgag    16140
gatgcgagcc gatcgggaag aactggatct cccgccacca attggaggag tggctattga    16200
tgtggtgaaa gtagaagtcc ctgcgacggg ccgaacactc gtgctggctt ttgtaaaaac    16260
gtgcgcagta ctggcagcgg tgcacgggct gtacatcctg cacgaggttg acctgacgac    16320
cgcgcacaag gaagcagagt gggaatttga gcccctcgcc tggcgggttt ggctggtggt    16380
cttctacttc ggctgcttgt ccttgaccgt ctggctgctc gagggagtt acggtggatc     16440 ggaccaccac gccgcgcgag cccaaagtcc agatgtccgc gcgcggcggt cggagcttga    16500
tgacaacatc gcgcagatgg gagctgtcca tggtctggag ctcccgcggc gtcaggtcag    16560
gcgggagctc ctgcaggttt acctcgcata gacgggtcag ggcgcgggct agatccaggt    16620 gataccctaat ttccaggggc tggttggtgg cggcgtcgat ggcttgcaag aggccgcatc   16680
cccgcggcgc gactacggta ccgcgcgcg ggcggtgggc cgcgggggtg tccttggatg     16740
atgcatctaa aagcggtgac gcgggcgagc ccccggaggt agggggggct ccggacccgc    16800
cgggagaggg ggcaggggca cgtcggcgcc gcgcgcgggc aggagctggt gctgcgcgcg    16860
taggttgctg gcgaacgcga cgacgcggcg gttgatctcc tgaatctggc gcctctgcgt    16920
gaagacgacg ggcccggtga gcttgagcct gaaagagagt tcgacagaat caatttcggt    16980
gtcgttgacg gcggcctggc gcaaaatctc ctgcacgtct cctgagttgt cttgataggc    17040
gatctcggcc atgaactgct cgatctcttc ctcctggaga tctccgcgtc cggctcgctc    17100
cacggtggcg gcgaggtcgt tggaaatgcg ggccatgagc tgcgagaagg cgttgaggcc    17160
tccctcgttc cagacgcggc tgtagaccac gccccccttcg gcatcgcggg cgcgcatgac   17220
cacctgcgcg agattgagct ccacgtgccg ggcgaagacg gcgtagtttc gcaggcgctg    17280
aaagaggtag ttgagggtgg tggcggtgtg ttctgccacg aagaagtaca taacccagcg    17340
tcgcaacgtg gattcgttga tatcccccaa ggcctcaagg cgctccatgg cctcgtagaa    17400
gtccacggcg aagttgaaaa actgggagtt gcgcgccgac acggttaact cctcctccag    17460
aagacggatg agctcggcga cagtgtcgcg cacctcgcgc tcaaaggcta cagggcctc    17520 ttcttcttct tcaatctcct cttccataag ggcctcccct tcttcttctt ctggcggcgg    17580
tggggagggg gggacacggc ggcgacgacg gcgcaccggg aggcggtcga caaagcgctc    17640
gatcatctcc ccgcggcgac ggcgcatggt ctcggtgacg gcgcggccgt tctcgcgggg    17700
gcgcagttgg aagacgccgc ccgtcatgtc ccggttatgg gttggcgggg ggctgccatg    17760
cggcagggat acggcgctaa cgatgcatct caacaattgt tgtgtaggta ctccgccgcc    17820
gagggacctg agcgagtccg catcgaccgg atcggaaaac ctctcgagaa aggcgtctaa    17880
ccagtcacag tcgcaaggta ggctgagcac cgtggcgggc ggcagcgggc ggcggtcggg    17940
gttgtttctg gcgcgaggtgc tgctgatgat gtaattaaag taggcggtct tgagacggcg    18000
gatggtcgac agaagcacca tgtccttggg tccggcctgc tgaatgcgca ggcggtcggc    18060
catgccccag gcttcgtttt gacatcggcg caggtctttg tagtagtctt gcatgagcct    18120
ttctaccggc acttcttctt ctccttcctc ttgtcctgca tctcttgcat ctatcgctgc    18180
ggcggcggcg gagtttggcc gtaggtggcg ccctcttcct cccatgcgtg tgaccccgaa    18240
gcccctcatc ggctgaagca gggctaggtc ggcgacaacg cgctcggcta atatggcctg    18300
ctgcacctgc gtgagggtag actggaagtc atccatgtcc acaaagcggt ggtatgcgcc    18360
```

```
cgtgttgatg gtgtaagtgc agttggccat aacggaccag ttaacggtct ggtgacccgg    18420
ctgcgagagc tcggtgtacc tgagacgcga gtaagccctc gagtcaaata cgtagtcgtt    18480
gcaagtccgc accaggtact ggtatcccac caaaaagtgc ggcggcggct ggcggtagag    18540
gggccagcgt agggtggccg gggctccggg ggcgagatct tccaacataa ggcgatgata    18600
tccgtagatg tacctggaca tccaggtgat gccggcggcg gtggtggagg cgcgcggaaa    18660
gtcgcggacg cggttccaga tgttgcgcag cggcaaaaag tgctccatgg tcggacgct    18720 ctggccggtc aggcgcgcgc aatcgttgac gctctaccgt gcaaaggag agcctgtaag    18780 cgggcactct tccgtggtct ggtggataaa ttcgcaaggg tatcatgcg gacgaccggg    18840 gttcgagccc cgtatccggc cgtccgccgt gatccatgcg gttaccgccc gcgtgtcgaa    18900
cccaggtgtg cgacgtcaga aacgggggga gtgctccttt tggcttcctt ccaggcgcgg    18960
cggctgctgc gctagctttt ttggccactg gccgcgcgca gcgtaagcgg ttaggctgga    19020
aagcgaaagc attaagtggc tcgctccctg tagccggagg gttatttcc aagggttgag    19080 tcgcgggacc cccggttcga gtctcggacc ggccggactg cggcgaacgg gggtttgcct    19140
ccccgtcatg caagacccg cttgcaaatt cctccggaaa cagggacgag cccctttttt    19200
gcttttccca gatgcatccg gtgctgcggc agatgcgccc ccctcctcag cagcggcaag    19260
agcaagagca gcggcagaca tgcagggcac cctcccctcc tcctaccgcg tcaggagggg    19320
cgacatccgc ggttgacgcg gcagcagatg gtgattacga acccccgcgg cgccgggccc    19380
ggcactacct ggacttggag gagggcgagg gcctggcgcg gctaggagcg ccctctcctg    19440
agcggtaccc aagggtgcag ctgaagcgtg atacgcgtga ggcgtacgtg ccgcggcaga    19500
acctgtttcg cgaccgcgag ggagaggagc ccgaggagat gcgggatcga aagttccacg    19560
cagggcgcga gctgcggcat ggcctgaatc gcgagcggtt gctgcgcgag gaggactttg    19620
agcccgacgc gcgaaccggg attagtcccg cgcgcgcaca cgtggcggcc gccgacctgg    19680
taaccgcata cgagcagacg gtgaaccagg agattaactt tcaaaaaagc tttaacaacc    19740
acgtgcgtac gcttgtggcg cgcgaggagg tggctatagg actgatgcat ctgtgggact    19800
ttgtaagcgc gctggagcaa aacccaaata gcaagccgct catggcgcag ctgttcctta    19860
tagtgcagca cagcagggac aacgaggcat tcagggatgc gctgctaaac atagtagagc    19920
ccgagggccg ctggctgctc gatttgataa acatcctgca gagcatagtg gtgcaggagc    19980
gcagcttgag cctggctgac aaggtggccg ccatcaacta ttccatgctt agcctgggca    20040
agttttacgc ccgcaagata taccataccc cttacgttcc catagacaag gaggtaaaga    20100
tcgaggggtt ctacatgcgc atggcgctga aggtgcttac cttgagcgac gacctgggcg    20160
tttatcgcaa cgagcgcatc cacaaggccg tgagcgtgag ccggcggcgc gagctcagcg    20220
accgcgagct gatgcacagc ctgcaaaggg ccctggctgg cacgggcagc ggcgatagag    20280
aggccgagtc ctactttgac gcgggcgctg acctgcgctg gccccaagc cgacgcgccc    20340 tggaggcagc tggggccgga cctggctgg cgtggcacc cgcgcgcgct ggcaacgtcg    20400
gcggcgtgga ggaatatgac gaggacgatg agtacgagcc agaggacggc gagtactaag    20460
cggtgatgtt tctgatcaga tgatgcaaga cgcaacggac ccggcggtgc gggcggcgct    20520
gcagagccag ccgtccggcc ttaactccac ggacgactgg cgccaggtca tggaccgcat    20580
catgtcgctg actgcgcgca atcctgacgc gttccggcag cagccgcagg ccaaccggct    20640
ctccgcaatt ctggaagcgg tggtcccggc gcgcgcaaac cccacgcacg agaaggtgct    20700
ggcgatcgta aacgcgctgg ccgaaaacag ggccatccgg cccgacgagg ccggcctggt    20760
```

```
ctacgacgcg ctgcttcagc gcgtggctcg ttacaacagc ggcaacgtgc agaccaacct    20820
ggaccggctg gtgggggatg tgcgcgaggc cgtggcgcag cgtgagcgcg cgcagcagca    20880
gggcaacctg ggctccatgg ttgcactaaa cgccttcctg agtacacagc ccgccaacgt    20940
gccgcgggga caggaggact acaccaactt tgtgagcgca ctgcggctaa tggtgactga    21000
gacaccgcaa agtgaggtgt accagtctgg gccagactat ttttccaga ccagtagaca    21060 aggcctgcag accgtaaacc tgagccaggc tttcaaaaac ttgcaggggc gtgggggggt    21120
gcgggctccc acaggcgacc gcgcgaccgt gtctagcttg ctgacgccca actcgcgcct    21180
gttgctgctg ctaatagcgc ccttcacgga cagtggcagc gtgtcccggg acacatacct    21240
aggtcacttg ctgacactgt accgcgaggc cataggtcag gcgcatgtgg acgagcatac    21300
tttccaggag attacaagtg tcagccgcgc gctggggcag gaggacacgg gcagcctgga    21360
ggcaacccta aactacctgc tgaccaaccg gcggcagaag atccctcgt tgcacagttt    21420 aaacagcgag gaggagcgca ttttgcgcta cgtgcagcag agcgtgagcc ttaacctgat    21480
gcgcgacggg gtaacgccca gcgtggcgct ggacatgacc gcgcgcaaca tggaaccggg    21540
catgtatgcc tcaaaccggc cgtttatcaa ccgcctaatg gactacttgc atcgcgcggc    21600
cgccgtgaac cccgagtatt tcaccaatgc catcttgaac ccgcactggc taccgccccc    21660
tggtttctac accgggggat tcgaggtgcc cgagggtaac gatggattcc tctgggacga    21720
catagacgac agcgtgtttt ccccgcaacc gcagaccctg ctagagttgc aacagcgcga    21780
gcaggcagag gcggcgctgc gaaaggaaag cttccgcagg ccaagcagct tgtccgatct    21840
aggcgctgcg gccccgcggt cagatgctag tagcccattt ccaagcttga tagggtctct    21900
taccagcact cgcaccaccc gcccgcgcct gctgggcgag gaggagtacc taaacaactc    21960
gctgctgcag ccgcagcgcg aaaaaaacct gcctccggca tttcccaaca acgggataga    22020
gagcctagtg gacaagatga gtagatggaa gacgtacgcg caggagcaca gggacgtgcc    22080
aggcccgcgc ccgcccaccc gtcgtcaaag gcacgaccgt cagcggggtc tggtgtggga    22140
ggacgatgac tcggcagacg acagcagcgt cctggatttg ggagggagtg gcaacccgtt    22200
tgcgcacctt cgccccaggc tggggagaat gttttaaaaa aaaaaagca tgatgcaaaa    22260 taaaaaactc accaaggcca tggcaccgag cgttggtttt cttgtattcc ccttagtatg    22320
cggcgcgcgg cgatgtatga ggaaggtcct cctccctcct acgagagtgt ggtgagcgcg    22380
gcgccagtgg cggcggcgct gggttctccc ttcgatgctc ccctggaccc gccgtttgtg    22440
cctccgcggt acctgcggcc taccgggggg agaaacagca tccgttactc tgagttggca    22500
cccctattcg acaccacccg tgtgtacctg gtggacaaca agtcaacgga tgtggcatcc    22560
ctgaactacc agaacgacca cagcaacttt ctgaccacgg tcattcaaaa caatgactac    22620
agcccggggg aggcaagcac acagaccatc aatcttgacg accggtcgca ctgggcggc    22680 gacctgaaaa ccatcctgca taccaacatg ccaaatgtga acgagttcat gtttaccaat    22740
aagtttaagg cgcgggtgat ggtgtcgcgc ttgcctacta aggacaatca ggtggagctg    22800
aaatacgagt gggtggagtt cacgctgccc gagggcaact actccgagac catgaccata    22860
gaccttatga acaacgcgat cgtggagcac tacttgaaag tgggcagaca gaacgggtt    22920 ctggaaagcg acatcggggt aaagtttgac acccgcaact tcagactggg gtttgacccc    22980
gtcactggtc ttgtcatgcc tgggtatat acaaacgaag ccttccatcc agacatcatt    23040
ttgctgccag gatgcgggt ggacttcacc cacagccgcc tgagcaactt gttgggcatc    23100
```

```
cgcaagcggc aacccttcca ggagggcttt aggatcacct acgatgatct ggagggtggt   23160
aacattcccg cactgttgga tgtggacgcc taccaggcga gcttgaaaga tgacaccgaa   23220
cagggcgggg gtggcgcagg cggcagcaac agcagtggca gcggcgcgga agagaactcc   23280
aacgcggcag ccgcggcaat gcagccggtg gaggacatga acgatcatgc cattcgcggc   23340
gacacctttg ccacacgggc tgaggagaag cgcgctgagg ccgaagcagc ggccgaagct   23400 gccgccccg ctgcgcaacc cgaggtcgag aagcctcaga agaaaccggt gatcaaaccc   23460
ctgacagagg acagcaagaa acgcagttac aacctaataa gcaatgacag caccttcacc   23520
cagtaccgca gctggtacct tgcatacaac tacggcgacc ctcagaccgg aatccgctca   23580
tggaccctgc tttgcactcc tgacgtaacc tgcggctcgg agcaggtcta ctggtcgttg   23640
ccagacatga tgcaagaccc cgtgaccttc cgctccacgc gccagatcag caactttccg   23700
gtggtgggcg ccgagctgtt gcccgtgcac tccaagagct tctacaacga ccaggccgtc   23760
tactcccaac tcatccgcca gtttacctct ctgacccacg tgttcaatcg ctttcccgag   23820
aaccagattt tggcgcgccc gccagccccc accatcacca ccgtcagtga aaacgttcct   23880
gctctcacag atcacgggac gctaccgctg cgcaacagca tcggaggagt ccagcgagtg   23940
accattactg acgccagacg ccgcacctgc ccctacgttt acaaggccct gggcatagtc   24000
tcgccgcgcg tcctatcgag ccgcactttt tgagcaagca tgtccatcct tatatcgccc   24060
agcaataaca caggctgggg cctgcgcttc caagcaaga tgtttggcgg ggccaagaag   24120
cgctccgacc aacacccagt gcgcgtgcgc gggcactacc gcgcgccctg gggcgcgcac   24180
aaacgcggcc gcactgggcg caccaccgtc gatgacgcca tcgacgcggt ggtggaggag   24240
gcgcgcaact acacgcccac gccgccacca gtgtccacag tggacgcggc cattcagacc   24300
gtggtgcgcg gagcccggcg ctatgctaaa atgaagagac ggcggaggcg cgtagcacgt   24360
cgccaccgcc gccgacccgg cactgccgcc caacgcgcgg cggcggcccct gcttaaccgc   24420 gcacgtcgca ccgccgacg ggcggccatg cgggccgctc gaaggctggc cgcgggtatt   24480
gtcactgtgc cccccaggtc caggcgacga gcggccgccg cagcagccgc ggccattagt   24540
gctatgactc agggtcgcag gggcaacgtg tattgggtgc gcgactcggt tagcggcctg   24600
cgcgtgcccg tgcgcacccg ccccccgcgc aactagattg caagaaaaaa ctacttagac   24660
tcgtactgtt gtatgtatcc agcggcggcg gcgcgcaacg aagctatgtc caagcgcaaa   24720
atcaaagaag agatgctcca ggtcatcgcg ccggagatct atggcccccc gaagaaggaa   24780
gagcaggatt acaagcccg aaagctaaag cgggtcaaaa agaaaaagaa agatgatgat   24840
gatgaacttg acgacgaggt ggaactgctg cacgctaccg cgcccaggcg acgggtacag   24900
tggaaaggtc gacgcgtaaa acgtgttttg cgacccggca ccaccgtagt ctttacgccc   24960
ggtgagcgct ccacccgcac ctacaagcgc gtgtatgatg aggtgtacgg cgacgaggac   25020
ctgcttgagc aggccaacga gcgcctcggg gagtttgcct acggaaagcg gcataaggac   25080
atgctggcgt tgccgctgga cgagggcaac ccaacaccta gcctaaagcc cgtaacactg   25140
cagcaggtgc tgcccgcgct tgcaccgtcc gaagaaaagc gcggcctaaa gcgcgagtct   25200
ggtgacttgg cacccaccgt gcagctgatg gtacccaagc gccagcgact ggaagatgtc   25260
ttggaaaaaa tgaccgtgga acctgggctg gagcccgagg tccgcgtgcg gccaatcaag   25320
caggtggcgc cggactggg cgtgcagacc gtggacgttc agatacccac taccagtagc   25380
accagtattg ccaccgccac agagggcatg gagacacaaa cgtccccggt tgcctcagcg   25440
gtggcggatg ccgcggtgca ggcggtcgct gcggccgcgt ccaagacctc tacggaggtg   25500
```

```
caaacggacc cgtggatgtt tcgcgtttca gcccccggc gcccgcgcgg ttcgaggaag   25560 tacgcgccg ccagcgcgct actgcccgaa tatgccctac atccttccat tgcgcctacc    25620
cccggctatc gtggctacac ctaccgcccc agaagacgag caactacccg acgccgaacc   25680
accactggaa cccgccgccg ccgtcgccgt cgccagcccg tgctggcccc gatttccgtg    25740
cgcagggtgg ctcgcgaagg aggcaggacc ctggtgctgc aacagcgcg ctaccacccc    25800 agcatcgttt aaaagccggt ctttgtggtt cttgcagata tggccctcac ctgccgcctc   25860
cgtttcccgg tgccgggatt ccgaggaaga atgcaccgta ggaggggcat ggccggccac    25920
ggcctgacgg gcggcatgcg tcgtgcgcac caccggcggc ggcgcgcgtc gcaccgtcgc   25980
atgcgcggcg gtatcctgcc cctccttatt ccactgatcg ccgcggcgat tggcgccgtg   26040
cccggaattg catccgtggc cttgcaggcg cagagacact gattaaaaac aagttgcatg    26100
tggaaaaatc aaaataaaaa gtctggactc tcacgctcgc ttggtcctgt aactattttg    26160
tagaatggaa gacatcaact ttgcgtctct ggccccgcga cacggctcgc gcccgttcat   26220
gggaaactgg caagatatcg gcaccagcaa tatgagcggt ggcgccttca gctggggctc   26280
gctgtggagc ggcattaaaa atttcggttc caccgttaag aactatggca gcaaggcctg    26340
gaacagcagc acaggccaga tgctgaggga taagttgaaa gagcaaaatt ccaacaaaa    26400 ggtggtagat ggcctggcct ctggcattag cggggtggtg gacctggcca accaggcagt   26460 gcaaataag attaacagta agcttgatcc ccgccctccc gtagaggagc ctccaccggc    26520
cgtggagaca gtgtctccag aggggcgtgg cgaaaagcgt ccgcgcccg acagggaaga    26580 aactctggtg acgcaaatag acgagcctcc ctcgtacgag gaggcactaa agcaaggcct   26640
gcccaccacc cgtcccatcg cgcccatggc taccggagtg ctgggccagc acacaccgt    26700 aacgctggac ctgcctcccc ccgccgacac ccagcagaaa cctgtgctgc caggcccgac    26760
cgccgttgtt gtaacccgtc ctagccgcgc gtccctgcgc cgcgccgcca gcggtccgcg   26820
atcgttgcgg cccgtagcca gtggcaactg gcaaagcaca ctgaacagca tcgtgggtct   26880
gggggtgcaa tccctgaagc gccgacgatg cttctgaata gctaacgtgt cgtatgtgtg   26940
tcatgtatgc gtccatgtcg ccgccagagg agctgctgag ccgccgcgcg cccgctttcc   27000
aagatggcta cccctttcgat gatgccgcag tggtcttaca tgcacatctc gggccaggac   27060
gcctcggagt acctgagccc cgggctggtg cagtttgccc gcgccaccga gacgtacttc    27120
agcctgaata acaagtttag aaaccccacg gtggcgccta cgcacgacgt gaccacagac   27180
cggtcccagc gtttgacgct gcggttcatc cctgtggacc gtgaggatac tgcgtactcg   27240
tacaaggcgc ggttcaccct agctgtgggt gataaccgtg tgctggacat ggcttccacg   27300
tactttgaca tccgcggcgt gctggacagg ggccctactt ttaagcccta ctctggcact   27360
gcctacaacg ccctggctcc caagggtgcc ccaaatcctt gcgaatggga tgaagctgct   27420
actgctcttg aaataaaacct agaagaagag gacgatgaca acgaagacga agtagacgag    27480
caagctgagc agcaaaaaac tcacgtattt gggcaggcgc cttattctgg tataaatatt   27540
acaaaggagg gtattcaaat aggtgtcgaa ggtcaaacac ctaaatatgc cgataaaaca    27600
tttcaacctg aacctcaaat aggagaatct cagtggtacg aaactgaaat taatcatgca   27660
gctgggagag tccttaaaaa gactaccccca atgaaaccat gttacggttc atatgcaaaa   27720
cccacaaatg aaaatggagg gcaaggcatt cttgtaaagc aacaaaatgg aaagctagaa   27780
agtcaagtgg aaatgcaatt tttctcaact actgaggcga ccgcaggcaa tggtgataac   27840
```

```
ttgactccta aagtggtatt gtacagtgaa gatgtagata tagaaacccc agacactcat    27900
atttcttaca tgcccactat taaggaaggt aactcacgag aactaatggg ccaacaatct    27960
atgcccaaca ggcctaatta cattgctttt agggacaatt ttattggtct aatgtattac    28020
aacagcacgg gtaatatggg tgttctggcg ggccaagcat cgcagttgaa tgctgttgta    28080
gatttgcaag acagaaacac agagctttca taccagcttt tgcttgattc cattggtgat    28140
agaaccaggt acttttctat gtggaatcag gctgttgaca gctatgatcc agatgttaga    28200
attattgaaa atcatggaac tgaagatgaa cttccaaatt actgctttcc actgggaggt    28260
gtgattaata cagagactct taccaaggta aaacctaaaa caggtcagga aaatggatgg    28320 gaaaagatg ctacagaatt ttcagataaa aatgaaataa gagttggaaa taattttgcc    28380
atggaaatca atctaaatgc caacctgtgg agaaatttcc tgtactccaa catagcgctg    28440
tatttgcccg acaagctaaa gtacagtcct tccaacgtaa aaatttctga taacccaaac    28500
acctacgact acatgaacaa gcgagtggtg gctcccgggt tagtggactg ctacattaac    28560
cttggagcac gctggtccct tgactatatg gacaacgtca acccatttaa ccaccaccgc    28620
aatgctggcc tgcgctaccg ctcaatgttg ctgggcaatg gtcgctatgt gcccttccac    28680
atccaggtgc ctcagaagtt cttttgccatt aaaaaacctcc ttctcctgcc gggctcatac    28740
acctacgagt ggaacttcag gaaggatgtt aacatggttc tgcagagctc cctaggaaat    28800
gacctaaggg ttgacggagc cagcattaag tttgatagca tttgccttta cgccaccttc    28860
ttccccatgg cccacaacac cgcctccacg cttgaggcca tgcttagaaa cgacaccaac    28920
gaccagtcct ttaacgacta tctctccgcc gccaacatgc tctaccctat acccgccaac    28980
gctaccaacg tgcccatatc catcccctcc cgcaactggg cggctttccg cggctgggcc    29040
ttcacgcgcc ttaagactaa ggaaacccca tcactgggct cgggctacga cccttattac    29100
acctactctg gctctatacc ctacctagat ggaacctttt acctcaacca cacctttaag    29160
aaggtggcca ttacctttga ctcttctgtc agctggcctg gcaatgaccg cctgcttacc    29220
cccaacgagt ttgaaattaa gcgctcagtt gacggggagg gttacaacgt tgcccagtgt    29280
aacatgacca aagactggtt cctggtacaa atgctagcta actacaacat tggctaccag    29340
ggcttctata tcccagagag ctacaaggac cgcatgtact ccttctttag aaacttccag    29400
cccatgagcc gtcaggtggt ggatgatact aaatacaagg actaccaaca ggtgggcatc    29460
ctacaccaac acaacaactc tggatttgtt ggctaccttg cccccaccat gcgcgaagga    29520
caggcctacc ctgctaactt ccccctatccg cttataggca agaccgcagt tgacagcatt    29580
acccagaaaa agtttctttg cgatcgcacc ctttggcgca tcccattctc cagtaacttt    29640
atgtccatgg gcgcactcac agacctgggc caaaaccttc tctacgccaa ctccgcccac    29700
gcgctagaca tgactttga ggtggatccc atggacgagc ccaccttct ttatgttttg    29760 tttgaagtct ttgacgtggt ccgtgtgcac cggccgcacc gcggcgtcat cgaaaccgtg    29820
tacctgcgca cgcccttctc ggccggcaac gccacaacat aaagaagcaa gcaacatcaa    29880
caacagctgc cgccatgggc tccagtgagc aggaactgaa agccattgtc aaagatcttg    29940
gttgtgggcc atatttttg ggcacctatg acaagcgctt ccaggctttt gtttctccac    30000
acaagctcgc ctgcgccata gtcaatacgg ccggtcgcga gactggggc gtacactgga    30060 tggccttttgc ctggaacccg cactcaaaaa catgctacct ctttgagccc tttggctttt    30120
ctgaccagcg actcaagcag gtttaccagt ttgagtacga gtcactcctg cgccgtagcc    30180
ccattgcttc ttccccgac cgctgtataa cgctggaaaa gtccacccaa agcgtacagg    30240
```

```
ggcccaactc ggccgcctgt ggactattct gctgcatgtt tctccacgcc tttgccaact   30300
ggccccaaac tcccatggat cacaacccca ccatgaacct tattaccggg gtacccaact   30360
ccatgctcaa cagtccccag gtacagccca ccctgcgtcg caaccaggaa cagctctaca   30420
gcttcctgga gcgccactcg ccctacttcc gcagccacag tgcgcagatt aggagcgcca   30480 cttcttttg tcacttgaaa aacatgtaaa aataatgtac tagagacact ttcaataaag   30540
gcaaatgctt ttatttgtac actctcgggt gattatttac ccccaccctt gccgtctgcg   30600
ccgtttaaaa atcaaagggg ttctgccgcg catcgctatg cgccactggc agggacacgt   30660
tgcgatactg gtgtttagtg ctccacttaa actcaggcac aaccatccgc ggcagctcgg   30720
tgaagttttc actccacagg ctgcgcacca tcaccaacgc gtttagcagg tcgggcgccg   30780
atatcttgaa gtcgcagttg gggcctccgc cctgcgcgcg cgagttgcga tacacagggt   30840
tgcagcactg gaacactatc agcgccgggt ggtgcacgct ggccagcacg ctcttgtcgg   30900
agatcagatc cgcgtccagg tcctccgcgt tgctcagggc gaacggagtc aactttggta   30960
gctgccttcc caaaagggc gcgtgcccag gctttgagtt gcactcgcac cgtagtggca   31020
tcaaaaggtg accgtgcccg gtctgggcgt taggatacag cgcctgcata aaagccttga   31080
tctgcttaaa agccacctga gcctttgcgc cttcagagaa gaacatgccg caagacttgc   31140
cggaaaactg attggccgga caggccgcgt cgtgcacgca gcaccttgcg tcggtgttgg   31200
agatctgcac cacatttcgg ccccaccggt tcttcacgat cttggccttg ctagactgct   31260
ccttcagcgc gcgctgcccg ttttcgctcg tcacatccat ttcaatcacg tgctccttat   31320
ttatcataat gcttccgtgt agacacttaa gctcgccttc gatctcagcg cagcggtgca   31380
gccacaacgc gcagcccgtg ggctcgtgat gcttgtaggt cacctctgca aacgactgca   31440
ggtacgcctg caggaatcgc cccatcatcg tcacaaaggt cttgttgctg gtgaaggtca   31500
gctgcaaccc gcggtgctcc tcgttcagcc aggtcttgca tacggccgcc agagcttcca   31560
cttggtcagg cagtagtttg aagttcgcct ttagatcgtt atccacgtgg tacttgtcca   31620
tcagcgcgcg cgcagcctcc atgcccttct cccacgcaga cacgatcggc acactcagcg   31680
ggttcatcac cgtaatttca ctttccgctt cgctgggctc ttcctcttcc tcttgcgtcc   31740
gcataccacg cgccactggg tcgtcttcat tcagccgccg cactgtgcgc ttacctcctt   31800
tgccatgctt gattagcacc ggtgggttgc tgaaacccac catttgtagc gccacatctt   31860
ctctttcttc ctcgctgtcc acgattacct ctggtgatgg cgggcgctcg ggcttgggag   31920
aagggcgctt cttttctcc ttgggcgcaa tggccaaatc cgccgccgag gtcgatggcc   31980
gcgggctggg tgtgcgcggc accagcgcgt cttgtgatga gtcttcctcg tcctcggact   32040
cgatacgccg cctcatccgc tttttggg gcgcccgggg aggcggcggc gacgggacg   32100 gggacgacac gtcctccatg gttggggac gtcgcgccgc accgcgtccg cgctcggggg   32160
tggtttcgcg ctgctcctct tcccgactgg ccatttcctt ctcctatagg cagaaaaaga   32220
tcatggagtc agtcgagaag aaggacagcc taaccgcccc ctctgagttc gccaccaccg   32280
cctccaccga tgccgccaac gcgcctacca ccttccccgt cgaggcaccc ccgcttgagg   32340
aggaggaagt gattatcgag caggacccag gttttgtaag cgaagacgac gaggaccgct   32400
cagtaccaac agaggataaa aagcaagacc aggacaacgc agaggcaaac gaggaacaag   32460
tcgggcgggg ggacgaaagg catggcgact acctagatgt gggagacgac gtgctgttga   32520
agcatctgca gcgccagtgc gccattatct gcgacgcgtt gcaagagcgc agcgatgtgc   32580
```

```
ccctcgccat agcggatgtc agccttgcct acgaacgcca cctattctca ccgcgcgtac   32640
cccccaaacg ccaagaaaac ggcacatgcg agcccaaccc gcgcctcaac ttctaccccg   32700
tatttgccgt gccagaggtg cttgccacct atcacatctt tttccaaaac tgcaagatac   32760
ccctatcctg ccgtgccaac cgcagccgag cggacaagca gctggccttg cggcagggcg   32820
ctgtcatacc tgatatcgcc tcgctcaacg aagtgccaaa aatctttgag ggtcttggac   32880
gcgacgagaa gcgcgcggca aacgctctgc aacaggaaaa cagcgaaaat gaaagtcact   32940
ctggagtgtt ggtggaactc gagggtgaca acgcgcgcct agccgtacta aaacgcagca   33000
tcgaggtcac ccactttgcc tacccggcac ttaacctacc ccccaaggtc atgagcacag   33060
tcatgagtga gctgatcgtg cgccgtgcgc agccctggga gagggatgca aatttgcaag   33120
aacaaacaga ggagggccta cccgcagttg gcgacgagca gctagcgcgc tggcttcaaa   33180
cgcgcgagcc tgccgacttg gaggagcgac gcaaactaat gatggccgca gtgctcgtta   33240
ccgtggagct tgagtgcatg cagcggttct ttgctgaccc ggagatgcag cgcaagctag   33300
aggaaacatt gcactacacc tttcgacagg gctacgtacg ccaggcctgc aagatctcca   33360
acgtggagct ctgcaacctg gtctcctacc ttggaatttt gcacgaaaac cgccttgggc   33420
aaaacgtgct tcattccacg ctcaagggcg aggcgcgccg cgactacgtc cgcgactgcg   33480
tttacttatt tctatgctac acctggcaga cggccatggg cgtttggcag cagtgcttgg   33540
aggagtgcaa cctcaaggag ctgcagaaac tgctaaagca aaacttgaag gacctatgga   33600
cggccttcaa cgagcgctcc gtggccgcgc acctggcgga catcattttc cccgaacgcc   33660
tgcttaaaac cctgcaacag ggtctgccag acttcaccag tcaaagcatg ttgcagaact   33720
ttaggaactt tatcctagag cgctcaggaa tcttgcccgc cacctgctgt gcacttccta   33780
gcgactttgt gccattaag taccgcgaat gccctccgcc gctttgggc cactgctacc   33840 ttctgcagct agccaactac cttgcctacc actctgacat aatggaagac gtgagcggtg   33900
acggtctact ggagtgtcac tgtcgctgca acctatgcac cccgcaccgc tccctggttt   33960
gcaattcgca gctgcttaac gaaagtcaaa ttatcggtac ctttgagctg cagggtccct   34020
cgcctgacga aaagtccgcg gctccgggt tgaaactcac tccggggctg tggacgtcgg   34080
cttaccttcg caaatttgta cctgaggact accacgccca cgagattagg ttctacgaag   34140
accaatcccg cccgccaaat gcggagctta ccgcctgcgt cattcccag ggccacattc   34200 ttggccaatt gcaagccatc aacaaagccc gccaagagtt tctgctacga aagggacggg   34260
gggtttactt ggaccccag tccggcgagg agctcaaccc aatcccccg ccgccgcagc   34320 cctatcagca gcagccgcgg gcccttgctt cccaggatgg cacccaaaaa gaagctgcag   34380
ctgccgccgc cacccacgga cgaggaggaa tactgggaca gtcaggcaga ggaggttttg   34440
gacgaggagg aggaggacat gatggaagac tgggagagcc tagacgagga agcttccgag   34500
gtcgaagagg tgtcagacga aacaccgtca ccctcggtcg cattcccctc gccggcgccc   34560
cagaaatcgg caaccggttc cagcatggct acaacctccg ctcctcaggc gccgccggca   34620
ctgcccgttc gccgacccaa ccgtagatgg acaccactg gaaccagggc cggtaagtcc   34680
aagcagccgc cgccgttagc ccaagagcaa caacagcgcc aaggctaccg ctcatggcgc   34740
gggcacaaga acgccatagt tgcttgcttg caagactgtg ggggcaacat ctccttcgcc   34800
cgccgctttc ttctctacca tcacggcgtg gccttccccc gtaacatcct gcattactac   34860
cgtcatctct acagcccata ctgcaccggc ggcagcggca gcggcagcaa cagcagcggc   34920
cacacagaag caaaggcgac cggatagcaa gactctgaca aagcccaaga aatccacagc   34980
```

```
ggcggcagca gcaggaggag gagcgctgcg tctggcgccc aacgaacccg tatcgacccg    35040
cgagcttaga aacaggattt ttcccactct gtatgctata tttcaacaga gcagggggcca   35100 agaacaagag ctgaaaataa aaaacaggtc tctgcgatcc ctcacccgca gctgcctgta    35160
tcacaaaagc gaagatcagc ttcggcgcac gctggaagac gcggaggctc tcttcagtaa    35220
atactgcgcg ctgactctta aggactagtt tcgcgccctt tctcaaattt aagcgcgaaa    35280
actacgtcat ctccagcggc cacacccggc gccagcacct gtcgtcagcg ccattatgag    35340
caaggaaatt cccacgccct acatgtggag ttaccagcca caaatgggac ttgcggctgg    35400
agctgcccaa gactactcaa cccgaataaa ctacatgagc gcgggacccc acatgatatc    35460
ccgggtcaac ggaatccgcg cccaccgaaa ccgaattctc ttggaacagg cggctattac    35520
caccacacct cgtaataacc ttaatccccg tagttggccc gctgccctgg tgtaccagga    35580
aagtcccgct cccaccactg tggtacttcc cagagacgcc caggccgaag ttcagatgac    35640
taactcaggg gcgcagcttg cgggcggctt tcgtcacagg gtgcggtcgc ccgggcaggg    35700
tataactcac ctgacaatca gagggcgagg tattcagctc aacgacgagt cggtgagctc    35760
ctcgcttggt ctccgtccgg acgggacatt tcagatcggc ggcgccggcc gtccttcatt    35820
cacgcctcgt caggcaatcc taactctgca gacctcgtcc tctgagccgc gctctggagg    35880
cattggaact ctgcaattta ttgaggagtt tgtgccatcg gtctacttta accccttctc    35940
gggacctccc ggccactatc cggatcaatt tattcctaac tttgacgcgg taaaggactc    36000
ggcggacggc tacgactgaa tgttaagtgg agaggcagag caactgcgcc tgaaacacct    36060
ggtccactgt cgccgccaca agtgctttgc ccgcgactcc ggtgagtttt gctactttga    36120
attgcccgag gatcatatcg agggcccggc gcacggcgtc cggcttaccg cccagggaga    36180
gcttgcccgt agcctgattc gggagtttac ccagcgcccc ctgctagttg agcgggacag    36240
gggaccctgt gttctcactg tgatttgcaa ctgtcctaac cttggattac atcaagatcc    36300
tctagttata actagagtac ccggggatct tattcccttt aactaataaa aaaaaataat    36360
aaagcatcac ttacttaaaa tcagttagca aatttctgtc cagtttattc agcagccct    36420 ccttgccctc ctcccagctc tggtattgca gcttcctcct ggctgcaaac tttctccaca    36480
atctaaatgg aatgtcagtt tcctcctgtt cctgtccatc cgcacccact atcttcatgt    36540
tgttgcagat gaagcgcgca agaccgtctg aagatacctt caaccccgtg tatccatatg    36600
acacggaaac cggtcctcca actgtgcctt ttcttactcc tcccttttgta tcccccaatg   36660 ggtttcaaga gagtccccct gggtactct cttttgcgcct atccgaacct ctagttacct    36720
ccaatggcat gcttgcgctc aaaatgggca acggcctctc tctggacgag gccggcaacc    36780
ttacctccca aaatgtaacc actgtgagcc cacctctcaa aaaaaccaag tcaaacataa    36840
acctggaaat atctgcaccc ctcacagtta cctcagaagc cctaactgtg gctgccgccg    36900
cacctctaat ggtcgcgggc aacacactca ccatgcaatc acaggcccg ctaaccgtgc     36960 acgactccaa acttagcatt gccacccaag gacccctcac agtgtcagaa ggaaagctag    37020
ccctgcaaac atcaggcccc ctcaccacca ccgatagcag taccccttact atcactgcct   37080 cacccctct aactactgcc actggtagct tgggcattga cttgaaagag cccatttata    37140
cacaaaatgg aaaactagga ctaaagtacg gggctccttt gcatgtaaca gacgacctaa    37200 acacttgac cgtagcaact ggtccaggtg tgactattaa taatacttcc ttgcaaacta    37260
aagttactgg agccttgggt tttgattcac aaggcaatat gcaacttaat gtagcaggag    37320
```

```
gactaaggat tgattctcaa aacagacgcc ttatacttga tgttagttat ccgtttgatg    37380
ctcaaaacca actaaatcta agactaggac agggccctct tttataaaac tcagcccaca    37440
acttggatat taactacaac aaaggccttt acttgtttac agcttcaaac aattccaaaa    37500
agcttgaggt taacctaagc actgccaagg ggttgatgtt tgacgctaca gccatagcca    37560
ttaatgcagg agatgggctt gaatttggtt cacctaatgc accaaacaca aatcccctca    37620
aaacaaaaat tggccatggc ctagaatttg attcaaacaa ggctatggtt cctaaactag    37680
gaactggcct tagttttgac agcacaggtg ccattacagt aggaaacaaa aataatgata    37740
agctaacttt gtggaccaca ccagctccat ctcctaactg tagactaaat gcagagaaag    37800
atgctaaact cactttggtc ttaacaaaat gtggcagtca aatacttgct acagtttcag    37860
ttttggctgt taaaggcagt ttggctccaa tatctggaac agttcaaagt gctcatctta    37920
ttataagatt tgacgaaaat ggagtgctac taaacaattc cttcctggac ccagaatatt    37980
ggaactttag aaatggagat cttactgaag gcacagccta tacaaacgct gttggattta    38040
tgcctaacct atcagcttat ccaaaatctc acggtaaaac tgccaaaagt aacattgtca    38100
gtcaagttta cttaaacgga gacaaaacta aacctgtaac actaaccatt acactaaacg    38160
gtacacagga aacaggagac acaactccaa gtgcatactc tatgtcattt tcatgggact    38220
ggtctggcca caactacatt aatgaaatat ttgccacatc ctcttacact ttttcataca    38280
ttgcccaaga ataaagaatc gtttgtgtta tgtttcaacg tgtttatttt tcaattgcag    38340
aaaatttcaa gtcattttc attcagtagt atagccccac caccacatag cttatacaga    38400
tcaccgtacc ttaatcaaac                                                38420
```

<210> SEQ ID NO 2
<211> LENGTH: 12741
<212> TYPE: DNA
<213> ORGANISM: Artificial Sequence
<220> FEATURE:
<223> OTHER INFORMATION: Synthetic polynucleotide

<400> SEQUENCE: 2

```
aatgtagtct tatgcaatac tcttgtagtc ttgcaacatg gtaacgatga gttagcaaca      60
tgccttacaa ggagagaaaa agcaccgtgc atgccgattg gtggaagtaa ggtggtacga     120
tcgtgcctta ttaggaaggc aacagacggg tctgacatgg attggacgaa ccactgaatt     180
gccgcattgc agagatattg tatttaagtg cctagctcga tacataaacg ggtctctctg     240
gttagaccag atctgagcct gggagctctc tggctaacta gggaacccac tgcttaagcc     300
tcaataaagc ttgccttgag tgcttcaagt agtgtgtgcc cgtctgttgt gtgactctgg     360
taactagaga tccctcagac ccttttagtc agtgtggaaa atctctagca gtggcgcccg     420
aacagggact tgaaagcgaa agggaaacca gaggagctct ctcgacgcag gactcggctt     480
gctgaagcgc gcacggcaag aggcgagggg cggcgactgg tgagtacgcc aaaaattttg     540
actagcggag gctagaagga gagagatggg tgcgagagcg tcagtattaa gcgggggaga     600
attagatcgc gatgggaaaa aattcggtta aggccagggg gaagaaaaaa atataaatta     660
aaacatatag tatgggcaag cagggagcta gaacgattcg cagttaatcc tggcctgtta     720
gaaacatcag aaggctgtag acaaatactg ggacagctac aaccatccct tcagacagga     780
tcagaagaac ttagatcatt atataataca gtagcaaccc tctattgtgt gcatcaaagg     840
atagagataa aagacaccaa ggaagcttta gacaagatag aggaagagca aaacaaaagt     900
aagaccaccg cacagcaagc ggccgctgat cttcagacct ggaggaggag atatgaggga     960
```

```
caattggaga agtgaattat ataaatataa agtagtaaaa attgaaccat taggagtagc    1020
acccaccaag gcaaagagaa gagtggtgca gagagaaaaa agagcagtgg gaataggagc    1080
tttgttcctt gggttcttgg gagcagcagg aagcactatg ggcgcagcgt caatgacgct    1140
gacggtacag gccagacaat tattgtctgg tatagtgcag cagcagaaca atttgctgag    1200
ggctattgag gcgcaacagc atctgttgca actcacagtc tggggcatca agcagctcca    1260
ggcaagaatc ctggctgtgg aaagatacct aaaggatcaa cagctcctgg ggatttgggg    1320
ttgctctgga aaactcattt gcaccactgc tgtgccttgg aatgctagtt ggagtaataa    1380
atctctggaa cagatttgga atcacacgac ctggatggag tgggacagag aaattaacaa    1440
ttacacaagc ttaatacact ccttaattga agaatcgcaa aaccagcaag aaaagaatga    1500
acaagaatta ttggaattag ataaatgggc aagtttgtgg aattggttta acataacaaa    1560
ttggctgtgg tatataaaat tattcataat gatagtagga ggcttggtag gtttaagaat    1620 agttttttgct gtactttcta tagtgaatag agttaggcag ggatattcac cattatcgtt    1680
tcagacccac ctcccaaccc cgaggggacc cgacaggccc gaaggaatag aagaagaagg    1740
tggagagaga gacagagaca gatccattcg attagtgaac ggatctcgac ggtatcgatt    1800
gggcccgaga tctcgcgcgc gaggcctgcc atgggcatgc ctgcaggtcg atgcgtggcc    1860
ggcctaggat ccatatggta ccggtaaatg gcccgcctgg ctgaccgccc aacgaccccc    1920
gcccattgac gtcaataatg acgtatgttc ccatagtaac gccaataggg actttccatt    1980
gacgtcaatg ggtggagtat ttacggtaaa ctgcccactt ggcagtacat caagtgtatc    2040
atatgccaag tacgccccct attgacgtca atgacggtaa atggcccgcc tggcattatg    2100
cccagtacat gaccttatgg gactttccta cttggcagta catctagtat tagtcatcgc    2160
tattaccatg gtgatgcggt tttggcagta catcaatggg cgtggatagc ggtttgactc    2220
acggggattt ccaagtctcc accccattga cgtcaatggg agtttgtttt ggcaccaaaa    2280
tcaacgggac tttccaaaat gtcgtaacaa ctccgcccca ttgacgcaaa tgggcggtag    2340
gcgtgtacgg tggaggtct atataagcag agctcgttta gtgaaccgtc agatcgcctg    2400
gagacgccat ccacgctgtt ttgacctcca tagaagacac cgggaccgat ccagcctccg    2460
cggccgggaa cggtgcattg gaacgcggat tccccgtgcc aagagtgacg taagtaccgc    2520
ctatagactc tataggcaca ccctttggc tcttatgcat gaattaatac gactcactat    2580
agggagacag actgttcctt tcctgggtct tttctgcagg ctagccccac catgccgcgc    2640 gctcccccgct gccgagccgt gcgctccctg ctgcgcagcc actaccgcga ggtgctgccg    2700
ctggccacgt tcgtgcggcg cctggggccc cagggctggc ggctggtgca gcgcggggac    2760
ccggcggctt tccgcgcgct ggtggcccag tgcctggtgt gcgtgccctg ggacgcacgg    2820 ccgcccccg ccgcccctc cttccgccag gtgtcctgcc tgaaggagct ggtggcccga    2880
gtgctgcaga ggctgtgcga gcgcggcgcg aagaacgtgc tggccttcgg cttcgcgctg    2940
ctggacgggg cccgcggggg ccccccgag gccttcacca ccagcgtgcg cagctacctg    3000
cccaacacgg tgaccgacgc actgcggggg agcggggcgt ggggctgct gttgcgccgc    3060 gtgggcgacg acgtgctggt tcacctgctg gcacgctgcg cgctctttgt gctggtggct    3120
cccagctgcg cctaccaggt gtgcgggccg ccgctgtacc agctcggcgc tgccactcag    3180
gcccggcccc cgccacacgc tagtggaccc cgaaggcgtc tgggatgcga acgggcctgg    3240
aaccatagcg tcagggaggc cggggtcccc ctgggcctgc cagccccggg tgcgaggagg    3300
```

```
cgcgggggca gtgccagccg aagtctgccg ttgcccaaga ggcccaggcg tggcgctgcc   3360
cctgagccgg agcggacgcc cgttgggcag gggtcctggg cccacccggg caggacgcgt   3420
ggaccgagtg accgtggttt ctgtgtggtg tcacctgcca gacccgccga agaagccacc   3480
tctttggagg gtgcgctctc tggcacgcgc cactcccacc catccgtggg ccgccagcac   3540
cacgcgggcc ccccatccac atcgcggcca ccacgtccct gggacacgcc ttgtcccccg   3600
gtgtacgccg agaccaagca cttcctctac tcctcaggcg acaaggagca gctgcggccc   3660
tccttcctac tcagctctct gaggcccagc ctgactggcg ctcggaggct cgtggagacc   3720
atctttctgg gttccaggcc ctggatgcca gggactcccc gcaggttgcc ccgcctgccc   3780
cagcgctact ggcaaatgcg gcccctgttt ctggagctgc ttgggaacca cgcgcagtgc   3840
ccctacgggg tgctcctcaa gacgcactgc ccgctgcgag ctgcggtcac cccagcagcc   3900
ggtgtctgtg cccgggagaa gccccagggc tctgtggcgg cccccgagga ggaggacaca   3960 gaccccgtc gcctggtgca gctgctccgc cagcacagca gccctggca ggtgtacggc   4020 ttcgtgcggg cctgcctgcg ccggctggtg ccccaggc tctggggctc caggcacaac   4080
gaacgccgct tcctcaggaa caccaagaag ttcatctccc tggggaagca tgccaagctc   4140
tcgctgcaga agctgacgtg aagatgagc gtgcggggct cgcttggct cgcaggagc   4200 ccaggggttg gctgtgttcc ggccgcagag caccgtctgc gtgaggagat cctggccaag   4260
ttcctgcact ggctgatgag tgtgtacgtc gtcgagctgc tcaggtcttt cttttatgtc   4320
acggagacca cgtttcaaaa gaacaggctc ttttctacc ggaagagtgt ctggagcaag   4380
ttgcaaagca ttggaatcag acagcacttg aagagggtgc agctgcggga gctgtcggaa   4440
gcagaggtca ggcagcatcg ggaagccagg cccgccctgc tgacgtccag actccgcttc   4500
atccccaagc ctgacgggct gcggccgatt gtgaacatgg actacgtcgt gggagccaga   4560
acgttccgca gagaaaagag ggccgagcgt ctcacctcca gggtgaaggc actgttcagc   4620
gtgctcaact acgagcgggc gcggcgcccc ggcctcctgg gcgcctctgt gctgggcctg   4680
gacgatatcc acagggcctg gcgcaccttc gtgctgcgtg tgcgggccca ggacccgccg   4740
cctgagctgt actttgtcaa ggtggatgtg acgggcgcgt acgacaccat cccccaggac   4800
aggctcacgg aggtcatcgc cagcatcatc aaaccccaga acacgtactg cgtgcgtcgg   4860
tatgccgtgg tccagaaggc cgcccatggg cacgtccgca aggccttcaa gagccacgtc   4920
tctaccttga cagacctcca gccgtacatg cgacagttcg tggctcacct gcaggagacc   4980
agcccgctga gggatgccgt cgtcatcgag cagagctcct ccctgaatga ggccagcagt   5040
ggcctcttcg acgtcttcct acgcttcatg tgccaccacg ccgtgcgcat caggggcaag   5100
tcctacgtcc agtgccaggg gatcccgcag ggctccatcc tctccacgct gctctgcagc   5160
ctgtgctacg gcgacatgga gaacaagctg tttgcgggga ttcggcggga cgggctgctc   5220
ctgcgtttgg tggatgattt cttgttggtg acacctcacc tcacccacgc gaaaaccttc   5280
ctcaggaccc tggtccgagg tgtccctgag tatgctgcg tggtgaactt gcggaagaca   5340
gtggtgaact ccctgtaga agacgaggcc ctgggtggca cggcttttgt tcagatgccg   5400
gcccacggcc tattccctg gtgcggcctg ctgctggata cccggaccct ggaggtgcag   5460
agcgactact ccagctatgc ccggacctcc atcagagcca gtctcacctt caaccgcggc   5520
ttcaaggctg ggaggaacat gcgtcgcaaa ctctttgggg tcttgcggct gaagtgtcac   5580
agcctgtttc tggatttgca ggtgaacagc ctccagacgg tgtgcaccaa catctacaag   5640
atcctcctgc tgcaggcgta caggtttcac gcatgtgtgc tgcagctccc atttcatcag   5700
```

-continued

```
caagtttgga agaaccccac attttttcctg cgcgtcatct ctgacacggc ctccctctgc      5760
tactccatcc tgaaagccaa gaacgcaggg atgtcgctgg gggccaaggg cgccgccggc      5820
cctctgccct ccgaggccgt gcagtggctg tgccaccaag cattcctgct caagctgact      5880
cgacaccgtg tcacctacgt gccactcctg gggtcactca ggacagccca gacgcagctg      5940
agtcggaagc tcccggggac gacgctgact gccctggagg ccgcagccaa cccggcactg      6000
ccctcagact tcaagaccat cctggactga gtcgaaactc gaggatccgg ctgtggaatg      6060
tgtgtcagtt agggtgtgga aagtccccag gctccccagc aggcagaagt atgcaaagca      6120
tgcatctcaa ttagtcagca accaggtgtg gaaagtcccc aggctcccca gcaggcagaa      6180
gtatgcaaag catgcatctc aattagtcag caaccatagt cccgccccta actccgccca      6240
tcccgccccct aactccgccc agttccgccc attctccgcc ccatggctga ctaattttttt   6300
ttatttatgc agaggccgag gccgcctcgg cctctgagct attccagaag tagtgaggag      6360
gcttttttgg aggccgtcgg ccgccacgac cggtgccgcc accatcccct gacccacgcc      6420
cctgacccct cacaaggaga cgaccttcca tgaccgagta caagcccacg gtgcgcctcg      6480
ccacccgcga cgacgtcccc cgggccgtac gcaccctcgc cgccgcgttc gccgactacc      6540
ctgcaacacg ccatacagtg gaccctgacc gccacatcga gcgggtcacc gagctgcaag      6600
aactcttcct cacgcgcgtc gggctcgaca tcggcaaggt gtgggtcgcg gacgacggcg      6660
ccgcggtggc ggtctggacc acgccggaga gcgtcgaagc gggggcggtg ttcgccgaga      6720
tcggcccgcg catggccgag ttgagcggtt cccggctggc cgcgcagcaa cagatggaag      6780
gcctcctggc gccgcaccgg cccaaggagc ccgcgtggtt cctggccacc gtcggcgtct      6840
cgccccgacca ccagggcaag ggtctgggca gcgccgtcgt gctccccgga gtggaggcgg      6900
ccgagcgcgc cggggtgccc gccttcctgg agacctccgc gccccgcaac ctccccttct      6960
acgagcggct cggcttcacc gtcaccgccg acgtcgaggt gcccgaagga ccgcgcacct      7020
ggtgcatgac ccgcaagccc ggtgcctgac gcccgcccca cgacccgcag cgcccgaccg      7080
aaaggagcgc acgaccccat gcatcgataa aataaaagat tttatttagt ctccagaaaa      7140
agggggggaat gaaagacccc acctgtaggt ttggcaagct aggcctatta atattccgga    7200
gtatacgtag ccggctaacg ttaacaaccg gtacgatgca ttagttatta atagtaatca    7260
attacggggt cattagttca tagcccatat atggagttcc gcgttacata acttacggta    7320
aatggcccgc ctggctgacc gcccaacgac ccccgcccat tgacgtcaat aatgacgtat    7380
gttcccatag taacgccaat agggactttc cattgacgtc aatgggtgga gtatttacgg    7440
taaactgccc acttggcagt acatcaagtg tatcatatgc caagtacgcc ccctattgac    7500
gtcaatgacg gtaaatggcc cgcctggcat tatgcccagt acatgacctt atgggacttt    7560
cctacttggc agtacatcta cgtattagtc atcgctatta ccatggtgat gcggttttgg    7620
cagtacatca atgggcgtgg atagcggttt gactcacggg gatttccaag tctccacccc    7680
attgacgtca atgggagttt gttttggcac caaaatcaac gggactttcc aaaatgtcgt    7740
aacaactccg ccccattgac gcaaatgggc ggtaggcgtg tacggtggga ggtctatata    7800
agcagagctg gtttagtgaa ccgtcagatc cgctagcgct accggactca gatctcgagc    7860
tcaagcttcg aattctgcag tcgacccacc atggctcttt caaacaagtt tatcggagat    7920
gacatgaaaa tgacctacca tatgatggc tgtgtcaatg gcattacttt taccgtcaaa    7980
ggtgaaggca gcgggaagcc atacgaaggg acgcagacct cgactttaa agtcaccatg    8040
```

```
gccaacggtg ggccccttgc attctccttt gacatactat ctacagtgtt catgtatgga    8100
aatcgatgct ttactgcgta tcctaccagt atgcccgact atttcaaaca agcatttcct    8160
gacggaatgt catatgaaag acttttacc tatgaagatg gaggagttgc tacagccagt     8220
tgggaaataa gccttaaagg caactgcttt gagcacaaat ccacgtttca tggagtgaac    8280
tttcctgctg atggacctgt gatggcgaag atgacaactg gttgggaccc atcttttgag    8340
aaaatgactg tctgcgatgg aatattgaag ggtgatgtca ccgcgttcct catgctgcaa    8400
ggaggtggca attacagatg ccaattccac acttcttaca agacaaaaaa accggtgacg    8460
atgccaccaa accatgcggt ggaacatcgc attgcgagga ccgaccttga caaaggtggc    8520
aacagtgttc agctgacgga gcacgctgtt gcacatataa cctctgttgt ccctttctag    8580
cggccgcgat aatcaacctc tggattacaa aatttgtgaa agattgactg gtattcttaa    8640
ctatgttgct ccttttacgc tatgtggata cgctgcttta atgcctttgt atcatgctat    8700
tgcttcccgt atggctttca ttttctcctc cttgtataaa tcctggttgc tgtctcttta    8760
tgaggagttg tggcccgttg tcaggcaacg tggcgtggtg tgcactgtgt ttgctgacgc    8820
aacccccact ggttggggca ttgccaccac ctgtcagctc ctttccggga ctttcgcttt    8880
ccccctccct attgccacgg cggaactcat cgccgcctgc cttgcccgct gctggacagg    8940
ggctcggctg ttgggcactg acaattccgt ggtgttgtcg gggaagctga cgtccttct    9000
atggctgctc gcctgtgttg ccacctggat tctgcgcggg acgtccttct gctacgtccc    9060
ttcggccctc aatccagcgg accttccttc ccgcggcctg ctgccggctc tgcggcctct    9120
tccgcgtctt cgccttcgcc ctcagacgag tcggatctcc ctttgggccg cctccccgca    9180
tcggacgcgt ggtacctta agaccaatga cttacaaggc agctgtagat cttagccact    9240
ttttaaaaga aaaggggga ctggaagggc taattcactc ccaacgaaga caagatctgc    9300
ttttttgcttg tactgggtct ctctggttag accagatctg agcctgggag ctctctggct    9360
aactagggaa cccactgctt aagcctcaat aaagcttgcc ttgagtgctt caagtagtgt    9420
gtgcccgtct gttgtgtgac tctggtaact agagatccct cagaccctt tagtcagtgt     9480
ggaaaatctc tagcagtagt agttcatgtc atcttattat tcagtattta taacttgcaa    9540
agaaatgaat atcagagagt gagaggaact tgtttattgc agcttataat ggttacaaat    9600
aaagcaatag catcacaaat ttcacaaata aagcattttt ttcactgcat tctagttgtg    9660
gtttgtccaa actcatcaat gtatcttatc atgtctggct ctagctatcc cgcccctaac    9720
tccgcccatc ccgcccctaa ctccgcccag ttccgcccat tctccgcccc atggctgact    9780
aattttttt atttatgcag aggccgaggc cgcctcggcc tctgagctat tccagaagta    9840
gtgaggaggc ttttttggag gcctaggac gtacccaatt cgccctatag tgagtcgtat    9900
tacgcgcgct cactggccgt cgttttacaa cgtcgtgact gggaaaaccc tggcgttacc    9960
caacttaatc gccttgcagc acatcccct ttcgccagct ggcgtaatag cgaagaggcc     10020
cgcaccgatc gcccttccca acagttgcgc agcctgaatg gcgaatggga cgcgccctgt    10080
agcggcgcat taagcgcggc gggtgtggtg gttacgcgca gcgtgaccgc tacacttgcc    10140
agcgccctag cgcccgctcc tttcgctttc ttcccttcct ttctcgccac gttcgccggc    10200
tttccccgtc aagctctaaa tcgggggctc cctttagggt tccgatttag tgctttacgg    10260
cacctcgacc ccaaaaaact tgattagggt gatggttcac gtagtgggcc atcgccctga    10320
tagacggttt ttcgcccttt gacgttggag tccacgttct ttaatagtgg actcttgttc    10380
caaactggaa caacactcaa ccctatctcg gtctattctt ttgatttata agggattttg    10440
```

```
ccgatttcgg cctattggtt aaaaaatgag ctgatttaac aaaaatttaa cgcgaatttt    10500
aacaaaatat taacgcttac aatttaggtg gcacttttcg gggaaatgtg cgcggaaccc    10560
ctatttgttt attttttctaa atacattcaa atatgtatcc gctcatgaga caataaccct    10620
gataaatgct tcaataatat tgaaaaagga agagtatgag tattcaacat ttccgtgtcg    10680
cccttattcc cttttttgcg gcattttgcc ttcctgtttt tgctcaccca gaaacgctgg    10740
tgaaagtaaa agatgctgaa gatcagttgg gtgcacgagt gggttacatc gaactggatc    10800
tcaacagcgg taagatcctt gagagttttc gccccgaaga acgttttcca atgatgagca    10860
cttttaaagt tctgctatgt ggcgcggtat tatcccgtat tgacgccggg caagagcaac    10920
tcggtcgccg catacactat tctcagaatg acttggttga gtactcacca gtcacagaaa    10980
agcatcttac ggatggcatg acagtaagag aattatgcag tgctgccata accatgagtg    11040
ataacactgc ggccaactta cttctgacaa cgatcggagg accgaaggag ctaaccgctt    11100
ttttgcacaa catgggggat catgtaactc gccttgatcg ttgggaaccg gagctgaatg    11160
aagccatacc aaacgacgag cgtgacacca cgatgcctgt agcaatggca acaacgttgc    11220
gcaaactatt aactggcgaa ctacttactc tagcttcccg gcaacaatta atagactgga    11280
tggaggcgga taaagttgca ggaccacttc tgcgctcggc ccttccggct ggctggttta    11340
ttgctgataa atctggagcc ggtgagcgtg ggtctcgcgg tatcattgca gcactggggc    11400
cagatggtaa gccctcccgt atcgtagtta tctacacgac ggggagtcag gcaactatgg    11460
atgaacgaaa tagacagatc gctgagatag gtgcctcact gattaagcat tggtaactgt    11520
cagaccaagt ttactcatat atactttaga ttgatttaaa acttcatttt taatttaaaa    11580
ggatctaggt gaagatcctt tttgataatc tcatgaccaa aatcccttaa cgtgagtttt    11640
cgttccactg agcgtcagac cccgtagaaa agatcaaagg atcttcttga gatcctttt    11700 ttctgcgcgt aatctgctgc ttgcaaacaa aaaaaccacc gctaccagcg gtggtttgtt    11760
tgccggatca agagctacca actctttttc cgaaggtaac tggcttcagc agagcgcaga    11820
taccaaatac tgttcttcta gtgtagccgt agttaggcca ccacttcaag aactctgtag    11880
caccgcctac atacctcgct ctgctaatcc tgttaccagt ggctgctgcc agtggcgata    11940
agtcgtgtct taccgggttg gactcaagac gatagttacc ggataaggcg cagcggtcgg    12000
gctgaacggg gggttcgtgc acacagccca gcttggagcg aacgacctac accgaactga    12060
gatacctaca gcgtgagcta tgagaaagcg ccacgcttcc cgaagggaga aaggcggaca    12120
ggtatccggt aagcggcagg gtcggaacag gagagcgcac gagggagctt ccagggggaa    12180
acgcctggta tctttatagt cctgtcgggt ttcgccacct ctgacttgag cgtcgatttt    12240
tgtgatgctc gtcaggggg cggagcctat ggaaaaacgc cagcaacgcg gcctttttac    12300
ggttcctggc cttttgctgg ccttttgctc acatgttctt tcctgcgtta tcccctgatt    12360
ctgtggataa ccgtattacc gcctttgagt gagctgatac cgctcgccgc agccgaacga    12420
ccgagcgcag cgagtcagtg agcgaggaag cggaagagcg cccaatacgc aaaccgcctc    12480
tccccgcgcg ttggccgatt cattaatgca gctggcacga caggtttccc gactggaaag    12540
cgggcagtga gcgcaacgca attaatgtga gttagctcac tcattaggca ccccaggctt    12600
tacactttat gcttccggct cgtatgttgt gtggaattgt gagcggataa caatttcaca    12660
caggaaacag ctatgaccat gattacgcca agcgcgcaat taaccctcac taaagggaac    12720
aaaagctgga gctgcaagct t                                              12741
```

<210> SEQ ID NO 3
<211> LENGTH: 11626
<212> TYPE: DNA
<213> ORGANISM: Artificial Sequence
<220> FEATURE:
<223> OTHER INFORMATION: Synthetic polynucleotide

<400> SEQUENCE: 3

| | | | | | |
|---|---|---|---|---|---|
| aatgtagtct | tatgcaatac | tcttgtagtc | ttgcaacatg | gtaacgatga | gttagcaaca | 60 |
| tgccttacaa | ggagagaaaa | agcaccgtgc | atgccgattg | gtggaagtaa | ggtggtacga | 120 |
| tcgtgcctta | ttaggaaggc | aacagacggg | tctgacatgg | attggacgaa | ccactgaatt | 180 |
| gccgcattgc | agagatattg | tatttaagtg | cctagctcga | tacataaacg | ggtctctctg | 240 |
| gttagaccag | atctgagcct | gggagctctc | tggctaacta | gggaacccac | tgcttaagcc | 300 |
| tcaataaagc | ttgccttgag | tgcttcaagt | agtgtgtgcc | cgtctgttgt | gtgactctgg | 360 |
| taactagaga | tccctcagac | cctttttagtc | agtgtggaaa | atctctagca | gtggcgcccg | 420 |
| aacagggact | tgaaagcgaa | agggaaacca | gaggagctct | ctcgacgcag | gactcggctt | 480 |
| gctgaagcgc | gcacggcaag | aggcgagggg | cggcgactgg | tgagtacgcc | aaaaattttg | 540 |
| actagcggag | gctagaagga | gagagatggg | tgcgagagcg | tcagtattaa | gcggggggaga | 600 |
| attagatcgc | gatgggaaaa | aattcggtta | aggccagggg | gaagaaaaa | atataaatta | 660 |
| aaacatatag | tatgggcaag | cagggagcta | gaacgattcg | cagttaatcc | tggcctgtta | 720 |
| gaaacatcag | aaggctgtag | acaaatactg | ggacagctac | aaccatccct | tcagacagga | 780 |
| tcagaagaac | ttagatcatt | atataataca | gtagcaaccc | tctattgtgt | gcatcaaagg | 840 |
| atagagataa | aagacaccaa | ggaagcttta | gacaagatag | aggaagagca | aaacaaaagt | 900 |
| aagaccaccg | cacagcaagc | ggccgctgat | cttcagacct | ggaggaggag | atatgaggga | 960 |
| caattggaga | agtgaattat | ataaatataa | agtagtaaaa | attgaaccat | taggagtagc | 1020 |
| acccaccaag | gcaaagagaa | gagtggtgca | gagagaaaaa | agagcagtgg | gaataggagc | 1080 |
| tttgttcctt | gggttcttgg | gagcagcagg | aagcactatg | ggcgcagcgt | caatgacgct | 1140 |
| gacggtacag | gccagacaat | tattgtctgg | tatagtgcag | cagcagaaca | atttgctgag | 1200 |
| ggctattgag | gcgcaacagc | atctgttgca | actcacagtc | tggggcatca | agcagctcca | 1260 |
| ggcaagaatc | ctggctgtgg | aaagatacct | aaaggatcaa | cagctcctgg | ggatttgggg | 1320 |
| ttgctctgga | aaactcattt | gcaccactgc | tgtgccttgg | aatgctagtt | ggagtaataa | 1380 |
| atctctggaa | cagatttgga | atcacacgac | ctggatggag | tgggacagag | aaattaacaa | 1440 |
| ttacacaagc | ttaatacact | ccttaattga | agaatcgcaa | aaccagcaag | aaaagaatga | 1500 |
| acaagaatta | ttggaattag | ataaatgggc | aagtttgtgg | aattggttta | acataacaaa | 1560 |
| ttggctgtgg | tatataaaat | tattcataat | gatagtagga | ggcttggtag | gtttaagaat | 1620 |
| agttttttgct | gtactttcta | tagtgaatag | agttaggcag | ggatattcac | cattatcgtt | 1680 |
| tcagacccac | ctcccaaccc | cgaggggacc | cgacaggccc | gaaggaatag | aagaagaagg | 1740 |
| tggagagaga | gacagagaca | gatccattcg | attagtgaac | ggatctcgac | ggtatcgata | 1800 |
| ctagtaattt | ttctgcagaa | aacgtacccg | gggatcctct | aggatcccac | cgaaaggttg | 1860 |
| ctccttaaca | caggctaagg | accagcttct | tgggagaga | acagacgcag | ggcgggagg | 1920 |
| gaaaaaggga | gaggcagacg | tcacttcccc | ttggcggctc | tggcagcaga | ttggtcggtt | 1980 |
| gagtggcaga | aaggcagacg | gggactgggc | aaggcactgt | cggtgacatc | acggacaggg | 2040 |
| cgacttctat | gtagatgagg | cagcgcagag | gctgctgctt | cgccacttgc | tgcttcgcca | 2100 |

-continued

```
cgaaggagtt cccgtgccct gggagcgggt tcaggaccgc ggatcggaag tgagaatccc    2160
agctgtgtgt cagggctgga aagggctcgg gagtgcgcgg ggcaagtgac cgtgtgtgta    2220
aagagtgagg cgtatgaggc tgtgtcgggg cagagcccga agatccgggt tgcggagggt    2280
gggcctggga ggggtggtgg ccatttttg tctaaccca actgagaagg gcgtaggcgc     2340
cgtgcttttg ctccccgcgc gctgttttc tcgctgactt tcagcgggcg gaaaagcctc    2400
ggcctgccgc cttccaccgt tcattctaga gcaaacaaaa aatgtcagct gctggcccgt    2460
tcgcccctcc cggggacctg cggcgggtcg cctgcccagc ccccgaaccc cgcctggagg    2520
ccgcggtcgg cccggggctt ctccggaggc acccactgcc accgcgaaga gttgggctct    2580
gtcagccgcg ggtctctcgg gggcgagggc gaggttcagg cctttcaggc cgcaggaaga    2640
ggaacggagc gagtccccgc gcgcggcgcg attccctgag ctgtgggacg tgcacccagg    2700
actcggctca cacatgcagt tcgctttcct gttggtgggg ggaacgccga tcgtgcgcat    2760
ccgtcacccc tcgccggcaa tgggggcttg tgaaccccca aacctgactg actgggccag    2820
tgtgctgcaa attggcagga gacgtgaagg cacctccaaa gtcgactttc tggagtttca    2880
aaaacagacc gtacatgtcc gcggtcgcga cgtacctacc gggtagggga ggcgcttttc    2940
ccaaggcagt ctggagcatg cgctttagca gccccgctgg gcacttggcg ctacacaagt    3000
ggcctctggc ctcgcacaca ttccacatcc accggtaggc gccaaccggc tccgttcttt    3060
ggtggcccct tcgcgccacc ttctactcct cccctagtca ggaagttccc ccccgccccg    3120
cagctcgcgt cgtgcaggac gtgacaaatg gaagtagcac gtctcactag tctcgtgcag    3180
atggacagca ccgctgagca atggaagcgg gtaggccttt ggggcagcgg ccaatagcag    3240 cttttgctcct tcgctttctg ggctcagagg ctgggaaggg gtgggtccgg gggcgggctc    3300
aggggcgggc tcaggggcgg ggcgggcgcc cgaagtcctc cggaggcccg gcattctgca    3360
cgcttcaaaa gcgcacgtct gccgcgctgt tctcctcttc ctcatctccg ggcctttcga    3420
ctctagacac gtgttgacaa ttaatcatcg gcatagtata tcggcatagt ataatacgac    3480
aaggtgagga actaaaccat ggccaagcct ttgtctcaag aagaatccac cctcattgaa    3540
agagcaacgg ctacaatcaa cagcatcccc atctctgaag actacagcgt cgccagcgca    3600
gctctctcta gcgacggccg catcttcact ggtgtcaatg tatatcattt tactggggga    3660
ccttgtgcag aactcgtggt gctgggcact gctgctgctg cggcagctgg caacctgact    3720
tgtatcgtcg cgatcggaaa tgagaacagg ggcatcttga gccctgcgg acggtgccga    3780 caggtgcttc tcgatctgca tcctgggatc aaagccatag tgaaggacag tgatggacag    3840
ccgacggcag ttgggattcg tgaattgctg ccctctggtt atgtgtggga gggctaagca    3900
caattcgagc tcggtacgcg tatcgatggc gccagctgca ggcggccgcc atatgcatcc    3960
taggcctatt aatattccgg agtatacgta gccggctaac gttaacaacc ggtacgatgc    4020
attagttatt aatagtaatc aattacgggg tcattagttc atagcccata tatggagttc    4080
cgcgttacat aacttacggt aaatggcccg cctggctgac cgcccaacga cccccgccca    4140
ttgacgtcaa taatgacgta tgttcccata gtaacgccaa tagggacttt ccattgacgt    4200
caatgggtgg agtatttacg gtaaactgcc cacttggcag tacatcaagt gtatcatatg    4260
ccaagtacgc cccctattga cgtcaatgac ggtaaatggc ccgcctggca ttatgcccag    4320
tacatgacct tatgggactt tcctacttgg cagtacatct acgtattagt catcgctatt    4380
accatggtga tgcggttttg gcagtacatc aatgggcgtg gatagcggtt tgactcacgg    4440
```

```
ggatttccaa gtctccaccc cattgacgtc aatgggagtt tgttttggca ccaaaatcaa    4500
cgggactttc caaaatgtcg taacaactcc gccccattga cgcaaatggg cggtaggcgt    4560
gtacggtggg aggtctatat aagcagagct ggtttagtga accgtcagat ccgctagccc    4620
caccatgccg cgcgctcccc gctgccgagc cgtgcgctcc ctgctgcgca gccactaccg    4680
cgaggtgctg ccgctggcca cgttcgtgcg gcgcctgggg ccccagggct ggcggctggt    4740
gcagcgcggg gacccggcgg cttccgcgc gctggtggcc cagtgcctgg tgtgcgtgcc    4800
ctgggacgca cggccgcccc ccgccgcccc ctccttccgc caggtgtcct gcctgaagga    4860
gctggtggcc cgagtgctgc agaggctgtg cgagcgcggc gcgaagaacg tgctggcctt    4920
cggcttcgcg ctgctggacg gggcccgcgg gggcccccc gaggccttca ccaccagcgt    4980
gcgcagctac ctgcccaaca cggtgaccga cgcactgcgg gggagcgggg cgtgggggct    5040
gctgttgcgc cgcgtgggcg acgacgtgct ggttcacctg ctggcacgct gcgcgctctt    5100
tgtgctggtg gctcccagct gcgcctacca ggtgtgcggg ccgccgctgt accagctcgg    5160
cgctgccact caggcccggc ccccgccaca cgctagtgga ccccgaaggc gtctgggatg    5220
cgaacgggcc tggaaccata cgtcaggga ggccggggtc ccctgggcc tgccagcccc    5280 gggtgcgagg aggcgcgggg gcagtgccag ccgaagtctg ccgttgccca agaggcccag    5340
gcgtggcgct gccctgagc cggagcggac gcccgttggg caggggtcct gggcccaccc    5400
gggcaggacg cgtggaccga gtgaccgtgg tttctgtgtg gtgtcacctg ccagacccgc    5460
cgaagaagcc acctctttgg agggtgcgct ctctggcacg cgccactccc acccatccgt    5520
gggccgccag caccacgcgg gccccccatc cacatcgcgg ccaccacgtc cctgggacac    5580
gccttgtccc ccggtgtacg ccgagaccaa gcacttcctc tactcctcag gcgacaagga    5640
gcagctgcgg ccctccttcc tactcagctc tctgaggccc agcctgactg gcgctcggag    5700
gctcgtggag accatctttc tgggttccag gccctggatg ccaggactc cccgcaggtt    5760 gccccgcctg ccccagcgct actggcaaat gcggcccctg tttctggagc tgcttgggaa    5820
ccacgcgcag tgcccctacg gggtgctcct caagacgcac tgcccgctgc gagctgcggt    5880
caccccagca gccggtgtct gtgcccggga aagcccccag ggctctgtgg cggccccga    5940 ggaggaggac acagaccccc gtcgcctggt gcagctgctc cgccagcaca gcagcccctg    6000
gcaggtgtac ggcttcgtgc gggcctgcct gcgccggctg gtgccccag gcctctgggg    6060 ctccaggcac aacgaacgcc gcttcctcag gaacaccaag aagttcatct ccctggggaa    6120
gcatgccaag ctctcgctgc aggagctgac gtggaagatg agcgtgcggg gctgcgcttg    6180
gctgcgcagg agcccagggg ttggctgtgt tccggccgca gagcaccgtc tgcgtgagga    6240
gatcctggcc aagttcctgc actggctgat gagtgtgtac gtcgtcgagc tgctcaggtc    6300
tttcttttat gtcacggaga ccacgtttca aaagaacagg ctcttttct accggaagag    6360 tgtctggagc aagttgcaaa gcattggaat cagacagcac ttgaagaggg tgcagctgcg    6420
ggagctgtcg gaagcagagg tcaggcagca tcgggaagcc aggcccgccc tgctgacgtc    6480
cagactccgc ttcatcccca agcctgacgg gctgcggccg attgtgaaca tggactacgt    6540
cgtgggagcc agaacgttcc gcagagaaaa gagggccgag cgtctcacct ccagggtgaa    6600
ggcactgttc agcgtgctca actacgagcg ggcgcggcgc cccggcctcc tgggcgcctc    6660
tgtgctgggc ctggacgata tccacagggc ctggcgcacc ttcgtgctgc gtgtgcgggc    6720
ccaggacccg ccgcctgagc tgtactttgt caaggtggat gtgacgggcg cgtacgacac    6780
catcccccag gacaggctca cggaggtcat cgccagcatc atcaaacccc agaacacgta    6840
```

```
ctgcgtgcgt cggtatgccg tggtccagaa ggccgcccat gggcacgtcc gcaaggcctt      6900
caagagccac gtctctacct tgacagacct ccagccgtac atgcgacagt tcgtggctca      6960
cctgcaggag accagcccgc tgagggatgc cgtcgtcatc gagcagagct cctccctgaa      7020
tgaggccagt agtggcctct tcgacgtctt cctacgcttc atgtgccacc acgccgtgcg      7080
catcaggggc aagtcctacg tccagtgcca ggggatcccg cagggctcca tcctctccac      7140
gctgctctgc agcctgtgct acggcgacat ggagaacaag ctgtttgcgg ggattcggcg      7200
ggacgggctg ctcctgcgtt tggtggatga tttcttgttg gtgacacctc acctcaccca      7260
cgcgaaaacc ttcctcagga ccctggtccg aggtgtccct gagtatggct gcgtggtgaa      7320
cttgcggaag acagtggtga acttccctgt agaagacgag gccctgggtg cacggctttt      7380
tgttcagatg ccggcccacg gcctattccc ctggtgcggc ctgctgctgg atcccggac      7440 cctggaggtg cagagcgact actccagcta tgcccggacc tccatcagag ccagtctcac      7500
cttcaaccgc ggcttcaagg ctgggaggaa catgcgtcgc aaactctttg ggtcttgcg      7560 gctgaagtgt cacagcctgt ttctggattt gcaggtgaac agcctccaga cggtgtgcac      7620
caacatctac aagatcctcc tgctgcaggc gtacaggttt cacgcatgtg tgctgcagct      7680
cccatttcat cagcaagttt ggaagaaccc cacatttttc ctgcgcgtca tctctgacac      7740
ggcctccctc tgctactcca tcctgaaagc caagaacgca gggatgtcgc tggggggccaa      7800 gggcgccgcc ggccctctgc cctccgaggc cgtgcagtgg ctgtgccacc aagcattcct      7860
gctcaagctg actcgacacc gtgtcaccta cgtgccactc ctggggtcac tcaggacagc      7920
ccagacgcag ctgagtcgga agctcccggg gacgacgctg actgccctgg aggccgcagc      7980
caacccggca ctgccctcag acttcaagac catcctggac tgagtcgaaa ctcgcggccg      8040
catgcgtcga cgcgtatcga tgcatcttaa gtagatgtac ctttaagacc aatgacttac      8100
aaggcagctg tagatcttag ccacttttta aaagaaaagg ggggactgga agggctaatt      8160
cactcccaac gaagacaaga tctgcttttt gcttgtactg ggtctctctg gttagaccag      8220
atctgagcct gggagctctc tggctaacta gggaacccac tgcttaagcc tcaataaagc      8280
ttgccttgag tgcttcaagt agtgtgtgcc cgtctgttgt gtgactctgg taactagaga      8340
tccctcagac ccttttagtc agtgtggaaa atctctagca gtagtagttc atgtcatctt      8400
attattcagt atttataact tgcaaagaaa tgaatatcag agagtgagag gaacttgttt      8460
attgcagctt ataatggtta caaataaagc aatagcatca caaatttcac aaataaagca      8520 ttttttcac tgcattctag ttgtggtttg tccaaactca tcaatgtatc ttatcatgtc      8580
tggctctagc tatcccgccc ctaactccgc ccatcccgcc ctaactccg cccagttccg      8640 cccattctcc gccccatggc tgactaattt tttttattta tgcagaggcc gaggccgcct      8700
cggcctctga gctattccag aagtagtgag gaggcttttt tggaggccta gggacgtacc      8760
caattcgccc tatagtgagt cgtattacgc gcgctcactg gccgtcgttt tacaacgtcg      8820
tgactgggaa aaccctggcg ttacccaact taatcgcctt gcagcacatc ccccctttcgc     8880 cagctggcgt aatagcgaag aggcccgcac cgatcgccct tcccaacagt tgcgcagcct      8940
gaatggcgaa tgggacgcgc cctgtagcgg cgcattaagc gcggcgggtg tggtggttac      9000
gcgcagcgtg accgctacac ttgccagcgc cctagcgccc gctcctttcg ctttcttccc      9060
ttcctttctc gccacgttcg ccggctttcc ccgtcaagct ctaaatcggg gctcccttt      9120 agggttccga tttagtgctt tacggcacct cgaccccaaa aaacttgatt agggtgatgg      9180
```

```
ttcacgtagt gggccatcgc cctgatagac ggttttttcgc cctttgacgt tggagtccac   9240
gttctttaat agtggactct tgttccaaac tggaacaaca ctcaacccta tctcggtcta   9300
ttcttttgat ttataaggga ttttgccgat ttcggcctat tggttaaaaa atgagctgat   9360
ttaacaaaaa tttaacgcga attttaacaa aatattaacg cttacaattt aggtggcact   9420
tttcggggaa atgtgcgcgg aacccctatt tgtttatttt tctaaataca ttcaaatatg   9480
tatccgctca tgagacaata accctgataa atgcttcaat aatattgaaa aaggaagagt   9540
atgagtattc aacatttccg tgtcgccctt attccctttt ttgcggcatt ttgccttcct   9600
gttttgctc acccagaaac gctggtgaaa gtaaaagatg ctgaagatca gttgggtgca   9660
cgagtgggtt acatcgaact ggatctcaac agcggtaaga tccttgagag ttttcgcccc   9720
gaagaacgtt ttccaatgat gagcactttt aaagttctgc tatgtggcgc ggtattatcc   9780
cgtattgacg ccgggcaaga gcaactcggt cgccgcatac actattctca gaatgacttg   9840
gttgagtact caccagtcac agaaaagcat cttacggatg gcatgacagt aagagaatta   9900
tgcagtgctg ccataaccat gagtgataac actgcggcca acttacttct gacaacgatc   9960
ggaggaccga aggagctaac cgcttttttg cacaacatgg gggatcatgt aactcgcctt  10020
gatcgttggg aaccggagct gaatgaagcc ataccaaacg acgagcgtga ccacacgatg  10080
cctgtagcaa tggcaacaac gttgcgcaaa ctattaactg gcgaactact tactctagct  10140
tcccggcaac aattaataga ctggatggag gcggataaag ttgcaggacc acttctgcgc  10200
tcggcccttc cggctggctg gtttattgct gataaatctg gagccggtga gcgtgggtct  10260
cgcggtatca ttgcagcact ggggccagat ggtaagccct cccgtatcgt agttatctac  10320
acgacgggga gtcaggcaac tatggatgaa cgaaatagac agatcgctga gataggtgcc  10380
tcactgatta agcattggta actgtcagac caagtttact catatatact ttagattgat  10440
ttaaaacttc attttttaatt taaaaggatc taggtgaaga tcctttttga atctcatg  10500
accaaaatcc cttaacgtga gttttcgttc cactgagcgt cagacccgt agaaaagatc  10560
aaaggatctt cttgagatcc ttttttttctg cgcgtaatct gctgcttgca acaaaaaaa  10620
ccaccgctac cagcggtggt ttgtttgccg gatcaagagc taccaactct ttttccgaag  10680
gtaactggct tcagcagagc gcagatacca aatactgttc ttctagtgta gccgtagtta  10740
ggccaccact tcaagaactc tgtagcaccg cctacatacc tcgctctgct aatcctgtta  10800
ccagtggctg ctgccagtgg cgataagtcg tgtcttaccg ggttggactc aagacgatag  10860
ttaccggata aggcgcagcg gtcgggctga acggggggtt cgtgcacaca gcccagcttg  10920
gagcgaacga cctacaccga actgagatac ctacagcgtg agctatgaga aagcgccacg  10980
cttcccgaag ggagaaaggc ggacaggtat ccggtaagcg gcagggtcgg aacaggagag  11040
cgcacgaggg agcttccagg gggaaacgcc tggtatcttt atagtcctgt cgggtttcgc  11100
cacctctgac ttgagcgtcg attttttgtga tgctcgtcag ggggggcggag cctatggaaa  11160
aacgccagca acgcggcctt tttacggttc ctggcctttt gctggccttt tgctcacatg  11220
ttctttcctg cgttatcccc tgattctgtg ataaccgta ttaccgcctt tgagtgagct  11280
gataccgctc gccgcagccg aacgaccgag cgcagcgagt cagtgagcga ggaagcggaa  11340
gagcgcccaa tacgcaaacc gcctctcccc gcgcgttggc cgattcatta atgcagctgg  11400
```

-continued

```
cacgacaggt ttcccgactg gaaagcgggc agtgagcgca acgcaattaa tgtgagttag  11460
ctcactcatt aggcacccca ggctttacac tttatgcttc cggctcgtat gttgtgtgga  11520
attgtgagcg gataacaatt tcacacagga aacagctatg accatgatta cgccaagcgc  11580
gcaattaacc ctcactaaag ggaacaaaag ctggagctgc aagctt               11626
```

ENHANCING HEALTH IN MAMMALS USING TELOMERASE REVERSE TRANSCRIPTASE GENE THERAPY

INTRODUCTION

The improvement of health during aging is of interest in aging research. Markers of aging include conditions such as epithelial barrier fitness, osteoporosis, glucose intolerance with insulin insensitivity, loss of memory, and neuromuscular degeneration associated with loss of neuromuscular coordination. For example, bone loss is a well-characterized sign of the aging progress both in mammals including humans which results from bone resorption due to osteoblast insufficiency. Therefore, methods that increase life span and ameliorate various age-related parameters are of interest.

Telomeres are regions of repetitive DNA found at the ends of the chromosomes of most eukaryotes. For example, human telomeres include many kilobases of (TTAGGG)n and are associated with various proteins. Small portions of these terminal sequences of telomeric DNA are lost from the tips of the chromosomes during the S phase of the cell cycle because of incomplete DNA replication. Many human cells progressively lose terminal sequences with cell division, a loss that correlates with the apparent absence of telomerase in these cells. The resulting telomere shortening limits cellular lifespan.

Telomerase is a ribonucleoprotein that synthesizes telomeric DNA. Telomerase is made up of two components: (1) an essential structural RNA component (TR or TER) (in humans the component is referred to as hTR or hTER), and (2) a catalytic protein (telomerase reverse transcriptase or TERT) (in humans the component is referred to as hTERT). Telomerase works by adding multiple DNA sequence repeats to the 3' end of DNA in the telomere region, where hTER serves as the template for nucleotide incorporation, and TERT as the catalyst. Both the catalytic protein component and the RNA template component of telomerase are activity-limiting components.

SUMMARY

Methods of treating an age-related disorder or condition in a subject are provided. Aspects of the methods include administering to the subject a nucleic acid vector including a coding sequence for telomerase reverse transcriptase (TERT) and/or telomerase RNA (TR). Gene therapy methods are also provided. Aspects of the invention further include compositions, e.g., nucleic acid vectors and kits, etc., that find use in methods of the invention.

DETAILED DESCRIPTION

Figure 1:
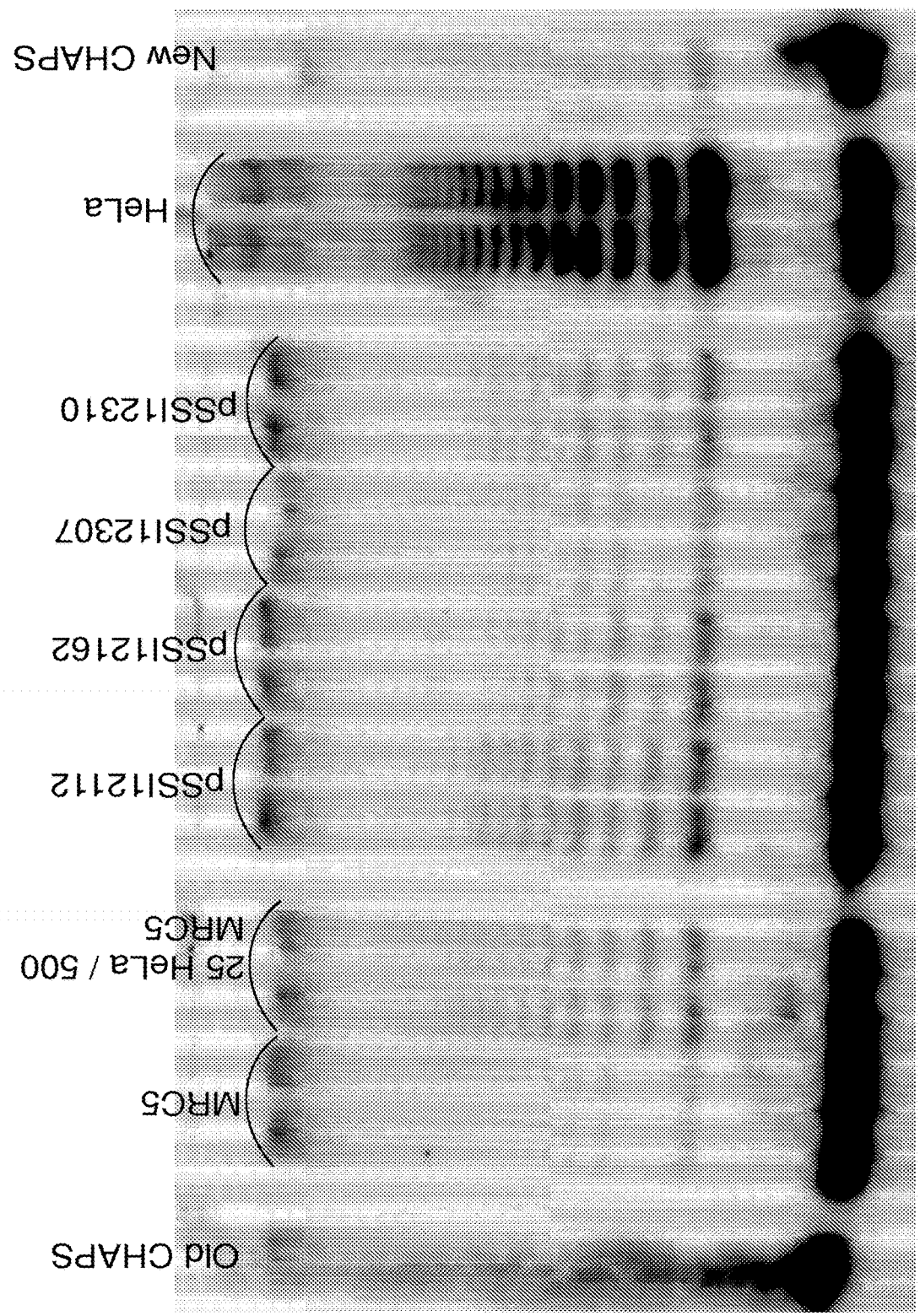
FIG. 1 depicts the results of a TRAP Assay using the vectors pSSI12112, pSSI12162, pSSI112307 and pSSI12310 where sample cells are collected at 7 days post BSD selection, 17 days post infection.

As summarized above, aspects of the invention include methods of treating an age-related disorder in a subject. Aspects of the methods include administering to the subject a nucleic acid vector including a coding sequence for telomerase reverse transcriptase (TERT). In some cases, the vector may include a coding sequence for telomerase RNA (TR). Gene therapy methods that utilize the subject vectors are also provided. Embodiments of the invention include compositions, e.g., nucleic acid vectors and kits, etc., that find use in the subject methods.

The subject methods may lead to increase the expression of telomerase reverse transcriptase and/or telomerase RNA when administered to adult mammals. Administration of the vectors to the subject may extend the lifespan of the subject (e.g., average or maximum lifespan), and may ameliorate one or more markers of ageing, including but not limited to epithelial barrier fitness, osteoporosis, glucose intolerance with insulin insensitivity, loss of memory, and neuromuscular degeneration associated with loss of neuromuscular coordination. The effect may be achieved without increasing the incidence of cancer (malignant neoplastic disease), as assessed by the number of spontaneous neoplasms evident among the population treated.

Before the present invention is described in greater detail, it is to be understood that this invention is not limited to particular embodiments described, as such may, of course, vary. It is also to be understood that the terminology used herein is for the purpose of describing particular embodiments only, and is not intended to be limiting, since the scope of the present invention will be limited only by the appended claims.

Where a range of values is provided, it is understood that each intervening value, to the tenth of the unit of the lower limit unless the context clearly dictates otherwise, between the upper and lower limit of that range and any other stated or intervening value in that stated range, is encompassed within the invention. The upper and lower limits of these smaller ranges may independently be included in the smaller ranges and are also encompassed within the invention, subject to any specifically excluded limit in the stated range. Where the stated range includes one or both of the limits, ranges excluding either or both of those included limits are also included in the invention.

Certain ranges are presented herein with numerical values being preceded by the term "about." The term "about" is used herein to provide literal support for the exact number that it precedes, as well as a number that is near to or approximately the number that the term precedes. In determining whether a number is near to or approximately a specifically recited number, the near or approximating unrecited number may be a number which, in the context in which it is presented, provides the substantial equivalent of the specifically recited number.

Unless defined otherwise, all technical and scientific terms used herein have the same meaning as commonly understood by one of ordinary skill in the art to which this invention belongs. Although any methods and materials similar or equivalent to those described herein can also be used in the practice or testing of the present invention, representative illustrative methods and materials are now described.

All publications and patents cited in this specification are herein incorporated by reference as if each individual publication or patent were specifically and individually indicated to be incorporated by reference and are incorporated herein by reference to disclose and describe the methods and/or materials in connection with which the publications are cited. The citation of any publication is for its disclosure prior to the filing date and should not be construed as an admission that the present invention is not entitled to antedate such publication by virtue of prior invention. Further, the dates of publication provided may be different from the actual publication dates which may need to be independently confirmed.

It is noted that, as used herein and in the appended claims, the singular forms "a", "an", and "the" include plural referents unless the context clearly dictates otherwise. It is further noted that the claims may be drafted to exclude any optional element. As such, this statement is intended to serve as antecedent basis for use of such exclusive terminology as "solely," "only" and the like in connection with the recitation of claim elements, or use of a "negative" limitation.

As will be apparent to those of skill in the art upon reading this disclosure, each of the individual embodiments described and illustrated herein has discrete components and features which may be readily separated from or combined with the features of any of the other several embodiments without departing from the scope or spirit of the present invention. Any recited method can be carried out in the order of events recited or in any other order which is logically possible.

Vectors

As summarized above, one aspect of the invention is a nucleic acid vector. Application of the subject vector to a subject, e.g. using any convenient method such as a gene therapy method, may result in expression of one or more coding sequences of interest in cells of the subject, to produce a biologically active product that may modulate a biological activity of the cell. In some cases, the vector is a nucleic acid vector comprising a coding sequence for telomerase reverse transcriptase (TERT). In some cases, the nucleic acid vector comprises a coding sequence for one or more telomerase components, such as TERT and telomerase RNA (TR). In some embodiments, the vector does not include a cancer suppressing sequence.

In some instances, the vector comprises a coding sequence for telomerase reverse transcriptase (TERT) suitable for use in gene therapy. Gene therapy vectors of interest include any kind of particle that comprises a polynucleotide fragment encoding the telomerase reverse transcriptase (TERT) protein, operably linked to a regulatory element such as a promoter, which allows the expression of a functional TERT protein demonstrating telomerase reverse transcriptase activity in the targeted cells. In some cases, TERT is encoded by the nucleic acid sequence as set forth in SEQ ID NO:1 of WO2012001170 or SEQ ID NO:3 of WO2012001170, or is an active fragment or functional equivalent of TERT. In some instances, the vector include a regulatory sequence which is a constitutive promoter such as the cytomegalovirus (CMV) promoter.

The TERT and/or TR sequence used in the gene therapy vector may be derived from the same species as the subject. Any convenient TERT and/or TR sequences, or fragments or functional equivalents thereof, may be utilized in the subject vectors, including sequences from any convenient animal, such as a primate, ungulate, cat, dog, or other domestic pet or domesticated mammal, rabbit, pig, horse, sheep, cow, or a human. For example, gene therapy in humans may be carried out using the human TERT sequence. In some embodiments, the TERT and/or TR sequence is not a murine sequence.

As used herein, "functional equivalent" refers to a nucleic acid molecule that encodes a polypeptide that has TERT activity or a polypeptide that has TERT activity. The functional equivalent may displays 50%, 60%, 70%, 80%, 90%, 95%, 98%, 99%, 100% or more activity compared to a parent TERT sequence. Functional equivalents may be artificial or naturally-occurring. For example, naturally-occurring variants of the TERT sequence in a population fall within the scope of functional equivalent. TERT sequences derived from other species also fall within the scope of the term "functional equivalent", e.g., a murine TERT sequence. In a particular embodiment, the functional equivalent is a nucleic acid with a nucleotide sequence having at least 75%, 80%, 85%, 90%, 95%, 96%, 97%, 98%, 99%, 99.5%, 99.9% identity to the parent sequence. In a further embodiment, the functional equivalent is a polypeptide with an amino acid sequence having at least 75%, 80%, 85%, 90%, 95%, 96%, 97%, 98%, 99%, 99.5%, 99.9% identity to a parent sequence. In the case of functional equivalents, sequence identity should be calculated along the entire length of the nucleic acid. Functional equivalents may contain one or more, e.g. 2, 3, 4, 5, 10, 15, 20, 30 or more, nucleotide insertions, deletions and/or substitutions when compared to a parent sequence.

The term "functional equivalent" also encompasses nucleic acid sequences that encode a TERT polypeptide with at least 75%, 80%, 85%, 90%, 95%, 96%, 97%, 98%, 99%, 99.5%, 99.9% sequence identity to the parent amino acid sequence, but that show little homology to the parent nucleic acid sequence because of the degeneracy of the genetic code.

As used herein, the term "active fragment" refers to a nucleic acid molecule that encodes a polypeptide that has TERT activity or polypeptide that has TERT activity, but which is a fragment of the nucleic acid as set forth in the parent polynucleotide sequence or the amino acid sequence as set forth in parent polypeptide sequence. An active fragment may be of any size provided that TERT activity is retained. A fragment will have at least 75%, 80%, 85%, 90%, 95%, 96%, 97%, 98%, 99%, 99.5%, 100% identity to the parent sequence along the length of the alignment between the shorter fragment and longer parent sequence.

Fusion proteins including these fragments can be comprised in the nucleic acid vectors needed to carry out the invention. For example, an additional 5, 10, 20, 30, 40, 50 or even 100 amino acid residues from the polypeptide sequence, or from a homologous sequence, may be included at either or both the C terminal and/or N terminus without prejudicing the ability of the polypeptide fragment to fold correctly and exhibit biological activity. Sequence identity may be calculated by any one of the various methods in the art, including for example BLAST (Altschul S F, Gish W, Miller W, Myers E W, Lipman D J (1990). "Basic local alignment search tool". J Mol Biol 215 (3): 403-410) and PASTA (Lipman, D J; Pearson, W R (1985). "Rapid and sensitive protein similarity searches". Science 227 (4693): 1435-41; http://fasta.bioch.virginia.edu/fasta www2/fasta list2.shtml) and variations on these alignment programs.

The vector may further include one or more regulatory sequences. Any convenient regulatory sequences or promoter sequences may be utilized in the subject vectors, e.g., as described herein. In some embodiments, the regulatory sequence that is operatively linked to the coding sequence (e.g., the TERT and/or TR sequence) is the cytomegalovirus promoter (CMV), although any other convenient regulatory sequences may be utilized.

Viral Vectors

Any convenient viruses may be utilized in delivering the vector of interest to the subject. Viruses of interest include, but are not limited to a retrovirus, an adenovirus, an adeno-associated virus (AAV), a herpes simplex virus and a lentivirus. Viral gene therapy vectors are well known in the art, see e.g., Heilbronn & Weger (2010) Handb Exp Pharmacal. 197:143-70. Vectors of interest include integrative and non-integrative vectors such as those based on retroviruses, adenoviruses (AdV), adeno-associated viruses (AAV), lentiviruses, pox viruses, alphaviruses, and herpes viruses.

In some cases, non-integrative viral vectors, such as AAV, may be utilized. In one aspect, non-integrative vectors do not cause any permanent genetic modification. The vectors may be targeted to adult tissues to avoid having the subjects under the effect of constitutive telomerase expression from early stages of development. In some instances, non-integrative vectors effectively incorporate a safety mechanism to avoid over-proliferation of TERT expressing cells. The cells may lose the vector (and, as a consequence, the telomerase expression) if they start proliferating quickly.

Non-integrative vectors of interest include those based on adenoviruses (AdV) such as gutless adenoviruses, adeno-associated viruses (AAV), integrase deficient lentiviruses, pox viruses, alphaviruses, and herpes viruses. In certain embodiments, the non-integrative vector used in the invention is an adeno-associated virus-based non-integrative vector, similar to natural adeno-associated virus particles. Examples of adena-associated virus-based non integrative vectors include vectors based on any AAV serotype, i.e. AAVI, AAV2, AAV3, AAV4, AAV5, AAV6, AAV7, AAV8, AAV9, AAVIO, AAVII and pseudotyped AAV. Vectors of interest include those capable of transducing a broad range of tissues at high efficiency, with poor immunogenicity and an excellent safety profile. In some cases, the vectors transduce post-mitotic cells and can sustain long-term gene expression (up to several years) both in small and large animal models of age-related disorders.

Methods

As summarized above, aspects of the invention include methods of administering a nucleic acid vector to a subject. As such, aspects of the invention include contacting the subject with a viral vector, e.g., as described above, under conditions by which expression of one or more telomerase components (such as TERT and/or TR) in the subject results in a beneficial effect on one or more aspects of the subject's health, including increased longevity, delayed osteoporosis, improved epithelial barrier fitness, improved glucose tolerance, improved memory function, and improved neuromuscular coordination. In some cases, the subject did not develop increased incidence of cancer, illustrating the safety of this type of strategy.

In gene therapy methods, genes are directly inserted into cells affected by an age-related condition so that the function of the cells is normalized by expressing the inserted genes. The gene therapy methods may be used to prevent various diseases or age-related conditions or to reinforce treatment by inserting a specific gene into a body cell and granting a new function to the body cell. One aspect in the treatment of such conditions using gene therapy is that the inserted gene be successfully delivered to the nucleus of the target cell and that the gene be expressed strongly. The gene enters the target cell through endocytosis and is transported into the nucleus to be expressed. The gene can be inserted using a carrier such as a liposome since most DNAs are destroyed when entering the cell. However, most of the liposomes are also destroyed when entering the nucleus, thereby decreasing the transporting efficiency. A virus capable of infecting a human can be treated using gene therapy because the virus effectively inserts exogeneous genes into the human body. Specifically, the gene can effectively be transported and expressed by inserting the gene for the gene therapy into the DNA of the virus using gene recombination and infecting the subject (e.g., a human) with the recombinant virus, which can be mass produced in vitro. In some cases, an adenovirus can be effectively used for the gene therapy by using a mechanism of transporting the gene into the nucleus of the target cell with a high efficiency. In addition, retroviruses are being used in many internationally permissible clinical trials (Wiley—The Journal of Gene Medicine Website: http//www.wiley.co.uk/genetherapy). Retroviruses are effective for gene therapy when inserted into cell chromosomal DNA to allow long term expression of the desired protein.

In certain instances, the expression of the TERT and/or TR following gene therapy according to the invention persists for a time of one or more weeks, such as one or more months, e.g., several months to several years.

When treating specific age related disorders, it is advantageous to target the treatment to the effected tissues. The serotype of the capsid protein of the gene therapy vector may thus be selected based on the desired site of gene therapy, e.g., skeletal muscle tissue for treating neuromuscular coordination.

Any convenient methods may be employed. Methods and vectors of interest that may be adapted for use in the subject invention include, but are not limited to the methods and vectors of WO 2012/001170 and Vidale et al. "The catalytic and the RNA subunits of human telomerase are required to immortalize equid primary fibroblasts." Chromosoma. 2012 Jul. 14. Epub, the disclosures of which are herein incorporated by reference.

In some embodiments, the method of treatment is a gene therapy method and/or the nucleic acid vector used is a gene therapy vector. Gene therapy methods and vectors are well known in the art and generally include delivering a nucleic acid encoding a therapeutically active protein to a subject. The nucleic acid may be delivered in a number of ways including delivering naked DNA such as plasmid or minicircles, the use of liposomes or cationic polymers or other engineered nano-particles containing the nucleic acid, or viral vectors that encapsidate the nucleic acid.

In a further embodiment, the gene therapy is achieved using stable transformation of organisms with an inducible expression system. In certain embodiments, this aspect of the invention does not extend to human subjects. Expression of TERT or TR can be induced at a later date following transformation, for example, once the subject is an adult or an aged adult, or begins to show signs of age-related disorders. Suitable inducible expression systems are known in the art and include the CRE-LOX recombinase based system and the tetracycline-regulated system.

In some embodiments, the present invention is limited to the expression of TERT an/or TR in adult or aged subjects. In certain embodiments, the methods and vectors are utilized with post-mitotic cells within the subjects, and avoid any increased incidence of cancer.

Any convenient subjects may be treated according to the subject methods. The subject may be an adult animal, such as an adult mammal. The mammal may be a primate, ungulate, cat, dog, domestic pet or domesticated mammal. In some cases, the mammal may be a rabbit, pig, horse, sheep, cow, cat or dog, or a human. In certain embodiments the subject is not a murine mammal. An adult subject treated according to the invention may be aged. The term "aged" is applied to an individual who is older than the period of life during which the individuals of its species are generally healthy and free of chronic illness. According to the present application, an "adult" should be a fully developed individual who has attained reproductive ability, is fertile, or who evidences secondary sex characteristics. As used herein, the term adult when applied to humans, for example, describes early adulthood commencing at around 20 years of age and extending to 39; middle adulthood (40 to 59) and late adulthood (60+). As a comparison, a one year old mouse can be considered to be approximately equivalent in age to a 45 year old human. A 2 year old mouse can be considered to be approximately equivalent to an 80 year old human.

The particular protocol that is employed may vary. Administration of the vectors may be achieved using any convenient protocol. Vectors as described above (e.g., retroviral vectors and lentiviral vectors) may be administered in vivo to subjects by any convenient route. The term "administration" refers to the route of introduction of a formulated vector into the body. For example, administration may be intravenous, intramuscular, topical, oral, or by gene gun or hypospray instrumentation. Thus, administration can be direct to a target tissue or through systemic delivery. Administration directly to the target tissue can involve needle injection, hypospray, electroporation, or the gene gun. See, e.g., WO 93/18759, hereby incorporated by reference herein. Alternatively, vectors of the invention can be administered ex vivo or in vitro to cells or tissues using any convenient transfection techniques.

The vectors of the invention can also be transduced into host cells, including but not limited to, embryonic stem cells, somatic stem cells, or progenitor cells. Examples of progenitor host cells which can be transduced by the vectors of the invention include precursors of erythrocytes and hematopoietic stem cells. In another embodiment, the host cell is an erythrocyte. Transduced host cells can be used as a method of achieving erythroid-specific expression of the gene of interest in the treatment of hemoglobinopathies.

In some embodiments, the method does not include concomitant use of a cancer suppressor.

The step of facilitating the production of infectious viral particles in the cells may be carried out using conventional techniques, such as standard cell culture growth techniques. If desired by the skilled artisan, lentiviral stock solutions may be prepared using the vectors and methods of the present invention. Methods of preparing viral stock solutions are known in the art and are illustrated by, e.g., Y. Soneoka et al. (1995) Nucl. Acids Res. 23:628-633, and N. R. Landau et al. (1992) J. Virol. 66:5110-5113. In a method of producing a stock solution in the present invention, lentiviral-permissive cells (referred to herein as producer cells) are transfected with the vector system of the present invention. The cells are then grown under suitable cell culture conditions, and the lentiviral particles collected from either the cells themselves or from the cell media as described above. Suitable producer cell lines include, but are not limited to, the human embryonic kidney cell line 293, the equine dermis cell line NBL-6, and the canine fetal thymus cell line Cf2TH.

The step of collecting the infectious virus particles also can be carried out using conventional techniques. For example, the infectious particles can be collected by cell lysis, or collection of the supernatant of the cell culture, as is known in the art. Optionally, the collected virus particles may be purified if desired. Suitable purification techniques are well known to those skilled in the art.

Other methods relating to the use of viral vectors in gene therapy can be found in, e.g., Kay, M. A. (1997) Chest 111(6 Supp.): 138S-142S; Ferry, N. and Heard, J. M. (1998) Hum. Gene Ther. 9:1975-81; Shiratory, Y. et al. (1999) Liver 19:265-74; Oka, K. et al. (2000) Curr. Opin. Lipidol. 11:179-86; Thule, P. M. and Liu, J. M. (2000) Gene Ther. 7:1744-52; Yang, N. S. (1992) Crit. Rev. Biotechnol. 12:335-56; Alt, M. (1995) J. Hepatol. 23:746-58; Brody, S. L. and Crystal, R. G. (1994) Ann. N.Y. Acad. Sci. 716:90-101; Strayer, D. S. (1999) Expert Opin. Investig. Drugs 8:2159-2172; Smith-Arica, J. R. and Bartlett, J. S. (2001) Curr. Cardiol. Rep. 3:43-49; and Lee, H. C. et al. (2000) Nature 408:483-8.

As used herein "pharmaceutically acceptable carrier" includes any and all solvents, dispersion media, coatings, antibacterial and antifungal agents, isotonic and absorption delaying agents, and the like that are physiologically compatible. In one embodiment, the carrier is suitable for parenteral administration. Preferably, the carrier is suitable for administration directly into an affected joint. The carrier can be suitable for intravenous, intraperitoneal or intramuscular administration. Pharmaceutically acceptable carriers include sterile aqueous solutions or dispersions and sterile powders for the extemporaneous preparation of sterile injectable solutions or dispersion. The use of such media and agents for pharmaceutically active substances is well known in the art. Except insofar as any conventional media or agent is incompatible with the active compound, use thereof in the pharmaceutical compositions of the invention is contemplated. Supplementary active compounds can also be incorporated into the compositions.

Another aspect of the invention pertains to pharmaceutical compositions of the vectors of the invention. In one embodiment, the composition includes a vector in a therapeutically effective amount sufficient to treat or prevent (e.g. ameliorate one or more age-related conditions), and a pharmaceutically acceptable carrier. A "therapeutically effective amount" refers to an amount effective, at dosages and for periods of time necessary, to achieve the desired therapeutic result, such as treatment or amelioration of an age-related condition. A therapeutically effective amount of vector may vary according to factors such as the disease state, age, sex, and weight of the individual, and the ability of the viral vector to elicit a desired response in the individual. Dosage regimens may be adjusted to provide the optimum therapeutic response. A therapeutically effective amount is also one in which any toxic or detrimental effects of the viral vector are outweighed by the therapeutically beneficial effects. The potential toxicity of the viral vectors of the invention can be assayed using cell-based assays or art recognized animal models and a therapeutically effective modulator can be selected which does not exhibit significant toxicity. In a preferred embodiment, a therapeutically effective amount of a viral vector is sufficient to treat or ameliorate one or more age-related conditions in as subject.

Sterile injectable solutions can be prepared by incorporating viral vector in the required amount in an appropriate solvent with one or a combination of ingredients enumerated above, as required, followed by filtered sterilization. Generally, dispersions are prepared by incorporating the active compound into a sterile vehicle which contains a basic dispersion medium and the required other ingredients from those enumerated above. In the case of sterile powders for the preparation of sterile injectable solutions, the methods of preparation are vacuum drying and freeze-drying which yields a powder of the active ingredient plus any additional desired ingredient from a previously sterile-filtered solution thereof.

It is to be noted that dosage values may vary with the severity of the condition to be ameliorated. It is to be further understood that for any particular subject, specific dosage regimens can be adjusted over time according to the individual need and the professional judgment of the person administering or supervising the administration of the compositions, and that dosage ranges set forth herein are exemplary only and are not intended to limit the scope or practice of the claimed composition.

The amount of viral vector in the composition may vary according to factors such as the disease state, age, sex, and weight of the individual. Dosage regimens may be adjusted to provide the optimum therapeutic response. For example, a single bolus may be administered, several divided doses may be administered over time or the dose may be proportionally reduced or increased as indicated by the exigencies of the therapeutic situation. It is especially advantageous to formulate parenteral compositions in dosage unit form for ease of administration and uniformity of dosage. Dosage unit form as used herein refers to physically discrete units suited as unitary dosages for the mammalian subjects to be treated; each unit containing a predetermined quantity of active compound calculated to produce the desired therapeutic effect in association with the required pharmaceutical carrier. The specification for the dosage unit forms of the invention are dictated by and directly dependent on (a) the unique characteristics of the active compound and the particular therapeutic effect to be achieved, and (b) the limitations inherent in the art of compounding such an active compound for the treatment of sensitivity in individuals.

In Vitro Methods

Also included are in vitro methods, where the subject vectors, e.g., as described above are contacted with a sample. The particular protocol that is employed may vary, e.g., depending on the sample. For in vitro protocols, contact of the vector with the sample may be achieved using any convenient protocol. In some instances, the sample includes cells that are maintained in a suitable culture medium, and the vector is introduced into the culture medium. Depending upon the nature of the vector (e.g., a viral vector), the response desired, the manner of contacting or administration, the number of cells present, various protocols may be employed. The term "sample" as used herein relates to a material or mixture of materials, typically, although not necessarily, in fluid form, containing one or more components of interest.

Utility

The vectors and methods of the invention, e.g., as described above, find use in a variety of applications. Applications of interest include, but are not limited to: research applications and therapeutic applications. Methods of the invention find use in a variety of different applications including any convenient application where the subject is experiencing one or more age-related conditions. In some cases, age-related disorders or conditions that may be modulated or ameliorated using the subject vectors and methods include, but are not limited to, osteoporosis, arthrosis, glucose intolerance, insulin resistant, reduced heart, circulatory and/or lung function, cardiovascular disease, loss of memory, loss of neuromuscular coordination and decrease of longevity, or combinations thereof.

The subject vectors and methods find use in a variety of research applications. The subject vectors and methods may be used to analyze the role of telomerase various biological processes including age-related disorders and conditions.

The subject vectors and methods find use in a variety of therapeutic applications. Therapeutic applications of interest include those applications in which the subject is suffering from one or more age-related disorders or conditions. As such, the subject vectors find use in the treatment of a variety of different age-related conditions in various subjects, and may lead to an extended lifespan. For example, the subject vectors and methods may find use in regulated gene therapy.

Extended lifespan may be an increase in the maximum lifespan possible for any particular species of subject. Extended lifespan may be an increase in the average lifespan of an individual of that species who reaches adulthood. Thus, extended lifespan may be a 5%, 10%, 15%, 20% or more increase in maximum lifespan and/or a 5%, 10%, 15%, 20% or more increase in average lifespan.

The application of the invention extends the period of time for which an individual is generally healthy and free of chronic illness and/or the invention ameliorates disorders that appear often in aged and ageing adult population, including reduced epithelial barrier fitness, osteoporosis, glucose intolerance and neuromuscular degeneration associated with loss of neuromuscular coordination. These are well established indicators of ageing progression.

Accordingly, the invention has beneficial effects in at least one of the following group: reducing the incidence of cancer, on delaying and/or ameliorating osteoporosis, improving epithelial barrier fitness, improving glucose tolerance, improving memory function, and improving neuromuscular coordination. The amelioration of age-related disorders provided by the invention can be as a result of reduction of symptoms in an affected subject or a reduction of incidence of the disease or disorder in a population as compared to an untreated population. The application of gene therapy according to the invention has the effect of treating and/or preventing various age-related conditions and diseases, as assessed by particular markers and disorders of ageing. In a further aspect, therefore, the invention refers to a gene therapy method or the used of a nucleic acid vector as described above, for use in the treatment or prevention in a subject of at least a disorder or marker of ageing that is selected from the group of reduced epithelial barrier fitness, osteoporosis, arthrosis, glucose intolerance, insulin resistance, loss of memory, loss of neuromuscular coordination, increase in cardiovascular disease, decrease in heart, circulatory or lung function and decrease in longevity, or combinations thereof. The gene therapy ameliorates at least one marker of ageing, selected for example, from the group of reduced epithelial barrier fitness, osteoporosis, arthrosis, glucose intolerance, insulin resistance, cardiovascular disease, reduced heart and circulatory function, reduced lung function, loss of memory, loss of neuromuscular coordination or decrease of longevity or combinations thereof.

Kits

Aspects of the invention further include kits, where the kits include one or more components employed in methods of the invention, e.g., vectors, as described herein. In some embodiments, the subject kit includes a vector (as described herein), and one or more components selected from a promoter, a virus, a cell, and a buffer. Any of the components described herein may be provided in the kits, e.g., cells, constructs (e.g., vectors) encoding for TERT and/or TR, components suitable for use in expression systems (e.g., cells, cloning vectors, multiple cloning sites (MSC), bi-directional promoters, an internal ribosome entry site (IRES), etc.), etc. A variety of components suitable for use in making and using constructs, cloning vectors and expression systems may find use in the subject kits. Kits may also include tubes, buffers, etc., and instructions for use. The various reagent components of the kits may be present in separate containers, or some or all of them may be pre-combined into a reagent mixture in a single container, as desired.

In addition to the above components, the subject kits may further include (in certain embodiments) instructions for practicing the subject methods. These instructions may be present in the subject kits in a variety of forms, one or more of which may be present in the kit. One form in which these instructions may be present is as printed information on a suitable medium or substrate, e.g., a piece or pieces of paper on which the information is printed, in the packaging of the kit, in a package insert, etc. Yet another form of these instructions is a computer readable medium, e.g., diskette, compact disk (CD), Hard Drive etc., on which the information has been recorded. Yet another form of these instructions that may be present is a website address which may be used via the internet to access the information at a removed site.

Aspects of the invention include providing a virus particle that includes a nucleic acid vector, e.g., as described above. Any convenient virus particles may be utilized, and include viral vector particles described above.

Aspects of the invention include providing a cell that includes a nucleic acid vector. The cell that is provided with the vector of interest may vary depending on the specific application being performed. Target cells of interest include eukaryotic cells, e.g., animal cells, where specific types of animal cells include, but are not limited to: insect, worm or mammalian cells. Various mammalian cells may be used, including, by way of example, equine, bovine, ovine, canine, feline, murine, non-human primate and human cells. Among the various species, various types of cells may be used, such as hematopoietic, neural, glial, mesenchymal, cutaneous, mucosal, stromal, muscle (including smooth muscle cells), spleen, reticulo-endothelial, epithelial, endothelial, hepatic, kidney, gastrointestinal, pulmonary, fibroblast, and other cell types. Hematopoietic cells of interest include any of the nucleated cells which may be involved with the erythroid, lymphoid or myelomonocytic lineages, as well as myoblasts and fibroblasts. Also of interest are stem and progenitor cells, such as hematopoietic, neural, stromal, muscle, hepatic, pulmonary, gastrointestinal and mesenchymal stem cells, such as ES cells, epi-ES cells and induced pluripotent stem cells (iPS cells).

The following examples are put forth so as to provide those of ordinary skill in the art with a complete disclosure and description of how to make and use the present invention, and are not intended to limit the scope of what the inventors regard as their invention nor are they intended to represent that the experiments below are all or the only experiments performed. Efforts have been made to ensure accuracy with respect to numbers used (e.g. amounts, temperature, etc.) but some experimental errors and deviations should be accounted for. Unless indicated otherwise, parts are parts by weight, molecular weight is weight average molecular weight, temperature is in degrees Centigrade, and pressure is at or near atmospheric.

EXPERIMENTAL

Construction of Vectors
  pSSI14342: Adeno vector containing hTR and hTERT was constructed.
LITR-U1-hTR-CMV-hTERT-SV40pA-RITR
Region base locations:
Adeno RITR: 2928-3030
U1 promoter: 6459-6668
hTR: 6850-7300
U1-3'box: 7458-7472
CMV promoter: 7485-8073
Kozak: 8082-8098
hTERT: 8087-11482
SV40pA: 11558-11679
Adeno LITR: 5973-6075
  pSSI10902: Lentiviral vector pSSI10902 was constructed and contains hTERT, Puro gene (for selection of infected cells) and AmCyan gene (a fluorescent protein for color). In pSSI10902, hTERT is expressed using the CMV promoter, Puro gene is expressed using the SV40 promoter, and AmCyan gene is expressed using the CMV promoter. Below is shown the schematic for the pSSI10902 expression cassette. The sequence of this entire vector is also provided (SEQ ID NO: 2).
pSSI10902: 5'-LTR-CMV-hTERT-SV40-Puro-CMV-AmCyan-LTR-3'
Region base locations:
5' LTR: 230-410
CMV promoter: 1883-2374
Kozak: 2627-2643
hTERT: 2632-6027
SV40 promoter: 6053-6286
CMV promoter: 7242-7830
AmCyan: 7891-8577
3' LTR: 9315-9495
  pSSI12112: The lentiviral vector pSSI12112 was constructed as a dual vector containing both hTR and hTERT in the same vector. hTR is expressed using the U1 promoter and hTERT is expressed using the CMV promoter. Note: this plasmid also contains the BSD gene being expressed by the PGK promoter which allows selection for cells infected with the lentivirus created using this plasmid. Below is shown a schematic of the expression cassette for pSSI112112. The sequence of this entire vector is also attached (SEQ ID NO:3).
pSSI12112: 5'-LTR-U1-hTR-PGK-BSD-CMV-hTERT-LTR-3'
Region base locations:
5' LTR: 230-410
U1 promoter: 1876-2085
hTR: 2267-2717
U1-3'box: 2875-2889
PGK promoter: 2916-3421
BSD: 3499-3894
CMV promoter: 4023-4611
Kozak: 4620-4636
hTERT: 4625-8020
3' LTR: 8200-8380

Further vectors were constructed and tested as described herein.
pSSI12112=LTR-U1-hTR-PGK-BSD-CMV-TSS-hTERT-LTR
pSSI12162=LTR-U1-hTR-PGK-BSD-CMV-TSS-nonh-TERT-LTR
pSSI12307=LTR-PGK-BSD-CMV-TSS-hTERT-LTR
pSSI12310=LTR-PGK-BSD-CMV-TSS-nonhTERT-LTR The viral vectors are tested in vitro or in vivo using any convenient methods. Methods of interest that are adapted for use in testing the viral vectors described herein include those methods described by WO 2012/001170 and Vidale et al. "The catalytic and the RNA subunits of human telomerase are required to immortalize equid primary fibroblasts." Chromosoma. 2012 Jul. 14. Epub. Project 2273 pSSI12112 (hTR+hTERT) was tested in MRC5 cells. At 7 days post BSD selection, the TRAP activity from pSSI12112 is slightly stronger than the other 3 test samples (pSSI12162 (hTR+non-functional hTERT), pSSI12307 (hTERT), and pSSI12310 (non-functional hTERT)). At 14 days post selection, the pSSI12112 TRAP activity is less than the other 3 samples and eventually diminishes to no TRAP signal at 21 days post BSD selection.

FIG. 1 depicts the results of a TRAP Assay using the vectors pSSI12112, pSSI12162, pSSI12307 and pSSI12310 where sample cells are collected at 7 days post BSD selection, 17 days post infection.

Figure 2:
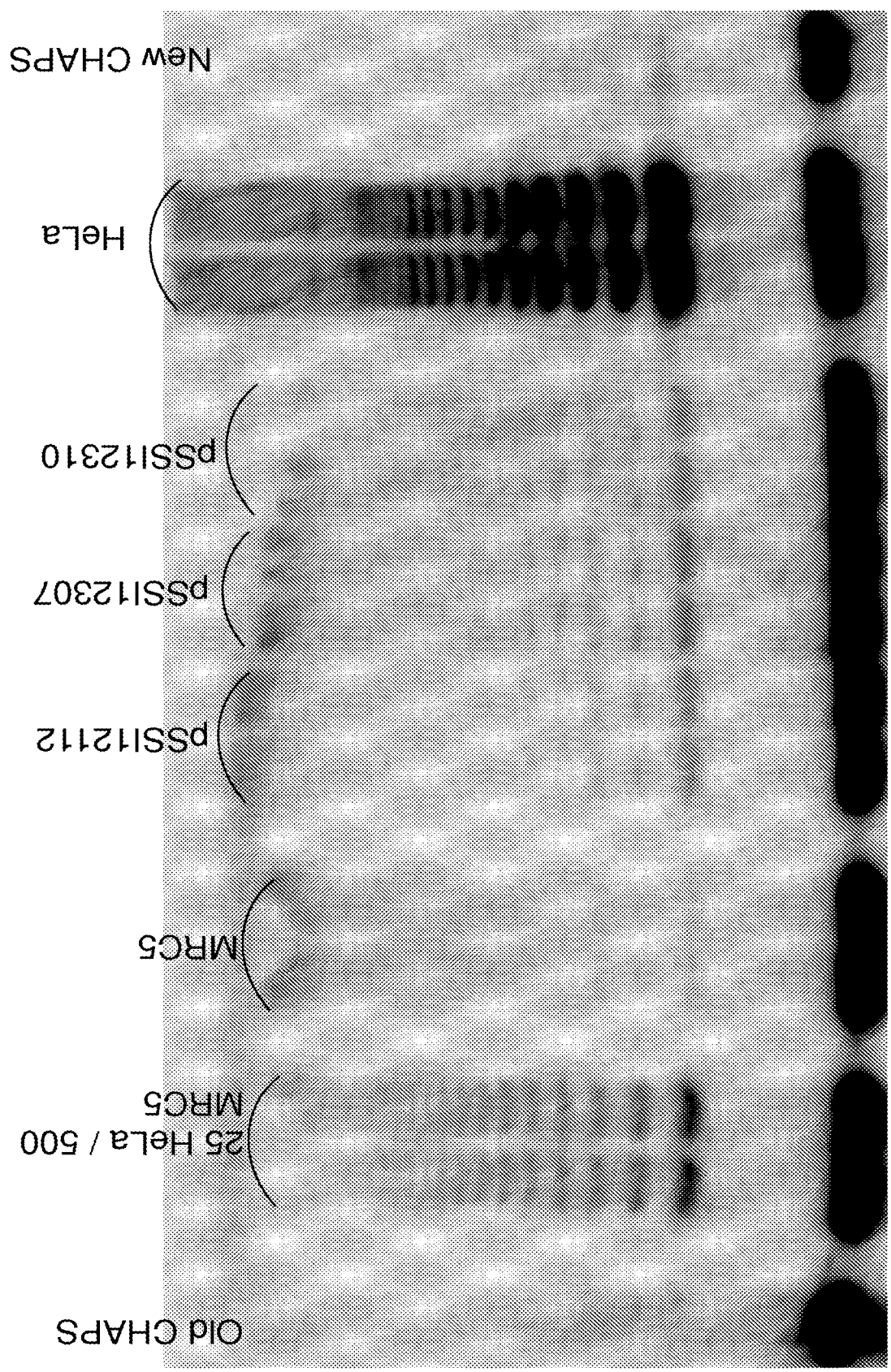
FIG. 2 depicts the results of a TRAP Assay using the vectors pSSI12112, pSSI12307 and pSSI12310 where sample cells are collected at 14 days post BSD selection, 24 days post infection.

FIG. 2 depicts the results of a TRAP Assay using the vectors pSSI12112, pSSI12307 and pSSI12310 where sample cells are collected at 14 days post BSD selection, 24 days post infection.

Figure 3:
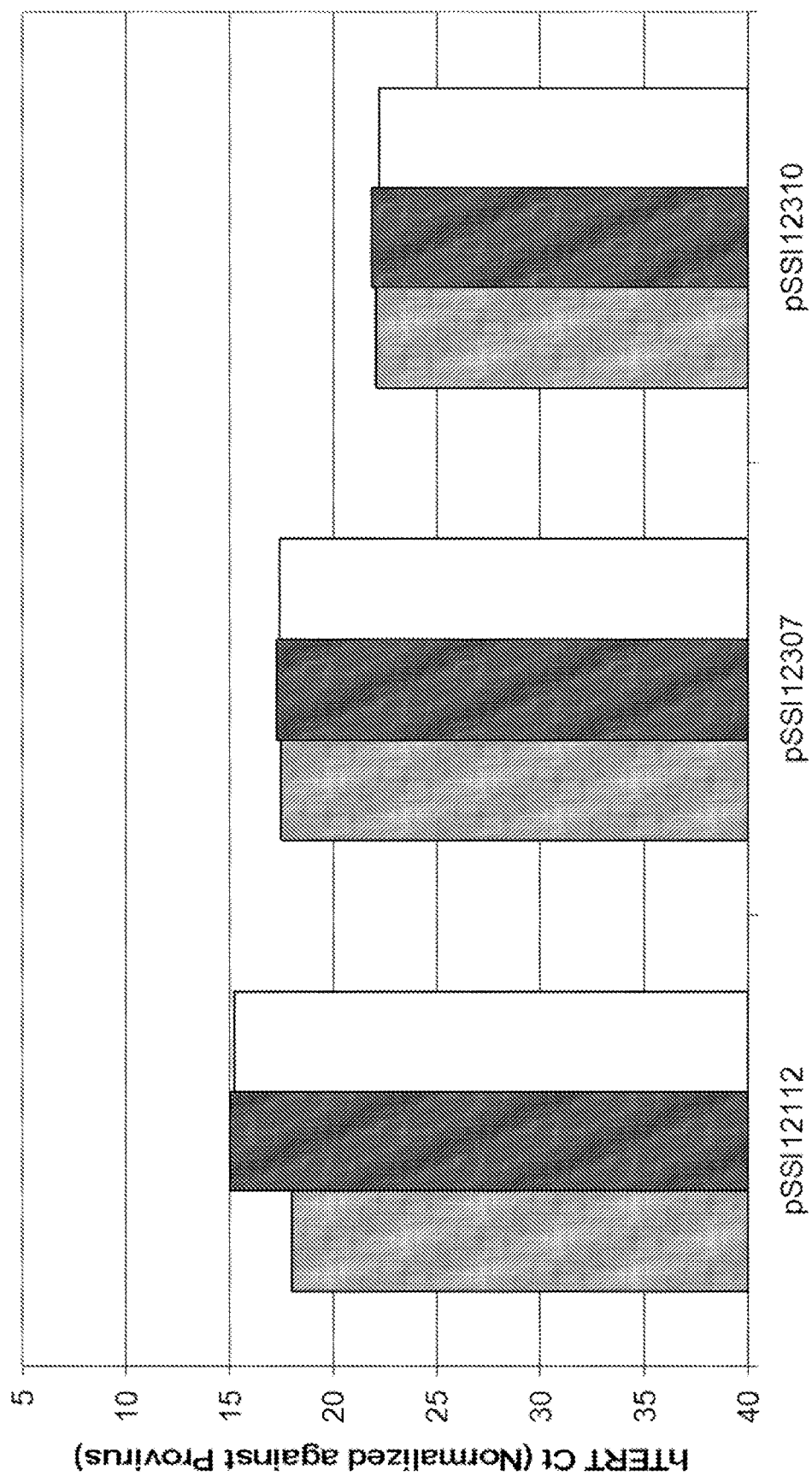
FIG. 3 illustrates RT-PCR results for hTERT Ct (normalized against provirus) using the vectors pSSI12112, pSSI112307 and pSSI12310 where sample cells are collected at 14 days post BSD selection, 24 days post infection.

FIG. 3 illustrates RT-PCR results for hTERT Ct (normalized against provirus) using the vectors pSSI12112, pSSI12307 and pSSI12310 where sample cells are collected at 14 days post BSD selection, 24 days post infection.

Figure 4:
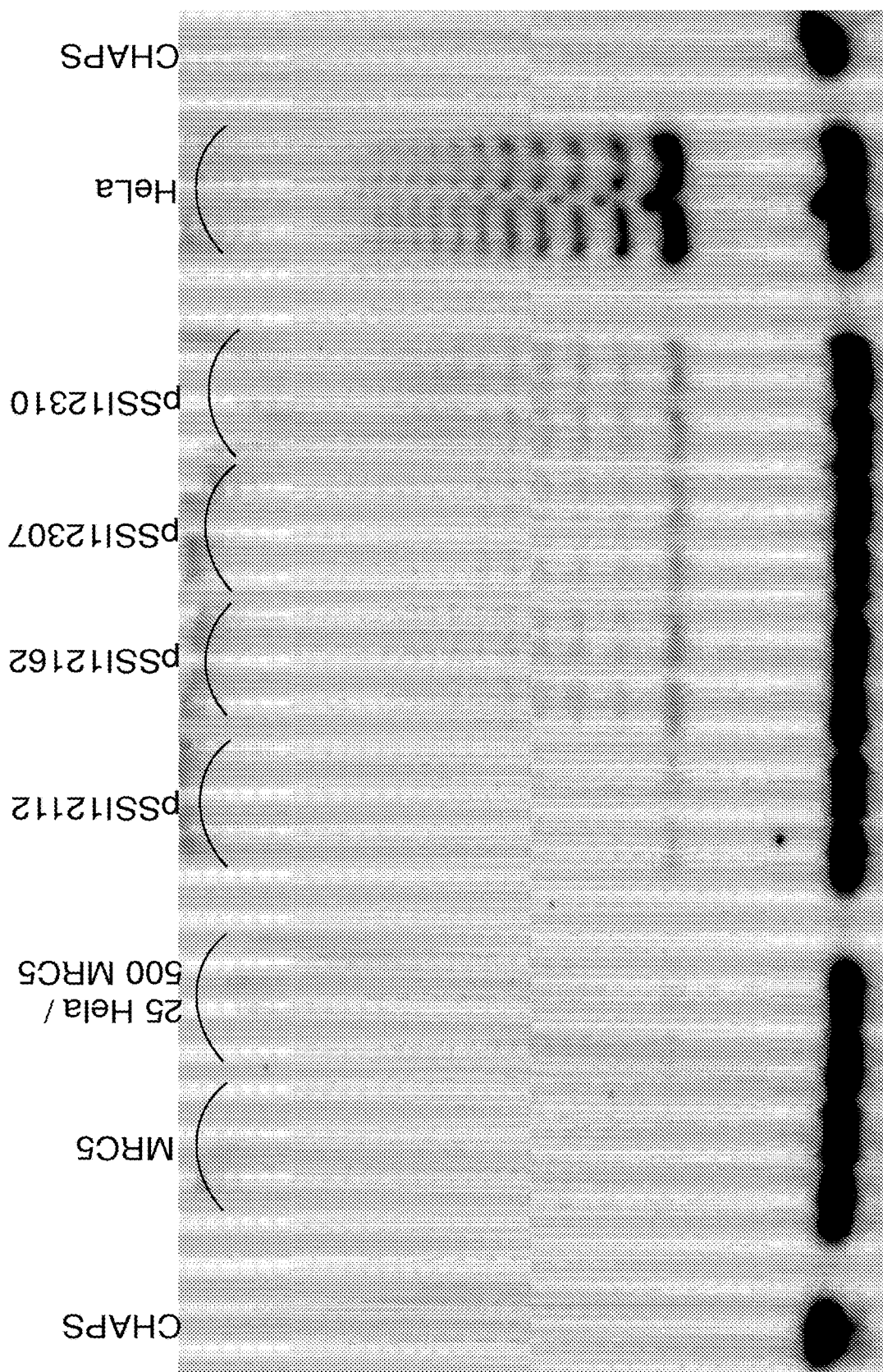
FIG. 4 depicts the results of a TRAP Assay using the vectors pSSI12112, pSSI12162, pSSI12307 and pSSI12310 where sample cells are collected at 21 days post BSD selection, 31 days post infection.

FIG. 4 depicts the results of a TRAP Assay using the vectors pSSI12112, pSSI12162, pSSI112307 and pSSI12310 where sample cells are collected at 21 days post BSD selection, 31 days post infection.

Figure 5:
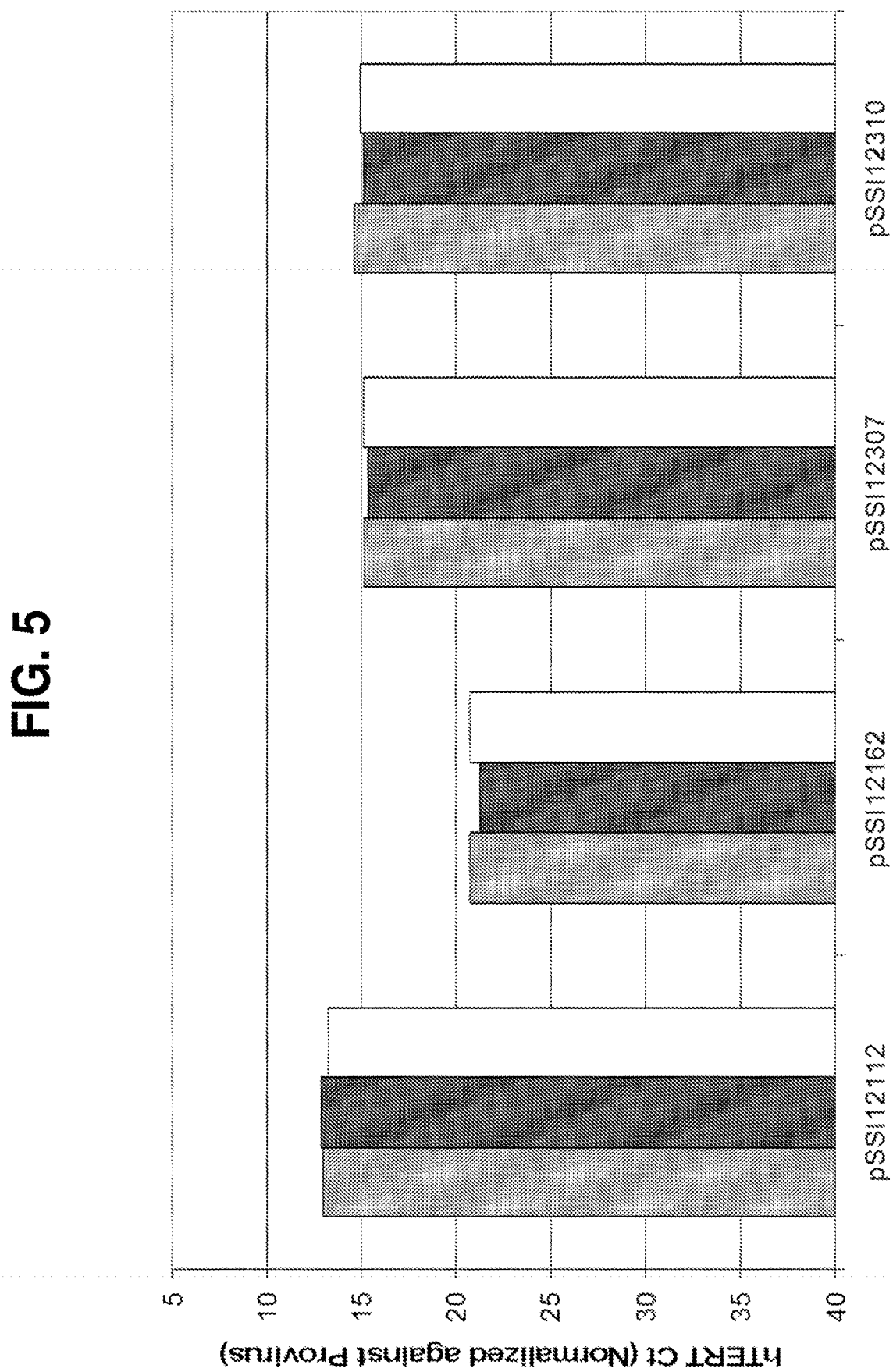
FIG. 5 illustrates RT-PCR results for hTERT Ct (normalized against provirus) using the vectors pSSI12112, pSSI112162, pSSI112307 and pSSI12310 where sample cells are collected at 14 days post BSD selection, 24 days post infection.

FIG. 5 illustrates RT-PCR results for hTERT Ct (normalized against provirus) using the vectors pSSI12112, pSSI12162, pSSI12307 and pSSI12310 where sample cells are collected at 14 days post BSD selection, 24 days post infection.

Figure 6:
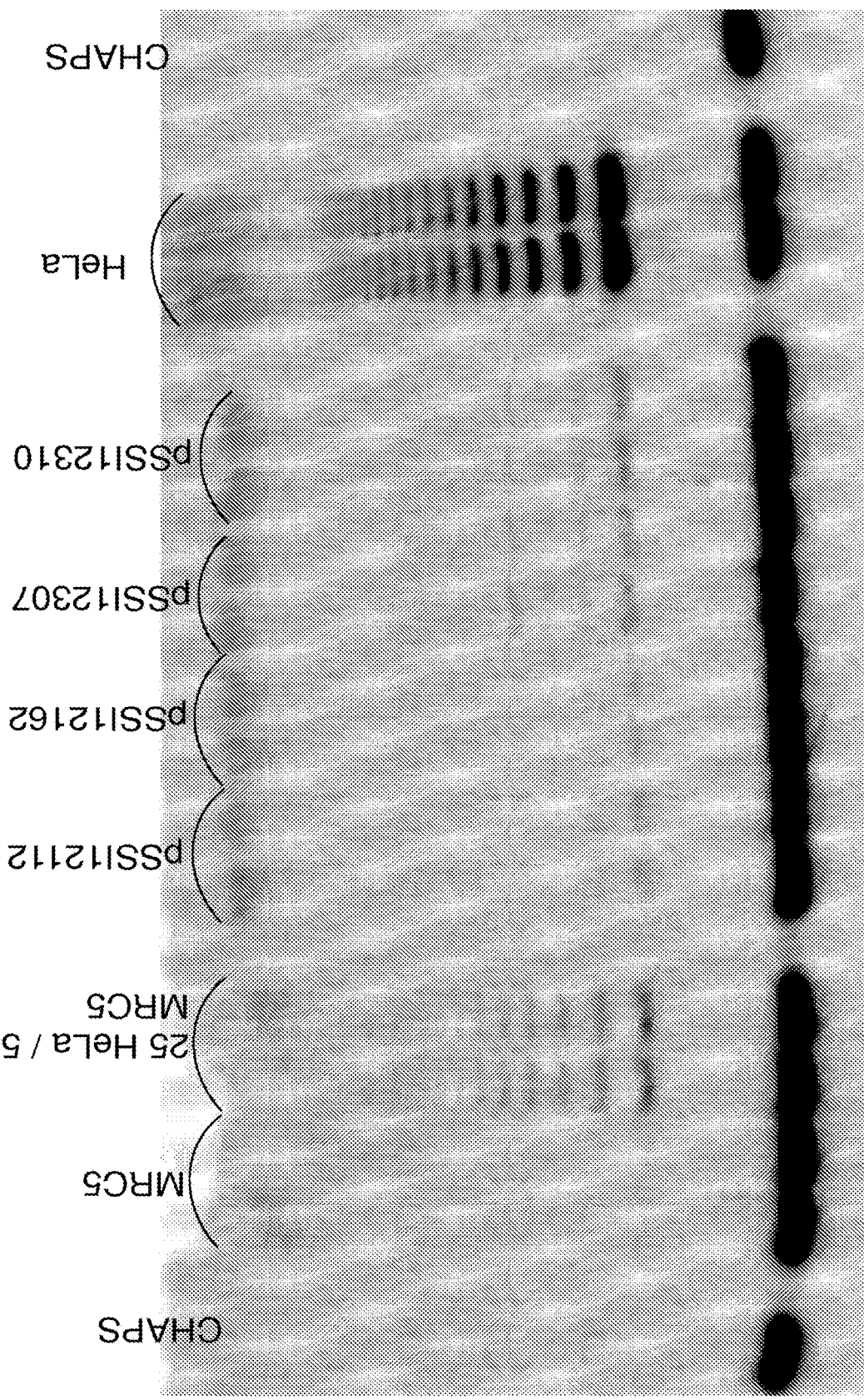
FIG. 6 depicts the results of a TRAP Assay using the vectors pSSI12112, pSSI12162, pSSI12307 and pSSI112310 where sample cells are collected at 49 days post BSD selection, 59 days post infection.

FIG. 6 depicts the results of a TRAP Assay using the vectors pSSI12112, pSSI12162, pSSI12307 and pSSI12310 where sample cells are collected at 49 days post BSD selection, 59 days post infection.

Figure 7:
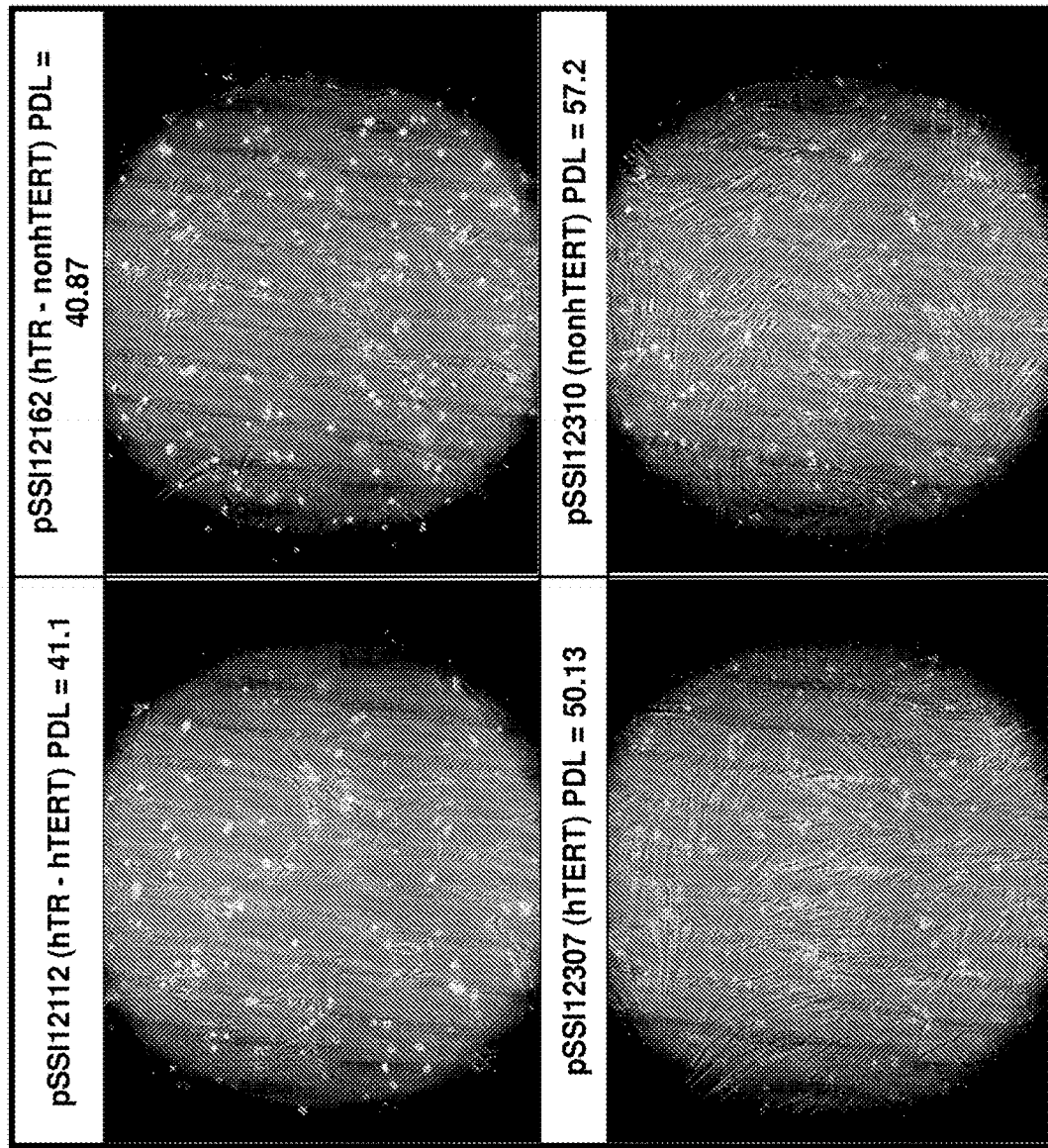
FIG. 7 depicts images comparing cell growth of cells that were maintained in 1.5 ug/ml BSD for 55 days post selection using the vectors pSSI112112, pSSI12162, pSSI12307 and pSSI12310.

FIG. 7 depicts images comparing cell growth of cells that were maintained in 1.5 ug/ml BSD for 55 days post selection using the vectors pSSI12112, pSSI12162, pSSI12307 and pSSI12310.

```
pSSI14342 (SEQ ID NO: 1)
TCACAGAACCCTAGTATTCAACCTGCCACCTCCCTCCCAACACACAGAGTACACAGTCCTTTCTC

CCCGGCTGGCCTTAAAAAGCATCATATCATGGGTAACAGACATATTCTTAGGTGTTATATTCCACA

CGGTTTCCTGTCGAGCCAAACGCTCATCAAGTGATATTAATAAACTCCCCGGGCAGCTCACTTAA

GTTCATGTCGCTGTCCAGCTGCTGAGCCACAGGCTGCTGTCCAACTTGCGGTTGCTTAACGGGC

GGCGAAGGAGAAGTCCACGCCTACATGGGGGGAGAGTCATAATCGTGCATCAGGATAGGGCGG

TGGTGCTGCAGCAGCGCGCGAATAAACTGCTGCCGCCGCCGCTCCGTCCTGCAGGAATACAACA

TGGCAGTGGTCTCCTCAGCGATGATTCGCACCGCCCGCAGCATAAGGCGCTTGTCCTCCGGGCA

CAGCAGCGCACCCTGATCTCACTTAAATCAGCACAGTAACTGCAGCACAGCACCACAATATTGTT

CAAAATCCCACAGTGCAAGGCGCTGTATCCAAAGCTCATGGCGGGGACCACAGAACCCACGTGG

CCATCATACCACAAGCGCAGGTAGATTAAGTGGCGACCCCTCATAAACACGCTGGACATAAACAT

TACCTCTTTTGGCATGTTGTAATTCACCACCTCCCGGTACCATATAAACCTCTGATTAAACATGGC

GCCATCCACCACCATCCTAAACCAGCTGGCCAAAACCTGCCCCGCCGGGNTATACACTGCAGGG

AACCGGGACTTGGACAATGACAAGTGGGAGAGCCCAGGACTCGTAACCATGGATCATCATGCTC

GTCATGATATCAATGTTGGCACAACACAGGCACACGTGCATACACTTCCTCAGGATTACAAGCTC

CTCCCGCGTTAGAACCATATCCCAGGGAACAACCCATTCCTGAATCAGCGTAAATCCCACACTGC

AGGGAAGACCTCGCACGTAACTCACGTTGTGCATTGTCAAAGTGTTACATTCGGGCAGCAGCGG

ATGATCCTCCAGTATGGTAGCGCGGGTTTCTGTCTCAAAAGGAGGTAGACGATCCCTACTGTACG

GAGTGCGCCGAGACAACCGAGATCGTGTTGGTCGTAGTGTCATGCCAAATGGAACGCCGGACGT

AGTCATATTTCCTGAAGCAAAACCAGGTGCGGGCGTGACAAACAGATCTGCGTCTCCGGTCTCG

CCGCTTAGATCGCTCTGTGTAGTAGTTGTAGTATATCCACTCTCTCAAAGCATCCAGGCGCCCCC

TGGCTTCGGGTTCTATGTAAACTCCTTCATGCGCCGCTGCCCTGATAACATCCACCACCGCAGAA

TAAGCCACACCCAGCCAACCTACACATTCGTTCTGCGAGTCACACACGGGAGGAGCGGGAAGAG

CTGGAAGAACCATGTTTTTTTTTTATTCCAAAAGATTATCCAAAACCTCAAAATGAAGATCTATTA
```

```
AGTGAACGCGCTCCCCTCCGGTGGCGTGGTCAAACTCTACAGCCAAAGAACAGATAATGGCATT
TGTAAGATGTTGCACAATGGCTTCCAAAAGGCAAACGGCCCTCACGTCCAAGTGGACGTAAAGG
CTAAACCCTTCAGGGTGAATCTCCTCTATAAACATTCCAGCACCTTCAACCATGCCCAATAATTC
TCATCTCGCCACCTTCTCAATATATCTCTAAGCAAATCCCGAATATTTAAGTCCGGGCCATTGTAA
AAAATTTGGCTCCAGAGCGCCCTCCACCTTCAGCCTCAAGCAGCGAATCATGATTGCAAAAATTC
AGGTTCCTCACAGACCTGTATAAGATTCAAAAGCGGAACATTAACAAAAATACCGCGATCCCGTA
GGTCCCTTCGCAGGGCCAGCTGAACATAATCGTGCAGGTCTGCACGGACCAGCGCGGCCACTT
CCCCGCCAGGAACCATGACAAAAGAACCCACACTGATTATGACACGCATACTCGGAGCTATGCTA
ACCAGCGTAGCCCCGATGTAAGCTTGTTGCATGGGCGGCGATATAAAATGCAAGGTGCTGCTCA
AAAAATCAGGCAAAGCCTCGCGCAAAAAGAAAGCACATCGTAGTCATGCTCATGCAGATAAAGG
CAGGTAAGCTCCGGAACCACCACAGAAAAAGACACCATTTTTCTCTCAAACATGTCTGCGGGTTT
CTGCATAAACACAAAATAAAATAACAAAAAAACATTTAAACATTAGAAGCCTGTCTTACAACAGGAA
AAACAACCCTTATAAGCATAAGACGGACTACGGCCATGCCGGCGTGACCGTAAAAAAACTGGTCA
CCGTGATTAAAAAGCACCACCGACAGCTCCTCGGTCAGTCCGGAGTCATAATGTAAGACTCGGTA
AACACATCAGGTTGATTCACATCGGTCAGTGTTAAAAAGCGACCGAAATAGCCNGGGGGAATACA
ATACCCGCAGGCGTAGAGACAACATTACAGCCCCCATAGGAGGTATAACAAAATTAATAGGAGAG
AAAAACACATAAACACCTGAAAAACCCTCCTGCCTAGGCAAAATAGCACCCTCCCGCTCCAGAAC
AACATACAGCGCTTCCACAGCGGCAGCCATAACAGTCAGCCTTACCAGTAAAAAAGAAAACCTAT
TAAAAAAACACCACTCGACACGGCACCAGCTCAATCAGTCACAGTGTAAAAAAGGGCCAAGTGCA
GAGCGAGTATATATAGGACTAAAAAATGACGGTAACGGTTAAAGTCCACAAAAAACACCCAGAAA
ACCGCACGCGAACCTACGCCCAGAAACGAAAGCCAAAAAACCCACAACTTCCTCAAATCGTCACT
TCCGTTTTCCCACGTTACGTCACTTCCCATTTTAAGAAAACTACAATTCCCAACACATACAAGTTAC
TCCGCCCTAAAACCTACGTCACCCGCCCCGTTCCCACGCCCCGCGCCACGTCACAAACTCCACC
CCCTCATTATCATATTGGCTTCAATCCAAAATAAGGTATATTATTGATGATGTTAATTAACATGCAT
GGATCCATATGCGGTGTGAAATACCGCACAGATGCGTAAGGAGAAAATACCGCATCAGGCGCTC
TTCCGCTTCCTCGCTCACTGACTCGCTGCGCTCGGTCGTTCGGCTGCGGCGAGCGGTATCAGCT
CACTCAAAGGCGGTAATACGGTTATCCACAGAATCAGGGGATAACGCAGGAAAGAACATGTGAG
CAAAAGGCCAGCAAAAGGCCAGGAACCGTAAAAAGGCCGCGTTGCTGGCGTTTTTCCATAGGCT
CCGCCCCCTGACGAGCATCACAAAAATCGACGCTCAAGTCAGAGGTGGCGAAACCCGACAGGA
CTATAAAGATACCAGGCGTTTCCCCCTGGAAGCTCCCTCGTGCGCTCTCCTGTTCCGACCCTGCC
GCTTACCGGATACCTGTCCGCCTTTCTCCCTTCGGGAAGCGTGGCGCTTTCTCATAGCTCACGCT
GTAGGTATCTCAGTTCGGTGTAGGTCGTTCGCTCCAAGCTGGGCTGTGTGCACGAACCCCCCGT
TCAGCCCGACCGCTGCGCCTTATCCGGTAACTATCGTCTTGAGTCCAACCCGGTAAGACACGAC
TTATCGCCACTGGCAGCAGCCACTGGTAACAGGATTAGCAGAGCGAGGTATGTAGGCGGTGCTA
CAGAGTTCTTGAAGTGGTGGCCTAACTACGGCTACACTAGAAGGACAGTATTTGGTATCTGCGCT
CTGCTGAAGCCAGTTACCTTCGGAAAAAGAGTTGGTAGCTCTTGATCCGGCAAACAAACCACCGC
TGGTAGCGGTGGTTTTTTTGTTTGCAAGCAGCAGATTACGCGCAGAAAAAAAGGATCTCAAGAAG
ATCCTTTGATCTTTTCTACGGGGTCTGACGCTCAGTGGAACGAAAACTCACGTTAAGGGATTTTG
GTCATGAGATTATCAAAAAGGATCTTCACCTAGATCCTTTTAAATTAAAAATGAAGTTTTAAATCAA
TCTAAAGTATATATGAGTAAACTTGGTCTGACAGTTACCAATGCTTAATCAGTGAGGCACCTATCT
CAGCGATCTGTCTATTTCGTTCATCCATAGTTGCCTGACTCCCCGTCGTGTAGATAACTACGATAC
```

```
GGGAGGGCTTACCATCTGGCCCCAGTGCTGCAATGATACCGCGAGACCCACGCTCACCGGCTC

CAGATTTATCAGCAATAAACCAGCCAGCCGGAAGGGCCGAGCGCAGAAGTGGTCCTGCAACTTT

ATCCGCCTCCATCCAGTCTATTAATTGTTGCCGGGAAGCTAGAGTAAGTAGTTCGCCAGTTAATA

GTTTGCGCAACGTTGTTGCCATTGCTGCAGCCATGAGATTATCAAAAAGGATCTTCACCTAGATC

CTTTTCACGTAGAAAGCCAGTCCGCAGAAACGGTGCTGACCCCGGATGAATGTCAGCTACTGGG

CTATCTGGACAAGGGAAAACGCAAGCGCAAAGAGAAAGCAGGTAGCTTGCAGTGGGCTTACATG

GCGATAGCTAGACTGGGCGGTTTTATGGACAGCAAGCGAACCGGAATTGCCAGCTGGGGCGCC

CTCTGGTAAGGTTGGGAAGCCCTGCAAAGTAAACTGGATGGCTTTCTTGCCGCCAAGGATCTGAT

GGCGCAGGGGATCAAGCTCTGATCAAGAGACAGGATGAGGATCGTTTCGCATGATTGAACAAGA

TGGATTGCACGCAGGTTCTCCGGCCGCTTGGGTGGAGAGGCTATTCGGCTATGACTGGGCACAA

CAGACAATCGGCTGCTCTGATGCCGCCGTGTTCCGGCTGTCAGCGCAGGGGCGCCCGGTTCTTT

TTGTCAAGACCGACCTGTCCGGTGCCCTGAATGAACTGCAAGACGAGGCAGCGCGGCTATCGTG

GCTGGCCACGACGGGCGTTCCTTGCGCAGCTGTGCTCGACGTTGTCACTGAAGCGGGAAGGGA

CTGGCTGCTATTGGGCGAAGTGCCGGGGCAGGATCTCCTGTCATCTCACCTTGCTCCTGCCGAG

AAAGTATCCATCATGGCTGATGCAATGCGGCGGCTGCATACGCTTGATCCGGCTACCTGCCCATT

CGACCACCAAGCGAAACATCGCATCGAGCGAGCACGTACTCGGATGGAAGCCGGTCTTGTCGAT

CAGGATGATCTGGACGAAGAGCATCAGGGGCTCGCGCCAGCCGAACTGTTCGCCAGGCTCAAG

GCGAGCATGCCCGACGGCGAGGATCTCGTCGTGACCCATGGCGATGCCTGCTTGCCGAATATCA

TGGTGGAAAATGGCCGCTTTTCTGGATTCATCGACTGTGGCCGGCTGGGTGTGGCGGACCGCTA

TCAGGACATAGCGTTGGCTACCCGTGATATTGCTGAAGAGCTTGGCGGCGAATGGGCTGACCGC

TTCCTCGTGCTTTACGGTATCGCCGCTCCCGATTCGCAGCGCATCGCCTTCTATCGCCTTCTTGA

CGAGTTCTTCTGAATTTTGTTAAAATTTTTGTTAAATCAGCTCATTTTTTAACCAATAGGCCGAAAT

CGGCAACATCCCTTATAAATCAAAAGAATAGACCGCGATAGGGTTGAGTGTTGTTCCAGTTTGGA

ACAAGAGTCCACTATTAAAGAACGTGGACTCCAACGTCAAAGGGCGAAAAACCGTCTATCAGGGC

GATGGCCCACTACGTGAACCATCACCCAAATCAAGTTTTTTGCGGTCGAGGTGCCGTAAAGCTCT

AAATCGGAACCCTAAAGGGAGCCCCCGATTTAGAGCTTGACGGGGAAAGCCGGCGAACGTGGC

GAGAAAGGAAGGGAAGAAAGCGAAAGGAGCGGGCGCTAGGGCGCTGGCAAGTGTAGCGGTCA

CGCTGCGCGTAACCACCACACCCGCGCGCTTAATGCGCCGCTACAGGGCGCGTCCATTCGCCA

TTCAGGATCGAATTAATTCTTAATTAACATCATCAATAATATACCTTATTTTGGATTGAAGCCAATAT

GATAATGAGGGGGTGGAGTTTGTGACGTGGCGCGGGGCGTGGGAACGGGGCGGGTGACGTAG

TAGTGTGGCGGAAGTGTGATGTTGCAAGTGTGGCGGAACACATGTAAGCGACGGATGTGGCAAA

AGTGACGTTTTTGGTGTGCGCCGGTGTACACAGGAAGTGACAATTTTCGCGCGGTTTTAGGCGG

ATGTTGTAGTAAATTTGGGCGTAACCGAGTAAGATTTGGCCATTTTCGCGGGAAAACTGAATAAG

AGGAAGTGAAATCTGAATAATTTTGTGTTACTCATAGCGCGTAATACTGGTACCGCGGCCGCCTC

GAGTCTAGAGATATCGAATTCAAGCTTAAGGTGCACGGCCCACGTGGCCACTAGTAATTTTCTG

CAGAAAACGTACCCGGGGATCCTCTAGGATCCCACCGAAAGGTTGCTCCTTAACACAGGCTAAG

GACCAGCTTCTTTGGGAGAGAACAGACGCAGGGGCGGGAGGGAAAAAGGGAGAGGCAGACGTC

ACTTCCCCTTGGCGGCTCTGGCAGCAGATTGGTCGGTTGAGTGGCAGAAAGGCAGACGGGAC

TGGGCAAGGCACTGTCGGTGACATCACGGACAGGGCGACTTCTATGTAGATGAGGCAGCGCAG

AGGCTGCTGCTTCGCCACTTGCTGCTTCGCCACGAAGGAGTTCCCGTGCCCTGGGAGCGGGTTC
```

-continued

```
AGGACCGCGGATCGGAAGTGAGAATCCCAGCTGTGTGTCAGGGCTGGAAAGGGCTCGGGAGTG
CGCGGGGCAAGTGACCGTGTGTGTAAAGAGTGAGGCGTATGAGGCTGTGTCGGGGCAGAGCCC
GAAGATCCGGGTTGCGGAGGGTGGGCCTGGGAGGGGTGGTGGCCATTTTTTGTCTAACCCTAAC
TGAGAAGGGCGTAGGCGCCGTGCTTTTGCTCCCCGCGCGCTGTTTTTCTCGCTGACTTTCAGCG
GGCGGAAAAGCCTCGGCCTGCCGCCTTCCACCGTTCATTCTAGAGCAAACAAAAAATGTCAGCT
GCTGGCCCGTTCGCCCCTCCCGGGGACCTGCGGCGGGTCGCCTGCCCAGCCCCCGAACCCCG
CCTGGAGGCCGCGGTCGGCCCGGGGCTTCTCCGGAGGCACCCACTGCCACCGCGAAGAGTTG
GGCTCTGTCAGCCGCGGGTCTCTCGGGGGCGAGGGCGAGGTTCAGGCCTTTCAGGCCGCAGG
AAGAGGAACGGAGCGAGTCCCCGCGCGCGGCGCGATTCCCTGAGCTGTGGGACGTGCACCCA
GGACTCGGCTCACACATGCAGTTCGCTTTCCTGTTGGTGGGGGGAACGCCGATCGTGCGCATCC
GTCACCCCTCGCCGGCAATGGGGGCTTGTGAACCCCCAAACCTGACTGACTGGGCCAGTGTGCT
GCAAATTGGCAGGAGACGTGAAGGCACCTCCAAAGTCGACTTTCTGGAGTTTCAAAAACAGACC
GTACGATGCATTAGTTATTAATAGTAATCAATTACGGGGTCATTAGTTCATAGCCCATATATGGAG
TTCCGCGTTACATAACTTACGGTAAATGGCCCGCCTGGCTGACCGCCCAACGACCCCCGCCCAT
TGACGTCAATAATGACGTATGTTCCCATAGTAACGCCAATAGGGACTTTCCATTGACGTCAATGG
GTGGAGTATTTACGGTAAACTGCCCACTTGGCAGTACATCAAGTGTATCATATGCCAAGTACGCC
CCCTATTGACGTCAATGACGGTAAATGGCCCGCCTGGCATTATGCCCAGTACATGACCTTATGGG
ACTTTCCTACTTGGCAGTACATCTACGTATTAGTCATCGCTATTACCATGGTGATGCGGTTTTGGC
AGTACATCAATGGGCGTGGATAGCGGTTTGACTCACGGGGATTTCCAAGTCTCCACCCCATTGAC
GTCAATGGGAGTTTGTTTTGGCACCAAAATCAACGGGACTTTCCAAAATGTCGTAACAACTCCGC
CCCATTGACGCAAATGGGCGGTAGGCGTGTACGGTGGGAGGTCTATATAAGCAGAGCTGGTTTA
GTGAACCGTCAGATCCGCTAGCCCCACCATGCCGCGCGCTCCCCGCTGCCGAGCCGTGCGCTC
CCTGCTGCGCAGCCACTACCGCGAGGTGCTGCCGCTGGCCACGTTCGTGCGGCGCCTGGGGC
CCCAGGGCTGGCGGCTGGTGCAGCGCGGGGACCCGGCGGCTTTCCGCGCGCTGGTGGCCCAG
TGCCTGGTGTGCGTGCCCTGGGACGCACGGCCGCCCCCCGCCGCCCCCTCCTTCCGCCAGGTG
TCCTGCCTGAAGGAGCTGGTGGCCCGAGTGCTGCAGAGGCTGTGCGAGCGCGGCGCGAAGAAC
GTGCTGGCCTTCGGCTTCGCGCTGCTGGACGGGGCCCGCGGGGGCGCCCCCGAGGCCTTCAC
CACCAGCGTGCGCAGCTACCTGCCCAACACGGTGACCGACGCACTGCGGGGGAGCGGGGCGT
GGGGGCTGCTGTTGCGCCGCGTGGGCGACGACGTGCTGGTTCACCTGCTGGCACGCTGCGCG
CTCTTTGTGCTGGTGGCTCCCAGCTGCGCCTACCAGGTGTGCGGGCCGCCGCTGTACCAGCTC
GGCGCTGCCACTCAGGCCCGGCCCCCGCCACACGCTAGTGGACCCCGAAGGCGTCTGGGATG
CGAACGGGCCTGGAACCATAGCGTCAGGGAGGCCGGGGTCCCCCTGGGCCTGCCAGCCCCGG
GTGCGAGGAGGCGCGGGGGCAGTGCCAGCCGAAGTCTGCCGTTGCCCAAGAGGCCCAGGCGT
GGCGCTGCGCCTGAGCCGGAGCGGACGCCCGTTGGGCAGGGGTCCTGGGCCCACCCGGGCAG
GACGCGTGGACCGAGTGACCGTGGTTTCTGTGTGGTGTCACCTGCCAGACCCGCCGAAGAAGC
CACCTCTTTGGAGGGTGCGCTCTCTGGCACGCGCCACTCCCACCCATCCGTGGGCCGCCAGCA
CCACGCGGGCCCCCCATCCACATCGCGGCCACCACGTCCCTGGGACACGCCTTGTCCCCCGGT
GTACGCCGAGACCAAGCACTTCCTCTACTCCTCAGGCGACAAGGAGCAGCTGCGGCCCTCCTTC
CTACTCAGCTCTCTGAGGCCCAGCCTGACTGGCGCTCGGAGGCTCGTGGAGACCATCTTTCTGG
GTTCCAGGCCCTGGATGCCAGGGACTCCCCGCAGGTTGCCCCGCCTGCCCCAGCGCTACTGGC
AAATGCGGCCCCTGTTTCTGGAGCTGCTTGGGAACCACGCGCAGTGCCCCTACGGGGTGCTCCT
```

-continued

```
CAAGACGCACTGCCCGCTGCGAGCTGCGGTCACCCCAGCAGCCGGTGTCTGTGCCCGGGAGAA

GCCCCAGGGCTCTGTGGCGGCCCCCGAGGAGGAGGACACAGACCCCCGTCGCCTGGTGCAGC

TGCTCCGCCAGCACAGCAGCCCCTGGCAGGTGTACGGCTTCGTGCGGGCCTGCCTGCGCCGGC

TGGTGCCCCAGGCCTCTGGGGCTCCAGGCACAACGAACGCCGCTTCCTCAGGAACACCAAGA

AGTTCATCTCCCTGGGGAAGCATGCCAAGCTCTCGCTGCAGGAGCTGACGTGGAAGATGAGCGT

GCGGGGCTGCGCTTGGCTGCGCAGGAGCCCAGGGGTTGGCTGTGTTCCGGCCGCAGAGCACC

GTCTGCGTGAGGAGATCCTGGCCAAGTTCCTGCACTGGCTGATGAGTGTGTACGTCGTCGAGCT

GCTCAGGTCTTTCTTTTATGTCACGGAGACCACGTTTCAAAAGAACAGGCTCTTTTTCTACCGGAA

GAGTGTCTGGAGCAAGTTGCAAAGCATTGGAATCAGACAGCACTTGAAGAGGGTGCAGCTGCGG

GAGCTGTCGGAAGCAGAGGTCAGGCAGCATCGGGAAGCCAGGCCCGCCCTGCTGACGTCCAGA

CTCCGCTTCATCCCCAAGCCTGACGGGCTGCGGCCGATTGTGAACATGGACTACGTCGTGGGAG

CCAGAACGTTCCGCAGAGAAAAGAGGGCCGAGCGTCTCACCTCCAGGGTGAAGGCACTGTTCA

GCGTGCTCAACTACGAGCGGGCGCGGCGCCCCGGCCTCCTGGGCGCCTCTGTGCTGGGCCTG

GACGATATCCACAGGGCCTGGCGCACCTTCGTGCTGCGTGTGCGGGCCCAGGACCCGCCGCCT

GAGCTGTACTTTGTCAAGGTGGATGTGACGGGCGCGTACGACACCATCCCCCAGGACAGGCTCA

CGGAGGTCATCGCCAGCATCATCAAACCCCAGAACACGTACTGCGTGCGTCGGTATGCCGTGGT

CCAGAAGGCCGCCCATGGGCACGTCCGCAAGGCCTTCAAGAGCCACGTCTCTACCTTGACAGAC

CTCCAGCCGTACATGCGACAGTTCGTGGCTCACCTGCAGGAGACCAGCCCGCTGAGGGATGCC

GTCGTCATCGAGCAGAGCTCCTCCCTGAATGAGGCCAGCAGTGGCCTCTTCGACGTCTTCCTAC

GCTTCATGTGCCACCACGCCGTGCGCATCAGGGGCAAGTCCTACGTCCAGTGCCAGGGGATCC

CGCAGGGCTCCATCCTCTCCACGCTGCTCTGCAGCCTGTGCTACGGCGACATGGAGAACAAGCT

GTTTGCGGGGATTCGGCGGGACGGGCTGCTCCTGCGTTTGGTGGATGATTTCTTGTTGGTGAGA

CCTCACCTCACCCACGCGAAAACCTTCCTCAGGACCCTGGTCCGAGGTGTCCCTGAGTATGGCT

GCGTGGTGAACTTGCGGAAGACAGTGGTGAACTTCCCTGTAGAAGACGAGGCCCTGGGTGGCA

CGGCTTTTGTTCAGATGCCGGCCCACGGCCTATTCCCCTGGTGCGGCCTGCTGCTGGATACCCG

GACCCTGGAGGTGCAGAGCGACTACTCCAGCTATGCCCGGACCTCCATCAGAGCCAGTCTCACC

TTCAACCGCGGCTTCAAGGCTGGGAGGAACATGCGTCGCAAACTCTTTGGGGTCTTGCGGCTGA

AGTGTCACAGCCTGTTTCTGGATTTGCAGGTGAACAGCCTCCAGACGGTGTGCACCAACATCTAC

AAGATCCTCCTGCTGCAGGCGTACAGGTTTCACGCATGTGTGCTGCAGCTCCCATTTCATCAGCA

AGTTTGGAAGAACCCCACATTTTTCCTGCGCGTCATCTCTGACACGGCCTCCCTCTGCTACTCCA

TCCTGAAAGCCAAGAACGCAGGGATGTCGCTGGGGGCCAAGGGCGCCGCCGGCCCTCTGCCCT

CCGAGGCCGTGCAGTGGCTGTGCCACCAAGCATTCCTGCTCAAGCTGACTCGACACCGTGTCAC

CTACGTGCCACTCCTGGGGTCACTCAGGACAGCCCAGACGCAGCTGAGTCGGAAGCTCCCGGG

GACGACGCTGACTGCCCTGGAGGCCGCAGCCAACCCGGCACTGCCCTCAGACTTCAAGACCAT

CCTGGACTGAGTCGAAACTCGCGGCCGCCATATGCATCCTAGGCCTATTAATATTCCGGAGTATA

CGTAGCCGGCTAACGTTAACTTGTTTATTGCAGCTTATAATGGTTACAAATAAAGCAATAGCATCA

CAAATTTCACAAATAAAGCATTTTTTTCACTGCATTCTAGTTGTGGTTTGTCCAAACTCATCAATGT

ATCTTAACGCGGATCTGGGCGTGGTTAAGGGTGGGAAAGAATATATAAGGTGGGGGTCTTATGTA

GTTTTGTATCTGTTTTGCAGCAGCCGCCGCCGCCATGAGCACCAACTCGTTTGATGGAAGCATTG

TGAGCTCATATTTGACAACGCGCATGCCCCCATGGGCCGGGGTGCGTCAGAATGTGATGGGCTC
```

-continued

```
CAGCATTGATGGTCGCCCCGTCCTGCCCGCAAACTCTACTACCTTGACCTACGAGACCGTGTCT
GGAACGCCGTTGGAGACTGCAGCCTCCGCCGCCGCTTCAGCCGCTGCAGCCACCGCCCGCGG
GATTGTGACTGACTTTGCTTTCCTGAGCCCGCTTGCAAGCAGTGCAGCTTCCCGTTCATCCGCCC
GCGATGACAAGTTGACGGCTCTTTTGGCACAATTGGATTCTTTGACCCGGGAACTTAATGTCGTT
TCTCAGCAGCTGTTGGATCTGCGCCAGCAGGTTTCTGCCCTGAAGGCTTCCTCCCCTCCCAATG
CGGTTTAAAACATAAATAAAAAACCAGACTCTGTTTGGATTTGGATCAAGCAAGTGTCTTGCTGTC
TTTATTTAGGGGTTTTGCGCGCGCGGTAGGCCCGGGACCAGCGGTCTCGGTCGTTGAGGGTCCT
GTGTATTTTTTCCAGGACGTGGTAAAGGTGACTCTGGATGTTCAGATACATGGGCATAAGCCCGT
CTCTGGGGTGGAGGTAGCACCACTGCAGAGCTTCATGCTGCGGGGTGGTGTTGTAGATGATCCA
GTCGTAGCAGGAGCGCTGGGCGTGGTGCCTAAAAATGTCTTTCAGTAGCAAGCTGATTGCCAGG
GGCAGGCCCTTGGTGTAAGTGTTTACAAAGCGGTTAAGCTGGGATGGGTGCATACGTGGGGATA
TGAGATGCATCTTGGACTGTATTTTTAGGTTGGCTATGTTCCCAGCCATATCCCTCCGGGGATTCA
TGTTGTGCAGAACCACCAGCACAGTGTATCCGGTGCACTTGGGAAATTTGTCATGTAGCTTAGAA
GGAAATGCGTGGAAGAACTTGGAGACGCCCTTGTGACCTCCAAGATTTTCCATGCATTCGTCCAT
AATGATGGCAATGGGCCCACGGGCGGCGGCCTGGGCGAAGATATTTCTGGGATCACTAACGTCA
TAGTTGTGTTCCAGGATGAGATCGTCATAGGCCATTTTTACAAAGCGCGGGCGGAGGGTGCCAG
ACTGCGGTATAATGGTTCCATCCGGCCCAGGGGCGTAGTTACCCTCACAGATTTGCATTTCCCAC
GCTTTGAGTTCAGATGGGGGGATCATGTCTACCTGCGGGGCGATGAAGAAAACGGTTTCCGGGG
TAGGGGAGATCAGCTGGGAAGAAAGCAGGTTCCTGAGCAGCTGCGACTTACCGCAGCCGGTGG
GCCCGTAAATCACACCTATTACCGGGTGCAACTGGTAGTTAAGAGAGCTGCAGCTGCCGTCATC
CCTGAGCAGGGGGGCCACTTCGTTAAGCATGTCCCTGACTCGCATGTTTTCCCTGACCAAATCC
GCCAGAAGGCGCTCGCCGCCCAGCGATAGCAGTTCTTGCAAGGAAGCAAAGTTTTTCAACGGTT
TGAGACCGTCCGCCGTAGGCATGCTTTTGAGCGTTTGACCAAGCAGTTCCAGGCGGTCCCACAG
CTCGGTCACCTGCTCTACGGCATCTCGATCCAGCATATCTCCTCGTTTCGCGGGTTGGGCGGC
TTTCGCTGTACGGCAGTAGTCGGTGCTCGTCCAGACGGGCCAGGGTCATGTCTTTCCACGGGCG
CAGGGTCCTCGTCAGCGTAGTCTGGGTCACGGTGAAGGGGTGCGCTCCGGGCTGCGCGCTGGC
CAGGGTGCGCTTGAGGCTGGTCCTGCTGGTGCTGAAGCGCTGCCGGTCTTCGCCCTGCGCGTC
GGCCAGGTAGCATTTGACCATGGTGTCATAGTCCAGCCCCTCCGCGGCGTGGCCCTTGGCGCG
CAGCTTGCCCTTGGAGGAGGCGCCGCACGAGGGGCAGTGCAGACTTTTGAGGGCGTAGAGCTT
GGGCGCGAGAAATACCGATTCCGGGGAGTAGGCATCCGCGCCGCAGGCCCCGCAGACGGTCTC
GCATTCCACGAGCCAGGTGAGCTCTGGCCGTTCGGGGTCAAAAACCAGGTTTCCCCCATGCTTT
TTGATGCGTTTCTTACCTCTGGTTTCCATGAGCCGGTGTCCACGCTCGGTGACGAAAAGGCTGTC
CGTGTCGCCGTATACAGACTTGAGAGGCCTGTCCTCGAGCGGTGTTCCGCGGTCCTCCTCGTAT
AGAAACTCGGACCACTCTGAGACAAAGGCTCGCGTCCAGGCCAGCACGAAGGAGGCTAAGTGG
GAGGGGTAGCGGTCGTTGTCCACTAGGGGGTCCACTCGCTCCAGGGTGTGAAGACACATGTCG
CCCTCTTCGGCATCAAGGAAGGTGATTGGTTTGTAGGTGTAGGCCACGTGACCGGGTGTTCCTG
AAGGGGGGCTATAAAAGGGGGTGGGGCGCGTTCGTCCTCACTCTCTTCCGCATCGCTGTCTGC
GAGGGCCAGCTGTTGGGGTGAGTACTCCCTCTGAAAAGCGGGCATGACTTCTGCGCTAAGATTG
TCAGTTTCCAAAAACGAGGAGGATTTGATATTCACCTGGCCCGCGGTGATGCCTTTGAGGGTGG
CCGCATCCATCTGGTCAGAAAAGACAATCTTTTTGTTGTCAAGCTTGGTGGCAAACGACCCGTAG
AGGGCGTTGGACAGCAACTTGGCGATGGAGCGCAGGGTTTGGTTTTTGTCGCGATCGGCGCGC
```

```
TCCTTGGCCGCGATGTTTAGCTGCACGTATTCGCGCGCAACGCACCGCCATTCGGGAAAGACGG

TGGTGCGCTCGTCGGGCACCAGGTGCACGCGCCAACCGCGGTTGTGCAGGGTGACAAGGTCAA

CGCTGGTGGCTACCTCTCCGCGTAGGCGCTCGTTGGTCCAGCAGAGGCGGCCGCCCTTGCGCG

AGCAGAATGGCGGTAGGGGGTCTAGCTGCGTCTCGTCCGGGGGTCTGCGTCCACGGTAAAGA

CCCCGGGCAGCAGGCGCGCGTCGAAGTAGTCTATCTTGCATCCTTGCAAGTCTAGCGCCTGCTG

CCATGCGCGGGCGGCAAGCGCGCGCTCGTATGGGTTGAGTGGGGGACCCCATGGCATGGGGT

GGGTGAGCGCGGAGGCGTACATGCCGCAAATGTCGTAAACGTAGAGGGGCTCTCTGAGTATTCC

AAGATATGTAGGGTAGCATCTTCCACCGCGGATGCTGGCGCGCACGTAATCGTATAGTTCGTGC

GAGGGAGCGAGGAGGTCGGGACCGAGGTTGCTACGGGCGGGCTGCTCTGCTCGGAAGACTATC

TGCCTGAAGATGGCATGTGAGTTGGATGATATGGTTGGACGCTGGAAGACGTTGAAGCTGGCGT

CTGTGAGACCTACCGCGTCACGCACGAAGGAGGCGTAGGAGTCGCGCAGCTTGTTGACCAGCT

CGGCGGTGACCTGCACGTCTAGGGCGCAGTAGTCCAGGGTTTCCTTGATGATGTCATACTTATC

CTGTCCCTTTTTTTTCCACAGCTCGCGGTTGAGGACAAACTCTTCGCGGTCTTTCCAGTACTCTTG

GATCGGAAACCCGTCGGCCTCCGAACGGTAAGAGCCTAGCATGTAGAACTGGTTGACGGCCTGG

TAGGCGCAGCATCCCTTTTCTACGGGTAGCGCGTATGCCTGCGCGGCCTTCCGGAGCGAGGTGT

GGGTGAGCGCAAAGGTGTCCCTGACCATGACTTTGAGGTACTGGTATTTGAAGTCAGTGTCGTC

GCATCCGCCCTGCTCCCAGAGCAAAAAGTCCGTGCGCTTTTTGGAACGCGGATTTGGCAGGGCG

AAGGTGACATCGTTGAAGAGTATCTTTCCCGCGCGAGGCATAAAGTTGCGTGTGATGCGGAAGG

GTCCCGGCACCTCGGAACGGTTGTTAATTACCTGGGCGGCGAGCACGATCTCGTCAAAGCCGTT

GATGTTGTGGCCCACAATGTAAAGTTCCAAGAAGCGCGGGATGCCGTTGATGGAAGGCAATTTTT

TAAGTTCCTCGTAGGTGAGCTCTTCAGGGGAGCTGAGCCCGTGCTCTGAAAGGGCCCAGTCTGC

AAGATGAGGGTTGGAAGCGACGAATGAGCTCCACAGGTCACGGGCCATTAGCATTTGCAGGTGG

TCGCGAAAGGTCCTAAACTGGCGACCTATGGCCATTTTTTCTGGGGTGATGCAGTAGAAGGTAAG

CGGGTCTTGTTCCGAGGGGTCCCATCCAAGGTTCGCGGCTAGGTCTCGCGCGGCAGTCACTAGA

GGCTCATCTCCGCCGAACTTCATGACCAGCATGAAGGGCACGAGCTGCTTCCCAAAGGCCCCCA

TCCAAGTATAGGTCTCTACATCGTAGGTGACAAAGAGACGCTCGGTGCGAGGATGCGAGCCGAT

CGGGAAGAACTGGATCTCCCGCCACCAATTGGAGGAGTGGCTATTGATGTGGTGAAAGTAGAAG

TCCCTGCGACGGGCCGAACACTCGTGCTGGCTTTTGTAAAAACGTGCGCAGTACTGGCAGCGGT

GCACGGGCTGTACATCCTGCACGAGGTTGACCTGACGACCGCGCACAAGGAAGCAGAGTGGGA

ATTTGAGCCCCTCGCCTGGCGGGTTTGGCTGGTGGTCTTCTACTTCGGCTGCTTGTCCTTGACC

GTCTGGCTGCTCGAGGGGAGTTACGGTGGATCGGACCACCACGCCGCGCGAGCCCAAAGTCCA

GATGTCCGCGCGCGGCGGTCGGAGCTTGATGACAACATCGCGCAGATGGGAGCTGTCCATGGT

CTGGAGCTCCCGCGGCGTCAGGTCAGGCGGGAGCTCCTGCAGGTTTACCTCGCATAGACGGGT

CAGGGCGCGGGCTAGATCCAGGTGATACCTAATTTCCAGGGGCTGGTTGGTGGCGGCGTCGAT

GGCTTGCAAGAGGCCGCATCCCCGCGCGCGACTACGGTACCGCGCGGCGGGCGGTGGGCCG

CGGGGGTGTCCTTGGATGATGCATCTAAAAGCGGTGACGCGGGCGAGCCCCCGGAGGTAGGGG

GGGCTCCGGACCCGCCGGGAGAGGGGGCAGGGGCACGTCGGCGCCGCGCGCGGGCAGGAGC

TGGTGCTGCGCGCGTAGGTTGCTGGCGAACGCGACGACGCGGCGGTTGATCTCCTGAATCTGG

CGCCTCTGCGTGAAGACGACGGGCCCGGTGAGCTTGAGCCTGAAAGAGAGTTCGACAGAATCAA

TTTCGGTGTCGTTGACGGCGGCCTGGCGCAAAATCTCCTGCACGTCTCCTGAGTTGTCTTGATAG
```

-continued
```
GCGATCTCGGCCATGAACTGCTCGATCTCTTCCTCCTGGAGATCTCCGCGTCCGGCTCGCTCCA
CGGTGGCGGCGAGGTCGTTGGAAATGCGGGCCATGAGCTGCGAGAAGGCGTTGAGGCCTCCCT
CGTTCCAGACGCGGCTGTAGACCACGCCCCCTTCGGCATCGCGGGCGCGCATGACCACCTGCG
CGAGATTGAGCTCCACGTGCCGGGCGAAGACGGCGTAGTTTCGCAGGCGCTGAAAGAGGTAGT
TGAGGGTGGTGGCGGTGTGTTCTGCCACGAAGAAGTACATAACCCAGCGTCGCAACGTGGATTC
GTTGATATCCCCCAAGGCCTCAAGGCGCTCCATGGCCTCGTAGAAGTCCACGGCGAAGTTGAAA
AACTGGGAGTTGCGCGCCGACACGGTTAACTCCTCCTCCAGAAGACGGATGAGCTCGGCGACA
GTGTCGCGCACCTCGCGCTCAAAGGCTACAGGGGCCTCTTCTTCTTCTTCAATCTCCTCTTCCAT
AAGGGCCTCCCCTTCTTCTTCTTCTGGCGGCGGTGGGGAGGGGGACAGGGCGGCGAGGAC
GGCGCACCGGGAGGCGGTCGACAAAGCGCTCGATCATCTCCCCGCGGCGACGGCGCATGGTCT
CGGTGACGGCGCGGCCGTTCTCGCGGGGCGCAGTTGGAAGACGCCGCCCGTCATGTCCCGG
TTATGGGTTGGCGGGGGGCTGCCATGCGGCAGGGATACGGCGCTAACGATGCATCTCAACAATT
GTTGTGTAGGTACTCCGCCGCCGAGGGACCTGAGCGAGTCCGCATCGACCGGATCGGAAAACC
TCTCGAGAAAGGCGTCTAACCAGTCACAGTCGCAAGGTAGGCTGAGCACCGTGGCGGGCGGCA
GCGGGCGGCGGTCGGGGTTGTTTCTGGCGGAGGTGCTGCTGATGATGTAATTAAAGTAGGCGG
TCTTGAGACGGCGGATGGTCGACAGAAGCACCATGTCCTTGGGTCCGGCCTGCTGAATGCGCAG
GCGGTCGGCCATGCCCCAGGCTTCGTTTTGACATCGGCGCAGGTCTTTGTAGTAGTCTTGCATG
AGCCTTTCTACCGGCACTTCTTCTTCTCCTTCCTCTTGTCCTGCATCTCTTGCATCTATCGCTGCG
GCGGCGGCGGAGTTTGGCCGTAGGTGGCGCCCTCTTCCTCCCATGCGTGTGACCCCGAAGCCC
CTCATCGGCTGAAGCAGGGCTAGGTCGGCGACAACGCGCTCGGCTAATATGGCCTGCTGCACCT
GCGTGAGGGTAGACTGGAAGTCATCCATGTCCACAAAGCGGTGGTATGCGCCCGTGTTGATGGT
GTAAGTGCAGTTGGCCATAACGGACCAGTTAACGGTCTGGTGACCCGGCTGCGAGAGCTCGGTG
TACCTGAGACGCGAGTAAGCCCTCGAGTCAAATACGTAGTCGTTGCAAGTCCGCACCAGGTACT
GGTATCCCACCAAAAAGTGCGGCGGCGGCTGGCGGTAGAGGGGCCAGCGTAGGGTGGCCGGG
GCTCCGGGGGCGAGATCTTCCAACATAAGGCGATGATATCCGTAGATGTACCTGGACATCCAGG
TGATGCCGGCGGCGGTGGTGGAGGCGCGCGGAAAGTCGCGGACGCGGTTCCAGATGTTGCGC
AGCGGCAAAAAGTGCTCCATGGTCGGGACGCTCTGGCCGGTCAGGCGCGCGCAATCGTTGACG
CTCTACCGTGCAAAAGGAGAGCCTGTAAGCGGGCACTCTTCCGTGGTCTGGTGGATAAATTCGC
AAGGGTATCATGGCGGACGACCGGGGTTCGAGCCCCGTATCCGGCCGTCCGCCGTGATCCATG
CGGTTACCGCCCGCGTGTCGAACCCAGGTGTGCGACGTCAGACAACGGGGAGTGCTCCTTTT
GGCTTCCTTCCAGGCGCGGCGGCTGCTGCGCTAGCTTTTTTGGCCACTGGCCGCGCGCAGCGT
AAGCGGTTAGGCTGGAAAGCGAAAGCATTAAGTGGCTCGCTCCCTGTAGCCGGAGGGTTATTTT
CCAAGGGTTGAGTCGCGGGACCCCCGGTTCGAGTCTCGGACCGGCCGGACTGCGGCGAACGG
GGGTTTGCCTCCCCGTCATGCAAGACCCCGCTTGCAAATTCCTCCGGAAACAGGGACGAGCCCC
TTTTTTGCTTTTCCCAGATGCATCCGGTGCTGCGGCAGATGCGCCCCCCTCCTCAGCAGCGGCA
AGAGCAAGAGCAGCGGCAGACATGCAGGGCACCCTCCCCTCCTCCTACCGCGTCAGGAGGGGC
GACATCCGCGGTTGACGCGGCAGCAGATGGTGATTACGAACCCCCGCGGCGCCGGGCCCGGC
ACTACCTGGACTTGGAGGAGGGCGAGGGCCTGGCGCGGCTAGGAGCGCCCTCTCCTGAGCGGT
ACCCAAGGGTGCAGCTGAAGCGTGATACGCGTGAGGCGTACGTGCCGCGGCAGAACCTGTTTC
GCGACCGCGAGGGAGAGGAGCCCGAGGAGATGCGGGATCGAAAGTTCCACGCAGGGCGCGAG
CTGCGGCATGGCCTGAATCGCGAGCGGTTGCTGCGCGAGGAGGACTTTGAGCCCGACGCGCGA
```

```
ACCGGGATTAGTCCCGCGCGCACACGTGGCGGCCGCCGACCTGGTAACCGCATACGAGCAG

ACGGTGAACCAGGAGATTAACTTTCAAAAAAGCTTTAACAACCACGTGCGTACGCTTGTGGCGCG

CGAGGAGGTGGCTATAGGACTGATGCATCTGTGGGACTTTGTAAGCGCGCTGGAGCAAAACCCA

AATAGGAAGCCGCTCATGGCGCAGCTGTTCCTTATAGTGCAGCACAGCAGGGACAACGAGGCAT

TCAGGGATGCGCTGCTAAACATAGTAGAGCCCGAGGGCCGCTGGCTGCTCGATTTGATAAACAT

CCTGCAGAGCATAGTGGTGCAGGAGCGCAGCTTGAGCCTGGCTGACAAGGTGGCCGCCATCAA

CTATTCCATGCTTAGCCTGGGCAAGTTTTACGCCCGCAAGATATACCATACCCCTTACGTTCCCAT

AGACAAGGAGGTAAAGATCGAGGGGTTCTACATGCGCATGGCGCTGAAGGTGCTTACCTTGAGC

GACGACCTGGGCGTTTATCGCAACGAGCGCATCCACAAGGCCGTGAGCGTGAGCCGGCGGCGC

GAGCTCAGCGACCGCGAGCTGATGCACAGCCTGCAAAGGGCCCTGGCTGGCACGGGCAGCGG

CGATAGAGAGGCCGAGTCCTACTTTGACGCGGGCGCTGACCTGCGCTGGGCCCCAAGCCGAGG

CGCCCTGGAGGCAGCTGGGGCCGGACCTGGGCTGGCGGTGGCACCCGCGCGCGCTGGCAACG

TCGGCGGCGTGGAGGAATATGACGAGGACGATGAGTACGAGCCAGAGGACGGCGAGTACTAAG

CGGTGATGTTTCTGATCAGATGATGCAAGACGCAACGGACCCGGCGGTGCGGGCGGCGCTGCA

GAGCCAGCCGTCCGGCCTTAACTCCACGGACGACTGGCGCCAGGTCATGGACCGCATCATGTC

GCTGACTGCGCGCAATCCTGACGCGTTCCGGCAGCAGCCGCAGGCCAACCGGCTCTCCGCAAT

TCTGGAAGCGGTGGTCCCGGCGCGCGCAAACCCCACGCACGAGAAGGTGCTGGCGATCGTAAA

CGCGCTGGCCGAAAACAGGGCCATCCGGCCCGACGAGGCCGGCCTGGTCTACGACGCGCTGC

TTCAGGGCGTGGCTCGTTACAACAGCGGCAACGTGCAGACCAACCTGGACCGGCTGGTGGGGG

ATGTGCGCGAGGCCGTGGCGCAGCGTGAGCGCGCGCAGCAGCAGGGCAACCTGGGCTCCATG

GTTGCACTAAACGCCTTCCTGAGTACACAGCCCGCCAACGTGCCGCGGGGACAGGAGGACTACA

CCAACTTTGTGAGCGCACTGCGGCTAATGGTGACTGAGACACCGCAAAGTGAGGTGTACCAGTC

TGGGCCAGACTATTTTTTCCAGACCAGTAGACAAGGCCTGCAGACCGTAAACCTGAGCCAGGCTT

TCAAAAACTTGCAGGGGCTGTGGGGGGTGCGGGCTCCCACAGGCGACCGCGCGACCGTGTCTA

GCTTGCTGACGCCCAACTCGCGCCTGTTGCTGCTGCTAATAGCGCCCTTCACGGACAGTGGCAG

CGTGTCCCGGGACACATACCTAGGTCACTTGCTGACACTGTACCGCGAGGCCATAGGTCAGGCG

CATGTGGACGAGCATACTTTCCAGGAGATTACAAGTGTCAGCCGCGCGCTGGGGCAGGAGGACA

CGGGCAGCCTGGAGGCAACCCTAAACTACCTGCTGACCAACCGGCGGCAGAAGATCCCCTCGTT

GCACAGTTTAAACAGCGAGGAGGAGCGCATTTTGCGCTACGTGCAGCAGAGCGTGAGCCTTAAC

CTGATGCGCGACGGGGTAACGCCCAGCGTGGCGCTGGACATGACCGCGCGCAACATGGAACCG

GGCATGTATGCCTCAAACCGGCCGTTTATCAACCGCCTAATGGACTACTTGCATCGCGCGGCCG

CCGTGAACCCCGAGTATTTCACCAATGCCATCTTGAACCCGCACTGGCTACCGCCCCTGGTTTC

TACACCGGGGATTCGAGGTGCCCGAGGGTAACGATGGATTCCTCTGGGACGACATAGACGACA

GCGTGTTTTCCCCGCAACCGCAGACCCTGCTAGAGTTGCAACAGCGCGAGCAGGCAGAGGCGG

CGCTGCGAAAGGAAAGCTTCCGCAGGCCAAGCAGCTTGTCCGATCTAGGCGCTGCGGCCCCGC

GGTCAGATGCTAGTAGCCCATTTCCAAGCTTGATAGGGTCTCTTACCAGCACTCGCACCACCCGC

CCGCGCCTGCTGGGCGAGGAGGAGTACCTAAACAACTCGCTGCTGCAGCCGCAGCGCGAAAAA

AACCTGCCTCCGGCATTTCCCAACAACGGGATAGAGAGCCTAGTGGACAAGATGAGTAGATGGA

AGACGTACGCGCAGGAGCACAGGGACGTGCCAGGCCCGCGCCCGCCCACCCGTCGTCAAAGG

CACGACCGTCAGCGGGGTCTGGTGTGGGAGGACGATGACTCGGCAGACGACAGCAGCGTCCTG
```

-continued

```
GATTTGGGAGGGAGTGGCAACCCGTTTGCGCACCTTCGCCCCAGGCTGGGGAGAATGTTTTAAA
AAAAAAAAGCATGATGCAAAATAAAAAACTCACCAAGGCCATGGCACCGAGCGTTGGTTTTCTT
GTATTCCCCTTAGTATGCGGCGCGCGGCGATGTATGAGGAAGGTCCTCCTCCCTCCTACGAGAG
TGTGGTGAGCGCGGCGCCAGTGGCGGCGGCGCTGGGTTCTCCCTTCGATGCTCCCCTGGACCC
GCCGTTTGTGCCTCCGCGGTACCTGCGGCCTACCGGGGGAGAAACAGCATCCGTTACTCTGA
GTTGGCACCCCTATTCGACACCACCCGTGTGTACCTGGTGGACAACAAGTCAACGGATGTGGCA
TCCCTGAACTACCAGAACGACCACAGGAACTTTCTGACCACGGTCATTGAAAACAATGACTACAG
CCCGGGGGAGGCAAGCACACAGACCATCAATCTTGACGACCGGTCGCACTGGGGCGGCGACCT
GAAAACCATCCTGCATACCAACATGCCAAATGTGAACGAGTTCATGTTTACCAATAAGTTTAAGGC
GCGGGTGATGGTGTCGCGCTTGCCTACTAAGGACAATCAGGTGGAGCTGAAATACGAGTGGGTG
GAGTTGAGGCTGCCCGAGGGCAACTACTCCGAGACCATGACCATAGACCTTATGAACAACGCGA
TCGTGGAGCACTACTTGAAAGTGGGCAGACAGAACGGGGTTCTGGAAAGCGACATCGGGGTAAA
GTTTGACACCCGCAACTTCAGACTGGGGTTTGACCCCGTCACTGGTCTTGTCATGCCTGGGGTAT
ATACAAACGAAGCCTTCCATCCAGACATCATTTTGCTGCCAGGATGCGGGGTGGACTTCACCCAC
AGCCGCCTGAGGAACTTGTTGGGCATCCGCAAGCGGCAACCCTTCCAGGAGGGCTTTAGGATCA
CCTACGATGATCTGGAGGGTGGTAACATTCCCGCACTGTTGGATGTGGACGCCTACCAGGCGAG
CTTGAAAGATGACACCGAACAGGGCGGGGGTGGCGCAGGCGGCAGCAACAGCAGTGGCAGCG
GCGCGGAAGAGAACTCCAACGCGGCAGCCGCGGCAATGCAGCCGGTGGAGGACATGAACGATC
ATGCCATTCGCGGCGACACCTTTGCCAGAGGGGCTGAGGAGAAGCGCGCTGAGGCCGAAGCAG
CGGCCGAAGCTGCCGCCCCCGCTGCGCAACCCGAGGTCGAGAAGCCTCAGAAGAAACCGGTGA
TCAAACCCCTGACAGAGGACAGCAAGAAACGCAGTTACAACCTAATAAGCAATGACAGCACCTTC
ACCCAGTACCGCAGCTGGTACCTTGCATACAACTACGGCGACCCTCAGACCGGAATCCGCTCAT
GGACCCTGCTTTGCACTCCTGACGTAACCTGCGGCTCGGAGCAGGTCTACTGGTCGTTGCCAGA
CATGATGCAAGACCCCGTGACCTTCCGCTCCACGCGCCAGATCAGCAACTTTCCGGTGGTGGGC
GCCGAGCTGTTGCCCGTGCACTCCAAGAGCTTCTACAACGACCAGGCCGTCTACTCCCAACTCA
TCCGCCAGTTTACCTCTCTGACCCACGTGTTCAATCGCTTTCCCGAGAACCAGATTTTGGCGCGC
CCGCCAGCCCCCACCATCACCACCGTCAGTGAAAACGTTCCTGCTCTCACAGATCACGGGACGC
TACCGCTGCGCAACAGCATCGGAGGAGTCCAGCGAGTGACCATTACTGACGCCAGACGCCGCA
CCTGCCCCTACGTTTACAAGGCCCTGGGCATAGTCTCGCCGCGCGTCCTATCGAGCCGCACTTT
TTGAGCAAGCATGTCCATCCTTATATCGCCCAGCAATAACACAGGCTGGGGCCTGCGCTTCCCAA
GCAAGATGTTTGGCGGGCCAAGAAGCGCTCCGACCAACACCCAGTGCGCGTGCGCGGGCACT
ACCGCGCGCCCTGGGGCGCGCACAAACGCGGCCGCACTGGGCGCACCACCGTCGATGACGCC
ATCGACGCGGTGGTGGAGGAGGCGCGCAACTACACGCCCACGCCGCCACCAGTGTCCACAGTG
GACGCGGCCATTCAGACCGTGGTGCGCGGAGCCCGGCGCTATGCTAAAATGAAGAGACGGCGG
AGGCGCGTAGCACGTCGCCACCGCCGCCGACCCGGCACTGCCGCCCAACGCGCGGCGGCGGC
CCTGCTTAACCGCGCACGTCGCACCGGCCGAGGGGCGGCCATGCGGGCCGCTCGAAGGCTGG
CCGCGGGTATTGTCACTGTGCCCCCCAGGTCCAGGCGACGAGCGGCCGCCGCAGCAGCCGCG
GCCATTAGTGCTATGACTCAGGGTCGCAGGGGCAACGTGTATTGGGTGCGCGACTCGGTTAGCG
GCCTGCGCGTGCCCGTGCGCACCCGCCCCCCGCGCAACTAGATTGCAAGAAAAAACTACTTAGA
CTCGTACTGTTGTATGTATCCAGCGGCGGCGGCGCGCAACGAAGCTATGTCCAAGCGCAAAATC
AAAGAAGAGATGCTCCAGGTCATCGCGCCGGAGATCTATGGCCCCCCGAAGAAGGAAGAGCAG
```

-continued

```
GATTACAAGCCCCGAAAGCTAAAGCGGGTCAAAAAGAAAAAGAAAGATGATGATGATGAACTTGA

CGAGGAGGTGGAACTGCTGCACGCTACCGCGCCCAGGCGAGGGGTACAGTGGAAAGGTCGACG

CGTAAAACGTGTTTTGCGACCCGGCACCACCGTAGTCTTTACGCCCGGTGAGCGCTCCACCCGC

ACCTACAAGCGCGTGTATGATGAGGTGTACGGCGACGAGGACCTGCTTGAGCAGGCCAACGAG

CGCCTCGGGGAGTTTGCCTACGGAAAGCGGCATAAGGACATGCTGGCGTTGCCGCTGGACGAG

GGCAACCCAACACCTAGCCTAAAGCCCGTAACACTGCAGGAGGTGCTGCCCGCGCTTGCACCGT

CCGAAGAAAAGCGCGGCCTAAAGCGCGAGTCTGGTGACTTGGCACCCACCGTGCAGCTGATGG

TACCCAAGCGCCAGCGACTGGAAGATGTCTTGGAAAAAATGACCGTGGAACCTGGGCTGGAGCC

CGAGGTCCGCGTGCGGCCAATCAAGCAGGTGGCGCCGGGACTGGGCGTGCAGACCGTGGACG

TTCAGATACCCACTACCAGTAGCACCAGTATTGCCACCGCCACAGAGGGCATGGAGACACAAAC

GTCCCCGGTTGCCTCAGCGGTGGCGGATGCCGCGGTGCAGGCGGTCGCTGCGGCCGCGTCCA

AGACCTCTACGGAGGTGCAAACGGACCCGTGGATGTTTCGCGTTTCAGCCCCCCGGCGCCCGC

GCGGTTCGAGGAAGTACGGCGCCGCCAGCGCGCTACTGCCCGAATATGCCCTACATCCTTCCAT

TGCGCCTACCCCCGGCTATCGTGGCTACACCTACCGCCCCAGAAGACGAGCAACTACCCGACGC

CGAACCACCACTGGAACCCGCCGCCGCCGTCGCCGTCGCCAGCCCGTGCTGGCCCCGATTTCC

GTGCGCAGGGTGGCTCGCGAAGGAGGCAGGACCCTGGTGCTGCCAACAGCGCGCTACCACCC

CAGCATCGTTTAAAAGCCGGTCTTTGTGGTTCTTGCAGATATGGCCCTCACCTGCCGCCTCCGTT

TCCCGGTGCCGGGATTCCGAGGAAGAATGCACCGTAGGAGGGGCATGGCCGGCCACGGCCTGA

CGGGCGGCATGCGTCGTGCGCACCACCGGCGGCGGCGCGCGTCGCACCGTCGCATGCGCGGC

GGTATCCTGCCCCTCCTTATTCCACTGATCGCCGCGGCGATTGGCGCCGTGCCCGGAATTGCAT

CCGTGGCCTTGCAGGCGCAGAGACACTGATTAAAAACAAGTTGCATGTGGAAAAATCAAATAAA

AAGTCTGGACTCTCACGCTCGCTTGGTCCTGTAACTATTTTGTAGAATGGAAGACATCAACTTTGC

GTCTCTGGCCCCGCGACACGGCTCGCGCCCGTTCATGGGAAACTGGCAAGATATCGGCACCAG

CAATATGAGCGGTGGCGCCTTCAGCTGGGGCTCGCTGTGGAGCGGCATTAAAAATTTCGGTTCC

ACCGTTAAGAACTATGGCAGCAAGGCCTGGAACAGCAGCACAGGCCAGATGCTGAGGGATAAGT

TGAAAGAGCAAAATTTCCAACAAAAGGTGGTAGATGGCCTGGCCTCTGGCATTAGCGGGGTGGT

GGACCTGGCCAACCAGGCAGTGCAAAATAAGATTAACAGTAAGCTTGATCCCCGCCCTCCCGTA

GAGGAGCCTCCACCGGCCGTGGAGACAGTGTCTCCAGAGGGGCGTGGCGAAAAGCGTCCGCG

CCCCGACAGGGAAGAAACTCTGGTGACGCAAATAGACGAGCCTCCCTCGTACGAGGAGGCACTA

AAGCAAGGCCTGCCCACCACCCGTCCCATCGCGCCCATGGCTACCGGAGTGCTGGGCCAGCAC

ACACCCGTAACGCTGGACCTGCCTCCCCCCGCCGACACCCAGCAGAAACCTGTGCTGCCAGGC

CCGACCGCCGTTGTTGTAACCCGTCCTAGCCGCGCGTCCCTGCGCCGCGCCGCCAGCGGTCCG

CGATCGTTGCGGCCCGTAGCCAGTGGCAACTGGCAAAGCACACTGAACAGCATCGTGGGTCTG

GGGGTGCAATCCCTGAAGCGCCGACGATGCTTCTGAATAGCTAACGTGTCGTATGTGTCATGT

ATGCGTCCATGTCGCCGCCAGAGGAGCTGCTGAGCCGCCGCGCGCCCGCTTTCCAAGATGGCT

ACCCCTTCGATGATGCCGCAGTGGTCTTACATGCACATCTCGGGCCAGGACGCCTCGGAGTACC

TGAGCCCCGGGCTGGTGCAGTTTGCCCGCGCCACCGAGACGTACTTCAGCCTGAATAACAAGTT

TAGAAACCCCACGGTGGCGCCTACGCACGACGTGACCACAGACCGGTCCGAGGGTTTGACGCT

GCGGTTCATCCCTGTGGACCGTGAGGATACTGCGTACTCGTACAAGGCGCGGTTCACCCTAGCT

GTGGGTGATAACCGTGTGCTGGACATGGCTTCCACGTACTTTGACATCCGCGGCGTGCTGGACA
```

-continued

```
GGGGCCCTACTTTTAAGCCCTACTCTGGCACTGCCTACAACGCCCTGGCTCCCAAGGGTGCCCC
AAATCCTTGCGAATGGGATGAAGCTGCTACTGCTCTTGAAATAAACCTAGAAGAAGAGGACGATG
ACAACGAAGACGAAGTAGACGAGCAAGCTGAGCAGCAAAAAACTCACGTATTTGGGCAGGCGCC
TTATTCTGGTATAAATATTACAAAGGAGGGTATTCAAATAGGTGTCGAAGGTCAAACACCTAAATA
TGCCGATAAAACATTTCAACCTGAACCTCAAATAGGAGAATCTCAGTGGTACGAAACTGAAATTAA
TCATGCAGCTGGGAGAGTCCTTAAAAAGACTACCCCAATGAAACCATGTTAGGGTTCATATGCAA
AACCCACAAATGAAATGGAGGGCAAGGCATTCTTGTAAAGCAACAAAATGGAAAGCTAGAAAGT
CAAGTGGAAATGCAATTTTTCTCAACTACTGAGGCGACCGCAGGCAATGGTGATAACTTGACTCC
TAAAGTGGTATTGTACAGTGAAGATGTAGATATAGAAACCCCAGACACTCATATTTCTTACATGCC
CACTATTAAGGAAGGTAACTCACGAGAACTAATGGGCCAACAATCTATGCCCAACAGGCCTAATT
ACATTGCTTTTAGGGACAATTTTATTGGTCTAATGTATTACAACAGCACGGGTAATATGGGTGTTC
TGGCGGGCCAAGCATCGCAGTTGAATGCTGTTGTAGATTTGCAAGACAGAAACACAGAGCTTTCA
TACCAGCTTTTGCTTGATTCCATTGGTGATAGAACCAGGTACTTTTCTATGTGGAATCAGGCTGTT
GACAGCTATGATCCAGATGTTAGAATTATTGAAAATCATGGAACTGAAGATGAACTTCCAAATTAC
TGCTTTCCACTGGGAGGTGTGATTAATACAGAGACTCTTACCAAGGTAAAACCTAAAACAGGTCA
GGAAATGGATGGGAAAAAGATGCTACAGAATTTTCAGATAAAAATGAAATAAGAGTTGGAAATAA
TTTTGCCATGGAAATCAATCTAAATGCCAACCTGTGGAGAAATTTCCTGTACTCCAACATAGCGCT
GTATTTGCCCGACAAGCTAAAGTACAGTCCTTCCAACGTAAAAATTTCTGATAACCCAAACACCTA
CGACTACATGAACAAGCGAGTGGTGGCTCCCGGGTTAGTGGACTGCTACATTAACCTTGGAGCA
CGCTGGTCCCTTGACTATATGGACAACGTCAACCCATTTAACCACCACCGCAATGCTGGCCTGCG
CTACCGCTCAATGTTGCTGGGCAATGGTCGCTATGTGCCCTTCCACATCCAGGTGCCTCAGAAGT
TCTTTGCCATTAAAAACCTCCTTCTCCTGCCGGGCTCATACACCTACGAGTGGAACTTCAGGAAG
GATGTTAACATGGTTCTGCAGAGCTCCCTAGGAAATGACCTAAGGGTTGACGGAGCCAGCATTAA
GTTTGATAGCATTTGCCTTTACGCCACCTTCTTCCCCATGGCCCACAACACCGCCTCCACGCTTG
AGGCCATGCTTAGAAACGACACCAACGACCAGTCCTTTAACGACTATCTCTCCGCCGCCAACATG
CTCTACCCTATACCCGCCAACGCTACCAACGTGCCCATATCCATCCCCTCCCGCAACTGGGCGG
CTTTCCGCGGCTGGGCCTTCACGCGCCTTAAGACTAAGGAAACCCCATCACTGGGCTCGGGCTA
CGACCCTTATTACACCTACTCTGGCTCTATACCCTACCTAGATGGAACCTTTTACCTCAACCACAC
CTTTAAGAAGGTGGCCATTACCTTTGACTCTTCTGTCAGCTGGCCTGGCAATGACCGCCTGCTTA
CCCCCAACGAGTTTGAAATTAAGCGCTCAGTTGACGGGGAGGGTTACAACGTTGCCCAGTGTAA
CATGACCAAAGACTGGTTCCTGGTACAAATGCTAGCTAACTACAACATTGGCTACCAGGGCTTCT
ATATCCCAGAGAGCTACAAGGACCGCATGTACTCCTTCTTTAGAAACTTCCAGCCCATGAGCCGT
CAGGTGGTGGATGATACTAAATACAAGGACTACCAACAGGTGGGCATCCTACACCAACACAACAA
CTCTGGATTTGTTGGCTACCTTGCCCCCACCATGCGCGAAGGACAGGCCTACCCTGCTAACTTCC
CCTATCCGCTTATAGGCAAGACCGCAGTTGACAGCATTACCCAGAAAAAGTTTCTTTGCGATCGC
ACCCTTTGGCGCATCCCATTCTCCAGTAACTTTATGTCCATGGGCGCACTCACAGACCTGGGCCA
AAACCTTCTCTACGCCAACTCCGCCCACGCGCTAGACATGACTTTTGAGGTGGATCCCATGGACG
AGCCCACCCTTCTTTATGTTTTGTTTGAAGTCTTTGACGTGGTCCGTGTGCACCGGCCGCACCGC
GGCGTCATCGAAACCGTGTACCTGCGCACGCCCTTCTCGGCCGGCAACGCCACAACATAAAGAA
GCAAGCAACATCAACAACAGCTGCCGCCATGGGCTCCAGTGAGCAGGAACTGAAAGCCATTGTC
AAAGATCTTGGTTGTGGGCCATATTTTTTGGGCACCTATGACAAGCGCTTTCCAGGCTTTGTTTCT
```

```
CCACACAAGCTCGCCTGCGCCATAGTCAATACGGCCGGTCGCGAGACTGGGGGCGTACACTGG
ATGGCCTTTGCCTGGAACCCGCACTCAAAAACATGCTACCTCTTTGAGCCCTTTGGCTTTTCTGA
CCAGCGACTCAAGCAGGTTTACCAGTTTGAGTACGAGTCACTCCTGCGCCGTAGCGCCATTGCTT
CTTCCCCCGACCGCTGTATAACGCTGGAAAAGTCCACCCAAAGCGTACAGGGGCCCAACTCGGC
CGCCTGTGGACTATTCTGCTGCATGTTTCTCCAGGCCTTTGCCAACTGGCCCCAAACTCCCATGG
ATCACAACCCCACCATGAACCTTATTACCGGGGTACCCAACTCCATGCTCAACAGTCCCCAGGTA
CAGCCCACCCTGCGTCGCAACCAGGAACAGCTCTACAGCTTCCTGGAGCGCCACTCGCCCTACT
TCCGCAGCCACAGTGCGCAGATTAGGAGCGCCACTTCTTTTTGTCACTTGAAAAACATGTAAAAA
TAATGTACTAGAGACACTTTCAATAAAGGCAAATGCTTTTATTTGTACACTCTCGGGTGATTATTTA
CCCCCACCCTTGCCGTCTGCGCCGTTTAAAAATCAAAGGGGTTCTGCCGCGCATCGCTATGCGC
CACTGGCAGGGACACGTTGCGATACTGGTGTTTAGTGCTCCACTTAAACTCAGGCACAACCATCC
GCGGCAGCTCGGTGAAGTTTTCACTCCACAGGCTGCGCACCATCACCAACGCGTTTAGCAGGTC
GGGCGCCGATATCTTGAAGTCGCAGTTGGGGCCTCCGCCCTGCGCGCGCGAGTTGCGATACAC
AGGGTTGCAGCACTGGAACACTATCAGCGCCGGGTGGTGCACGCTGGCCAGCACGCTCTTGTC
GGAGATCAGATCCGCGTCCAGGTCCTCCGCGTTGCTCAGGGCGAACGGAGTCAACTTTGGTAGC
TGCCTTCCCAAAAAGGGCGCGTGCCCAGGCTTTGAGTTGCACTCGCACCGTAGTGGCATCAAAA
GGTGACCGTGCCCGGTCTGGGCGTTAGGATACAGCGCCTGCATAAAAGCCTTGATCTGCTTAAA
AGCCACCTGAGCCTTTGCGCCTTCAGAGAAGAACATGCCGCAAGACTTGCCGGAAAACTGATTG
GCCGGACAGGCCGCGTCGTGCACGCAGCACCTTGCGTCGGTGTTGGAGATCTGCACCACATTTC
GGCCCCACCGGTTCTTCACGATCTTGGCCTTGCTAGACTGCTCCTTCAGCGCGCGCTGCCCGTT
TTCGCTCGTCACATCCATTTCAATCACGTGCTCCTTATTTATCATAATGCTTCCGTGTAGACACTTA
AGCTCGCCTTCGATCTCAGCGCAGCGGTGCAGCCACAACGCGCAGCCCGTGGGCTCGTGATGC
TTGTAGGTCACCTCTGCAAACGACTGCAGGTACGCCTGCAGGAATCGCCCCATCATCGTCACAAA
GGTCTTGTTGCTGGTGAAGGTCAGCTGCAACCCGCGGTGCTCCTCGTTCAGCCAGGTCTTGCAT
ACGGCCGCCAGAGCTTCCACTTGGTCAGGCAGTAGTTTGAAGTTCGCCTTTAGATCGTTATCCAC
GTGGTACTTGTCCATCAGCGCGCGCGCAGCCTCCATGCCCTTCTCCCACGCAGACACGATCGGC
ACACTCAGCGGGTTCATCACCGTAATTTCACTTTCCGCTTCGCTGGGCTCTTCCTCTTCCTCTTGC
GTCCGCATACCACGCGCCACTGGGTCGTCTTCATTCAGCCGCCGCACTGTGCGCTTACCTCCTT
TGCCATGCTTGATTAGCACCGGTGGGTTGCTGAAACCCACCATTTGTAGCGCCACATCTTCTCTT
TCTTCCTCGCTGTCCACGATTACCTCTGGTGATGGCGGGCGCTCGGGCTTGGGAGAAGGGCGCT
TCTTTTTCTTCTTGGGCGCAATGGCCAAATCCGCCGCCGAGGTCGATGGCCGCGGGCTGGGTGT
GCGCGGCACCAGCGCGTCTTGTGATGAGTCTTCCTCGTCCTCGGACTCGATACGCCGCCTCATC
CGCTTTTTTGGGGGCGCCCGGGAGGCGGCGGCGACGGGACGGGGACGACACGTCCTCCAT
GGTTGGGGGACGTCGCGCCGCACCGCGTCCGCGCTCGGGGGTGGTTTCGCGCTGCTCCTCTTC
CCGACTGGCCATTTCCTTCTCCTATAGGCAGAAAAAGATCATGGAGTCAGTCGAGAAGAAGGACA
GCCTAACCGCCCCCTCTGAGTTCGCCACCACCGCCTCCACCGATGCCGCCAACGCGCCTACCAC
CTTCCCCGTCGAGGCACCCCCGCTTGAGGAGGAGGAAGTGATTATCGAGCAGGACCCAGGTTTT
GTAAGCGAAGACGACGAGGACCGCTCAGTACCAACAGAGGATAAAAAGCAAGACCAGGACAACG
CAGAGGCAAACGAGGAACAAGTCGGGCGGGGGACGAAAGGCATGGCGACTACCTAGATGTGG
GAGACGACGTGCTGTTGAAGCATCTGCAGCGCCAGTGCGCCATTATCTGCGACGCGTTGCAAGA
```

-continued

```
GCGCAGCGATGTGCCCCTCGCCATAGCGGATGTGAGCCTTGCCTACGAACGCCACCTATTCTCA
CCGCGCGTACCCCCCAAACGCCAAGAAAACGGCACATGCGAGCCCAACCCGCGCCTCAACTTCT
ACCCCGTATTTGCCGTGCCAGAGGTGCTTGCCACCTATCACATCTTTTTCCAAAACTGCAAGATA
CCCCTATCCTGCCGTGCCAACCGCAGCCGAGCGGACAAGCAGCTGGCCTTGCGGCAGGGCGCT
GTCATACCTGATATCGCCTCGCTCAACGAAGTGCCAAAAATCTTTGAGGGTCTTGGACGCGACGA
GAAGCGCGCGGCAAACGCTCTGCAACAGGAAAACAGCGAAAATGAAAGTCACTCTGGAGTGTTG
GTGGAACTCGAGGGTGACAACGCGCGCCTAGCCGTACTAAAACGCAGCATCGAGGTCACCCACT
TTGCCTACCCGGCACTTAACCTACCCCCCAAGGTCATGAGCACAGTCATGAGTGAGCTGATCGT
GCGCCGTGCGCAGCCCCTGGAGAGGGATGCAAATTTGCAAGAACAAACAGAGGAGGGCCTACC
CGCAGTTGGCGACGAGCAGCTAGCGCGCTGGCTTCAAACGCGCGAGCCTGCCGACTTGGAGGA
GCGACGCAAACTAATGATGGCCGCAGTGCTCGTTACCGTGGAGCTTGAGTGCATGCAGCGGTTC
TTTGCTGACCCGGAGATGCAGCGCAAGCTAGAGGAAACATTGCACTACACCTTTCGACAGGGCT
ACGTACGCCAGGCCTGCAAGATCTCCAACGTGGAGCTCTGCAACCTGGTCTCCTACCTTGGAATT
TTGCACGAAAACCGCCTTGGGCAAAACGTGCTTCATTCCACGCTCAAGGGCGAGGCGCGCCGC
GACTACGTCCGCGACTGCGTTTACTTATTTCTATGCTACACCTGGCAGACGGCCATGGGCGTTTG
GCAGCAGTGCTTGGAGGAGTGCAACCTCAAGGAGCTGCAGAAACTGCTAAAGCAAAACTTGAAG
GACCTATGGACGGCCTTCAACGAGCGCTCCGTGGCCGCGCACCTGGCGGACATCATTTTCCCCG
AACGCCTGCTTAAAACCCTGCAACAGGGTCTGCCAGACTTCACCAGTCAAAGCATGTTGCAGAAC
TTTAGGAACTTTATCCTAGAGCGCTCAGGAATCTTGCCCGCCACCTGCTGTGCACTTCCTAGCGA
CTTTGTGCCCATTAAGTACCGCGAATGCCCTCCGCCGCTTTGGGCCACTGCTACCTTCTGCAG
CTAGCCAACTACCTTGCCTACCACTCTGACATAATGGAAGACGTGAGCGGTGACGGTCTACTGGA
GTGTCACTGTCGCTGCAACCTATGCACCCCGCACCGCTCCCTGGTTTGCAATTCGCAGCTGCTTA
ACGAAAGTCAAATTATCGGTACCTTTGAGCTGCAGGGTCCCTCGCCTGACGAAAAGTCCGCGGC
TCCGGGGTTGAAACTCACTCCGGGGCTGTGGACGTCGGCTTACCTTCGCAAATTTGTACCTGAG
GACTACCACGCCCACGAGATTAGGTTCTACGAAGACCAATCCCGCCCGCCAAATGCGGAGCTTA
CCGCCTGCGTCATTACCCAGGGCCACATTCTTGGCCAATTGCAAGCCATCAACAAAGCCCGCCA
AGAGTTTCTGCTACGAAAGGGACGGGGGGTTTACTTGGACCCCCAGTCCGGCGAGGAGCTCAAC
CCAATCCCCCCGCCGCCGCAGCCCTATCAGCAGCAGCCGCGGGCCCTTGCTTCCCAGGATGGC
ACCCAAAAAGAAGCTGCAGCTGCCGCCGCCACCCACGGACGAGGAGGAATACTGGGACAGTCA
GGCAGAGGAGGTTTTGGACGAGGAGGAGGAGGACATGATGGAAGACTGGGAGAGCCTAGACGA
GGAAGCTTCCGAGGTCGAAGAGGTGTCAGACGAAACACCGTCACCCTCGGTCGCATTCCCCTCG
CCGGCGCCCCAGAAATCGGCAACCGGTTCCAGCATGGCTACAACCTCCGCTCCTCAGGCGCCG
CCGGCACTGCCCGTTCGCCGACCCAACCGTAGATGGGACACCACTGGAACCAGGGCCGGTAAG
TCCAAGCAGCCGCCGCCGTTAGCCCAAGAGCAACAACAGCGCCAAGGCTACCGCTCATGGCGC
GGGCACAAGAACGCCATAGTTGCTTGCTTGCAAGACTGTGGGGGCAACATCTCCTTCGCCCGCC
GCTTTCTTCTCTACCATCACGGCGTGGCCTTCCCCCGTAACATCCTGCATTACTACCGTCATCTCT
ACAGCCCATACTGCACCGGCGGCAGCGGCAGCGGCAGCAACAGCAGCGGCCACACAGAAGCAA
AGGCGACCGGATAGCAAGACTCTGACAAAGCCCAAGAAATCCACAGCGGCGGCAGCAGCAGGA
GGAGGAGCGCTGCGTCTGGCGCCCAACGAACCCGTATCGACCCGCGAGCTTAGAAACAGGATT
TTTCCCACTCTGTATGCTATATTTCAACAGAGCAGGGGCCAAGAACAAGAGCTGAAAATAAAAAAC
AGGTCTCTGCGATCCCTCACCCGCAGCTGCCTGTATCACAAAAGCGAAGATCAGCTTCGGCGCA
```

-continued

```
CGCTGGAAGACGCGGAGGCTCTCTTCAGTAAATACTGCGCGCTGACTCTTAAGGACTAGTTTCG
CGCCCTTTCTCAAATTTAAGCGCGAAAACTACGTCATCTCCAGCGGCCACACCCGGCGCCAGCA
CCTGTCGTCAGCGCCATTATGAGCAAGGAAATTCCCACGCCCTACATGTGGAGTTACCAGCCACA
AATGGGACTTGCGGCTGGAGCTGCCCAAGACTACTCAACCCGAATAAACTACATGAGCGCGGGA
CCCCACATGATATCCCGGGTCAACGGAATCCGCGCCCACCGAAACCGAATTCTCTTGGAACAGG
CGGCTATTACCACCACACCTCGTAATAACCTTAATCCCCGTAGTTGGCCCGCTGCCCTGGTGTAC
CAGGAAAGTCCCGCTCCCACCACTGTGGTACTTCCCAGAGACGCCCAGGCCGAAGTTCAGATGA
CTAACTCAGGGGCGCAGCTTGCGGGCGGCTTTCGTCACAGGGTGCGGTCGCCCGGGCAGGGTA
TAACTCACCTGACAATCAGAGGGCGAGGTATTCAGCTCAACGACGAGTCGGTGAGCTCCTCGCT
TGGTCTCCGTCCGGACGGGACATTTCAGATCGGCGGCGCCGGCCGTCCTTCATTCACGCCTCGT
CAGGCAATCCTAACTCTGCAGACCTCGTCCTCTGAGCCGCGCTCTGGAGGCATTGGAACTCTGC
AATTTATTGAGGAGTTTGTGCCATCGGTCTACTTTAACCCCTTCTCGGGACCTCCCGGCCACTAT
CCGGATCAATTTATTCCTAACTTTGACGCGGTAAAGGACTCGGCGGACGGCTACGACTGAATGTT
AAGTGGAGAGGCAGAGCAACTGCGCCTGAAACACCTGGTCCACTGTCGCCGCCACAAGTGCTTT
GCCCGCGACTCCGGTGAGTTTTGCTACTTTGAATTGCCCGAGGATCATATCGAGGGCCCGGCGC
ACGGCGTCCGGCTTACCGCCCAGGGAGAGCTTGCCCGTAGCCTGATTCGGGAGTTTACCCAGC
GCCCCCTGCTAGTTGAGCGGGACAGGGGACCCTGTGTTCTCACTGTGATTTGCAACTGTCCTAA
CCTTGGATTACATCAAGATCCTCTAGTTATAACTAGAGTACCCGGGGATCTTATTCCCTTTAACTA
ATAAAAAAAAATAATAAAGCATCACTTACTTAAAATCAGTTAGCAAATTTCTGTCCAGTTTATTCAG
GAGCACCTCCTTGCCCTCCTCCCAGCTCTGGTATTGCAGCTTCCTCCTGGCTGCAAACTTTCTCC
ACAATCTAAATGGAATGTCAGTTTCCTCCTGTTCCTGTCCATCCGCACCCACTATCTTCATGTTGT
TGCAGATGAAGCGCGCAAGACCGTCTGAAGATACCTTCAACCCCGTGTATCCATATGACACGGAA
ACCGGTCCTCCAACTGTGCCTTTTCTTACTCCTCCCTTTGTATCCCCAATGGGTTTCAAGAGAGT
CCCCCTGGGGTACTCTCTTTGCGCCTATCCGAACCTCTAGTTACCTCCAATGGCATGCTTGCGCT
CAAAATGGGCAACGGCCTCTCTCTGGACGAGGCCGGCAACCTTACCTCCCAAAATGTAACCACT
GTGAGCCCACCTCTCAAAAAAACCAAGTCAAACATAAACCTGGAAATATCTGCACCCCTCACAGT
TACCTCAGAAGCCCTAACTGTGGCTGCCGCCGCACCTCTAATGGTCGCGGGCAACACACTCACC
ATGCAATCAGAGGCCCCGCTAACCGTGCACGACTCCAAACTTAGCATTGCCACCCAAGGACCCC
TCACAGTGTCAGAAGGAAAGCTAGCCCTGCAAACATCAGGCCCCCTCACCACCACCGATAGCAG
TACCCTTACTATCACTGCCTCACCCCCTCTAACTACTGCCACTGGTAGCTTGGGCATTGACTTGAA
AGAGCCCATTTATACACAAAATGGAAAACTAGGACTAAAGTACGGGGCTCCTTTGCATGTAACAG
ACGACCTAAACACTTTGACCGTAGCAACTGGTCCAGGTGTGACTATTAATAATACTTCCTTGCAAA
CTAAAGTTACTGGAGCCTTGGGTTTTGATTCACAAGGCAATATGCAACTTAATGTAGCAGGAGGA
CTAAGGATTGATTCTCAAAACAGACGCCTTATACTTGATGTTAGTTATCCGTTTGATGCTCAAAAC
CAACTAAATCTAAGACTAGGACAGGGCCCTCTTTTTATAAACTCAGCCCACAACTTGGATATTAAC
TACAACAAAGGCCTTTACTTGTTTACAGCTTCAAACAATTCCAAAAAGCTTGAGGTTAACCTAAGC
ACTGCCAAGGGGTTGATGTTTGACGCTACAGCCATAGCCATTAATGCAGGAGATGGGCTTGAATT
TGGTTCACCTAATGCACCAAACACAAATCCCCTCAAAACAAAAATTGGCCATGGCCTAGAATTTGA
TTCAAACAAGGCTATGGTTCCTAAACTAGGAACTGGCCTTAGTTTTGACAGCACAGGTGCCATTA
CAGTAGGAAACAAAAATAATGATAAGCTAACTTTGTGGACCACACCAGCTCCATCTCCTAACTGTA
```

-continued

```
GACTAAATGCAGAGAAAGATGCTAAACTCACTTTGGTCTTAACAAAATGTGGCAGTCAAATACTTG
CTACAGTTTCAGTTTTGGCTGTTAAAGGCAGTTTGGCTCCAATATCTGGAACAGTTCAAAGTGCTC
ATCTTATTATAAGATTTGACGAAAATGGAGTGCTACTAAACAATTCCTTCCTGGACCCAGAATATT
GGAACTTTAGAAATGGAGATCTTACTGAAGGCACAGCCTATACAAACGCTGTTGGATTTATGCCTA
ACCTATCAGCTTATCCAAAATCTCACGGTAAAACTGCCAAAAGTAACATTGTCAGTCAAGTTTACT
TAAACGGAGACAAAACTAAACCTGTAACACTAACCATTACACTAAACGGTACACAGGAAACAGGA
GACACAACTCCAAGTGCATACTCTATGTCATTTTCATGGGACTGGTCTGGCCACAACTACATTAAT
GAAATATTTGCCACATCCTCTTACACTTTTTCATACATTGCCCAAGAATAAAGAATCGTTTGTGTTA
TGTTTCAACGTGTTTATTTTTCAATTGCAGAAAATTTCAAGTCATTTTTCATTCAGTAGTATAGCCC
CACCACCACATAGCTTATACAGATCACCGTACCTTAATCAAAC
``` pSSI10902 (SEQ ID NO: 2):

```
AATGTAGTCTTATGCAATACTCTTGTAGTCTTGCAACATGGTAACGATGAGTTAGCAACATGCCTT
ACAAGGAGAGAAAAAGCACCGTGCATGCCGATTGGTGGAAGTAAGGTGGTACGATCGTGCCTTA
TTAGGAAGGCAACAGACGGGTCTGACATGGATTGGACGAACCACTGAATTGCCGCATTGCAGAG
ATATTGTATTTAAGTGCCTAGCTCGATACATAAACGGGTCTCTCGGTTAGACCAGATCTGAGCCT
GGGAGCTCTCTGGCTAACTAGGGAACCCACTGCTTAAGCCTCAATAAAGCTTGCCTTGAGTGCTT
CAAGTAGTGTGTGCCCGTCTGTTGTGTGACTCTGGTAACTAGAGATCCCTCAGACCCTTTTAGTC
AGTGTGGAAAATCTCTAGCAGTGGCGCCCGAACAGGGACTTGAAAGCGAAAGGGAAACCAGAGG
AGCTCTCTCGACGCAGGACTCGGCTTGCTGAAGCGCGCACGGCAAGAGGCGAGGGGCGGCGA
CTGGTGAGTACGCCAAAAATTTTGACTAGCGGAGGCTAGAAGGAGAGAGATGGGTGCGAGAGCG
TCAGTATTAAGCGGGGGAGAATTAGATCGCGATGGGAAAAAATTCGGTTAAGGCCAGGGGGAAA
GAAAAAATATAAATTAAAACATATAGTATGGGCAAGCAGGGAGCTAGAACGATTCGCAGTTAATCC
TGGCCTGTTAGAAACATCAGAAGGCTGTAGACAAATACTGGGACAGCTACAACCATCCCTTCAGA
CAGGATCAGAAGAACTTAGATCATTATATAATACAGTAGGAACCCTCTATTGTGTGCATCAAAGGA
TAGAGATAAAAGACACCAAGGAAGCTTTAGACAAGATAGAGGAAGAGCAAAACAAAAGTAAGACC
ACCGCACAGCAAGCGGCCGCTGATCTTCAGACCTGGAGGAGGAGATATGAGGGACAATTGGAG
AAGTGAATTATATAAATATAAGTAGTAAAAATTGAACCATTAGGAGTAGCACCCACCAAGGCAAA
GAGAAGAGTGGTGCAGAGAGAAAAAAGAGGAGTGGGAATAGGAGCTTTGTTCCTTGGGTTCTTG
GGAGCAGCAGGAAGCACTATGGGCGCAGCGTCAATGACGCTGACGGTACAGGCCAGACAATTAT
TGTCTGGTATAGTGCAGCAGCAGAACAATTTGCTGAGGGCTATTGAGGCGCAACAGCATCTGTTG
CAACTCACAGTCTGGGGCATCAAGCAGCTCCAGGCAAGAATCCTGGCTGTGGAAAGATACCTAA
AGGATCAACAGCTCCTGGGGATTTGGGGTTGCTCTGGAAAACTCATTTGCACCACTGCTGTGCCT
TGGAATGCTAGTTGGAGTAATAAATCTCTGGAACAGATTTGGAATCACACGACCTGGATGGAGTG
GGACAGAGAAATTAACAATTACACAAGCTTAATACACTCCTTAATTGAAGAATCGCAAACCAGCA
AGAAAAGAATGAACAAGAATTATTGGAATTAGATAAATGGGCAAGTTTGTGGAATTGGTTTAACAT
AACAAATTGGCTGTGGTATATAAAATTATTCATAATGATAGTAGGAGGCTTGGTAGGTTTAAGAAT
AGTTTTTGCTGTACTTTCTATAGTGAATAGAGTTAGGCAGGGATATTCACCATTATCGTTTCAGAC
CCACCTCCCAACCCCGAGGGGACCCGACAGGCCCGAAGGAATAGAAGAAGAAGGTGGAGAGAG
AGACAGAGACAGATCCATTCGATTAGTGAACGGATCTCGACGGTATCGATTGGGCCCGAGATCT
CGCGCGCGAGGCCTGCCATGGGCATGCCTGCAGGTCGATGCGTGGCCGGCCTAGGATCCATAT
GGTACCGGTAAATGGCCCGCCTGGCTGACCGCCCAACGACCCCCGCCCATTGACGTCAATAATG
```

-continued

```
ACGTATGTTCCCATAGTAACGCCAATAGGGACTTTCCATTGACGTCAATGGGTGGAGTATTTACG

GTAAACTGCCCACTTGGCAGTACATCAAGTGTATCATATGCCAAGTACGCCCCCTATTGACGTCA

ATGACGGTAAATGGCCCGCCTGGCATTATGCCCAGTACATGACCTTATGGGACTTTCCTACTTGG

CAGTACATCTAGTATTAGTCATCGCTATTACCATGGTGATGCGGTTTTGGCAGTACATCAATGGGC

GTGGATAGCGGTTTGACTCACGGGGATTTCCAAGTCTCCACCCCATTGACGTCAATGGGAGTTTG

TTTTGGCACCAAAATCAACGGGACTTTCCAAAATGTCGTAACAACTCCGCCCCATTGACGCAAAT

GGGCGGTAGGCGTGTACGGTGGGAGGTCTATATAAGCAGAGCTCGTTTAGTGAACCGTCAGATC

GCCTGGAGACGCCATCCACGCTGTTTTGACCTCCATAGAAGACACCGGGACCGATCCAGCCTCC

GCGGCCGGGAACGGTGCATTGGAACGCGGATTCCCCGTGCCAAGAGTGACGTAAGTACCGCCT

ATAGACTCTATAGGCACACCCCTTTGGCTCTTATGCATGAATTAATAGGACTCACTATAGGGAGAC

AGACTGTTCCTTTCCTGGGTCTTTTCTGCAGGCTAGCCCCACCATGCCGCGCGCTCCCCGCTGC

CGAGCCGTGCGCTCCCTGCTGCGCAGCCACTACCGCGAGGTGCTGCCGCTGGCCACGTTCGTG

CGGCGCCTGGGCCCCAGGGCTGGCGGCTGGTGCAGCGCGGGGACCCGGCGGCTTTCCGCG

CGCTGGTGGCCCAGTGCCTGGTGTGCGTGCCCTGGGACGCACGGCCGCCCCCCGCCGCCCCC

TCCTTCCGCCAGGTGTCCTGCCTGAAGGAGCTGGTGGCCCGAGTGCTGCAGAGGCTGTGCGAG

CGCGGCGCGAAGAACGTGCTGGCCTTCGGCTTCGCGCTGCTGGACGGGGCCCGCGGGGGCCC

CCCCGAGGCCTTCACCACCAGCGTGCGCAGCTACCTGCCCAACACGGTGACCGACGCACTGCG

GGGGAGCGGGGCGTGGGGGCTGCTGTTGCGCCGCGTGGGCGACGACGTGCTGGTTCACCTGC

TGGCACGCTGCGCGCTCTTTGTGCTGGTGGCTCCCAGCTGCGCCTACCAGGTGTGCGGGCCGC

CGCTGTACCAGCTCGGCGCTGCCACTCAGGCCCGGCCCCCGCCACACGCTAGTGGACCCCGAA

GGCGTCTGGGATGCGAACGGGCCTGGAACCATAGCGTCAGGGAGGCCGGGGTCCCCCTGGGC

CTGCCAGCCCCGGGTGCGAGGAGGCGCGGGGGCAGTGCCAGCCGAAGTCTGCCGTTGCCCAA

GAGGCCCAGGCGTGGCGCTGCCCCTGAGCCGGAGCGGACGCCCGTTGGGCAGGGGTCCTGGG

CCCACCCGGGCAGGACGCGTGGACCGAGTGACCGTGGTTTCTGTGTGGTGTCACCTGCCAGAC

CCGCCGAAGAAGCCACCTCTTTGGAGGGTGCGCTCTCTGGCACGCGCCACTCCCACCCATCCGT

GGGCCGCCAGCACCACGCGGGCCCCCCATCCACATCGCGGCCACCACGTCCCTGGGACACGC

CTTGTCCCCGGTGTACGCCGAGACCAAGCACTTCCTCTACTCCTCAGGCGACAAGGAGCAGCT

GCGGCCCTCCTTCCTACTCAGCTCTCTGAGGCCCAGCCTGACTGGCGCTCGGAGGCTCGTGGA

GACCATCTTTCTGGGTTCCAGGCCCTGGATGCCAGGGACTCCCCGCAGGTTGCCCCGCCTGCC

CCAGCGCTACTGGCAAATGCGGCCCCTGTTTCTGGAGCTGCTTGGGAACCACGCGCAGTGCCC

CTACGGGGTGCTCCTCAAGACGCACTGCCCGCTGCGAGCTGCGGTCACCCCAGCAGCCGGTGT

CTGTGCCCGGGAGAAGCCCCAGGGCTCTGTGGCGGCCCCGAGGAGGAGGACACAGACCCCC

GTCGCCTGGTGCAGCTGCTCCGCCAGCACAGCAGCCCCTGGCAGGTGTACGGCTTCGTGCGGG

CCTGCCTGCGCCGGCTGGTGCCCCAGGCCTCTGGGGCTCCAGGCACAACGAACGCCGCTTCC

TCAGGAACACCAAGAAGTTCATCTCCCTGGGGAAGCATGCCAAGCTCTCGCTGCAGGAGCTGAC

GTGGAAGATGAGCGTGCGGGCTGCGCTTGGCTGCGCAGGAGCCCAGGGGTTGGCTGTGTTCC

GGCCGCAGAGCACCGTCTGCGTGAGGAGATCCTGGCCAAGTTCCTGCACTGGCTGATGAGTGT

GTACGTCGTCGAGCTGCTCAGGTCTTTCTTTTATGTCACGGAGACCACGTTTCAAAAGAACAGGC

TCTTTTTCTACCGGAAGAGTGTCTGGAGCAAGTTGCAAAGCATTGGAATCAGACAGCACTTGAAG

AGGGTGCAGCTGCGGGAGCTGTCGGAAGCAGAGGTCAGGCAGCATCGGGAAGCCAGGCCCGC

CCTGCTGACGTCCAGACTCCGCTTCATCCCCAAGCCTGACGGGCTGCGGCCGATTGTGAACATG
```

-continued

```
GACTACGTCGTGGGAGCCAGAACGTTCCGCAGAGAAAAGAGGGCCGAGCGTCTCACCTCCAGG

GTGAAGGCACTGTTCAGCGTGCTCAACTACGAGCGGGCGCGGCGCCCCGGCCTCCTGGGCGCC

TCTGTGCTGGGCCTGGACGATATCCACAGGGCCTGGCGCACCTTCGTGCTGCGTGTGCGGGCC

CAGGACCCGCCGCCTGAGCTGTACTTTGTCAAGGTGGATGTGACGGGCGCGTACGACACCATCC

CCCAGGACAGGCTCACGGAGGTCATCGCCAGCATCATCAAACCCCAGAACACGTACTGCGTGCG

TCGGTATGCCGTGGTCCAGAAGGCCGCCCATGGGCACGTCCGCAAGGCCTTCAAGAGCCACGT

CTCTACCTTGACAGACCTCCAGCCGTACATGCGACAGTTCGTGGCTCACCTGCAGGAGACCAGC

CCGCTGAGGGATGCCGTCGTCATCGAGCAGAGCTCCTCCCTGAATGAGGCCAGCAGTGGCCTC

TTCGACGTCTTCCTACGCTTCATGTGCCACCACGCCGTGCGCATCAGGGGCAAGTCCTACGTCC

AGTGCCAGGGGATCCCGCAGGGCTCCATCCTCTCCACGCTGCTCTGCAGCCTGTGCTACGGCG

ACATGGAGAACAAGCTGTTTGCGGGGATTCGGCGGGACGGGCTGCTCCTGCGTTTGGTGGATG

ATTTCTTGTTGGTGACACCTCACCTCACCCACGCGAAAACCTTCCTCAGGACCCTGGTCCGAGGT

GTCCCTGAGTATGGCTGCGTGGTGAACTTGCGGAAGAGAGTGGTGAACTTCCCTGTAGAAGACG

AGGCCCTGGGTGGCACGGCTTTTGTTCAGATGCCGGCCCACGGCCTATTCCCTGGTGCGGCC

TGCTGCTGGATACCCGGACCCTGGAGGTGCAGAGCGACTACTCCAGCTATGCCCGGACCTCCAT

CAGAGCCAGTCTCACCTTCAACCGCGGCTTCAAGGCTGGGAGGAACATGCGTCGCAAACTCTTT

GGGGTCTTGCGGCTGAAGTGTCACAGCCTGTTTCTGGATTTGCAGGTGAACAGCCTCCAGACGG

TGTGCACCAACATCTACAAGATCCTCCTGCTGCAGGCGTACAGGTTTCACGCATGTGTGCTGCAG

CTCCCATTTCATCAGCAAGTTTGGAAGAACCCCACATTTTTCCTGCGCGTCATCTCTGACACGGC

CTCCCTCTGCTACTCCATCCTGAAAGCCAAGAACGCAGGGATGTCGCTGGGGGCCAAGGGCGC

CGCCGGCCCTCTGCCCTCCGAGGCCGTGCAGTGGCTGTGCCACCAAGCATTCCTGCTCAAGCT

GACTCGACACCGTGTCACCTACGTGCCACTCCTGGGGTCACTCAGGACAGCCCAGACGCAGCTG

AGTCGGAAGCTCCCGGGGACGACGCTGACTGCCCTGGAGGCCGCAGCCAACCCGGCACTGCC

CTCAGACTTCAAGACCATCCTGGACTGAGTCGAAACTCGAGGATCCGGCTGTGGAATGTGTGTC

AGTTAGGGTGTGGAAAGTCCCCAGGCTCCCCAGCAGGCAGAAGTATGCAAAGCATGCATCTCAA

TTAGTCAGCAACCAGGTGTGGAAAGTCCCCAGGCTCCCCAGCAGGCAGAAGTATGCAAAGCATG

CATCTCAATTAGTCAGCAACCATAGTCCCGCCCCTAACTCCGCCCATCCCGCCCCTAACTCCGCC

CAGTTCCGCCCATTCTCCGCCCCATGGCTGACTAATTTTTTTTATTTATGCAGAGGCCGAGGCCG

CCTCGGCCTCTGAGCTATTCCAGAAGTAGTGAGGAGGCTTTTTTGGAGGCCGTCGGCCGCCACG

ACCGGTGCCGCCACCATCCCCTGACCCACGCCCCTGACCCCTCACAAGGAGACGACCTTCCATG

ACCGAGTACAAGCCCACGGTGCGCCTCGCCACCCGCGACGACGTCCCCGGGCCGTACGCACC

CTCGCCGCCGCGTTCGCCGACTACCCTGCAACACGCCATACAGTGGACCCTGACCGCCACATCG

AGCGGGTCACCGAGCTGCAAGAACTCTTCCTCACGCGCGTCGGGCTCGACATCGGCAAGGTGT

GGGTCGCGGACGACGGCGCCGCGGTGGCGGTCTGGACCACGCCGGAGAGCGTCGAAGCGGG

GGCGGTGTTCGCCGAGATCGGCCCGCGCATGGCCGAGTTGAGCGGTTCCCGGCTGGCCGCGC

AGCAACAGATGGAAGGCCTCCTGGCGCCGCACCGGCCCAAGGAGCCCGCGTGGTTCCTGGCCA

CCGTCGGCGTCTCGCCCGACCACCAGGGCAAGGGTCTGGGCAGCGCCGTCGTGCTCCCCGGA

GTGGAGGCGGCCGAGCGCGCCGGGGTGCCCGCCTTCCTGGAGACCTCCGCGCCCCGCAACCT

CCCCTTCTACGAGCGGCTCGGCTTCACCGTCACCGCCGACGTCGAGGTGCCCGAAGGACCGCG

CACCTGGTGCATGACCCGCAAGCCCGGTGCCTGACGCCCGCCCCACGACCCGCAGCGCCCGAC
```

-continued

```
CGAAAGGAGGGCACGACCCCATGCATCGATAAAATAAAAGATTTTATTTAGTCTCCAGAAAAGG

GGGGAATGAAAGACCCCACCTGTAGGTTTGGCAAGCTAGGCCTATTAATATTCCGGAGTATACGT

AGCCGGCTAACGTTAACAACCGGTACGATGCATTAGTTATTAATAGTAATCAATTACGGGTCATT

AGTTCATAGCCCATATATGGAGTTCCGCGTTACATAACTTACGGTAAATGGCCCGCCTGGCTGAC

CGCCCAACGACCCCCGCCCATTGACGTCAATAATGACGTATGTTCCCATAGTAACGCCAATAGGG

ACTTTCCATTGACGTCAATGGGTGGAGTATTTACGGTAAACTGCCCACTTGGCAGTACATCAAGT

GTATCATATGCCAAGTACGCCCCCTATTGACGTCAATGACGGTAAATGGCCCGCCTGGCATTATG

CCCAGTACATGACCTTATGGGACTTTCCTACTTGGCAGTACATCTACGTATTAGTCATCGCTATTA

CCATGGTGATGCGGTTTTGGCAGTACATCAATGGGCGTGGATAGCGGTTTGACTCACGGGGATT

TCCAAGTCTCCACCCCATTGACGTCAATGGGAGTTTGTTTTGGCACCAAAATCAACGGGACTTTC

CAAAATGTCGTAACAACTCCGCCCCATTGACGCAAATGGGCGGTAGGCGTGTACGGTGGGAGGT

CTATATAAGCAGAGCTGGTTTAGTGAACCGTCAGATCCGCTAGCGCTACCGGACTCAGATCTCGA

GCTCAAGCTTCGAATTCTGCAGTCGACCCACCATGGCTCTTTCAAACAAGTTTATCGGAGATGAC

ATGAAAATGACCTACCATATGGATGGCTGTGTCAATGGGCATTACTTTACCGTCAAAGGTGAAGG

CAGCGGGAAGCCATACGAAGGGACGCAGACCTCGACTTTTAAAGTCACCATGGCCAACGGTGGG

CCCCTTGCATTCTCCTTTGACATACTATCTACAGTGTTCATGTATGGAAATCGATGCTTTACTGCG

TATCCTACCAGTATGCCCGACTATTTCAAACAAGCATTTCCTGACGGAATGTCATATGAAAGGACT

TTTACCTATGAAGATGGAGGAGTTGCTACAGCCAGTTGGGAAATAAGCCTTAAAGGCAACTGCTT

TGAGCACAAATCCACGTTTCATGGAGTGAACTTTCCTGCTGATGGACCTGTGATGGCGAAGATGA

CAACTGGTTGGGACCCATCTTTTGAGAAAATGACTGTCTGCGATGGAATATTGAAGGGTGATGTC

ACCGCGTTCCTCATGCTGCAAGGAGGTGGCAATTACAGATGCCAATTCCACACTTCTTACAAGAC

AAAAAAACCGGTGACGATGCCACCAAACCATGCGGTGGAACATCGCATTGCGAGGACCGACCTT

GACAAAGGTGGCAACAGTGTTCAGCTGACGGAGCACGCTGTTGCACATATAACCTCTGTTGTCCC

TTTCTAGCGGCCGCGATAATCAACCTCTGGATTACAAAATTTGTGAAAGATTGACTGGTATTCTTA

ACTATGTTGCTCCTTTTACGCTATGTGGATACGCTGCTTTAATGCCTTTGTATCATGCTATTGCTTC

CCGTATGGCTTTCATTTTCTCCTCCTTGTATAAATCCTGGTTGCTGTCTCTTTATGAGGAGTTGTG

GCCCGTTGTCAGGCAACGTGGCGTGGTGTGCACTGTGTTTGCTGACGCAACCCCCACTGGTTGG

GGCATTGCCACCACCTGTCAGCTCCTTTCCGGGACTTTCGCTTTCCCCCTCCCTATTGCCACGGC

GGAACTCATCGCCGCCTGCCTTGCCCGCTGCTGGACAGGGGCTCGGCTGTTGGGCACTGACAA

TTCCGTGGTGTTGTCGGGGAAGCTGACGTCCTTTCCATGGCTGCTCGCCTGTGTTGCCACCTGG

ATTCTGCGCGGGACGTCCTTCTGCTACGTCCCTTCGGCCCTCAATCCAGCGGACCTTCCTTCCC

GCGGCCTGCTGCCGGCTCTGCGGCCTCTTCCGCGTCTTCGCCTTCGCCCTCAGACGAGTCGGA

TCTCCCTTTGGGCCGCCTCCCCGCATCGGACGCGTGGTACCTTTAAGACCAATGACTTACAAGG

CAGCTGTAGATCTTAGCCACTTTTTAAAAGAAAAGGGGGGACTGGAAGGGCTAATTCACTCCCAA

CGAAGACAAGATCTGCTTTTTGCTTGTACTGGGTCTCTCTGGTTAGACCAGATCTGAGCCTGGGA

GCTCTCTGGCTAACTAGGGAACCCACTGCTTAAGCCTCAATAAAGCTTGCCTTGAGTGCTTCAAG

TAGTGTGTGCCCGTCTGTTGTGTGACTCTGGTAACTAGAGATCCCTCAGACCCTTTTAGTCAGTG

TGGAAAATCTCTAGCAGTAGTAGTTCATGTCATCTTATTATTCAGTATTTATAACTTGCAAAGAAAT

GAATATCAGAGAGTGAGAGGAACTTGTTTATTGCAGCTTATAATGGTTACAAATAAAGCAATAGCA

TCACAAATTTCACAAATAAAGCATTTTTTTCACTGCATTCTAGTTGTGGTTTGTCCAAACTCATCAA

TGTATCTTATCATGTCTGGCTCTAGCTATCCCGCCCCTAACTCCGCCCATCCCGCCCCTAACTCC
```

```
GCCCAGTTCCGCCCATTCTCCGCCCCATGGCTGACTAATTTTTTTTATTTATGCAGAGGCCGAGG

CCGCCTCGGCCTCTGAGCTATTCCAGAAGTAGTGAGGAGGCTTTTTTGGAGGCCTAGGGACGTA

CCCAATTCGCCCTATAGTGAGTCGTATTACGCGCGCTCACTGGCCGTCGTTTTACAACGTCGTGA

CTGGGAAAACCCTGGCGTTACCCAACTTAATCGCCTTGCAGCACATCCCCCTTTCGCCAGCTGG

CGTAATAGCGAAGAGGCCCGCACCGATCGCCCTTCCCAACAGTTGCGCAGCCTGAATGGCGAAT

GGGACGCGCCCTGTAGCGGCGCATTAAGCGCGGCGGGTGTGGTGGTTACGCGCAGCGTGACC

GCTACACTTGCCAGCGCCCTAGCGCCCGCTCCTTTCGCTTTCTTCCCTTCCTTTCTCGCCACGTT

CGCCGGCTTTCCCCGTCAAGCTCTAAATCGGGGGCTCCCTTTAGGGTTCCGATTTAGTGCTTTAC

GGCACCTCGACCCCAAAAAACTTGATTAGGGTGATGGTTCACGTAGTGGGCCATCGCCCTGATA

GACGGTTTTTCGCCCTTTGACGTTGGAGTCCACGTTCTTTAATAGTGGACTCTTGTTCCAAACTGG

AACAACACTCAACCCTATCTCGGTCTATTCTTTTGATTTATAAGGGATTTTGCCGATTTCGGCCTAT

TGGTTAAAAAATGAGCTGATTTAACAAAAATTTAACGCGAATTTTAACAAAATATTAACGCTTACAA

TTTAGGTGGCACTTTTCGGGGAAATGTGCGCGGAACCCCTATTTGTTTATTTTTCTAAATACATTC

AAATATGTATCCGCTCATGAGACAATAACCCTGATAAATGCTTCAATAATATTGAAAAAGGAAGAG

TATGAGTATTCAACATTTCCGTGTCGCCCTTATTCCCTTTTTTGCGGCATTTTGCCTTCCTGTTTTT

GCTCACCCAGAAACGCTGGTGAAAGTAAAAGATGCTGAAGATCAGTTGGGTGCACGAGTGGGTT

ACATCGAACTGGATCTCAACAGCGGTAAGATCCTTGAGAGTTTTCGCCCCGAAGAACGTTTTCCA

ATGATGAGCACTTTTAAAGTTCTGCTATGTGGCGCGGTATTATCCCGTATTGACGCCGGGCAAGA

GCAACTCGGTCGCCGCATACACTATTCTCAGAATGACTTGGTTGAGTACTCACCAGTCACAGAAA

AGCATCTTACGGATGGCATGACAGTAAGAGAATTATGCAGTGCTGCCATAACCATGAGTGATAAC

ACTGCGGCCAACTTACTTCTGACAACGATCGGAGGACCGAAGGAGCTAACCGCTTTTTTGCACAA

CATGGGGGATCATGTAACTCGCCTTGATCGTTGGGAACCGGAGCTGAATGAAGCCATACCAAAC

GACGAGCGTGACACCACGATGCCTGTAGCAATGGCAACAACGTTGCGCAAACTATTAACTGGCG

AACTACTTACTCTAGCTTCCCGGCAACAATTAATAGACTGGATGGAGGCGGATAAAGTTGCAGGA

CCACTTCTGCGCTCGGCCCTTCCGGCTGGCTGGTTTATTGCTGATAAATCTGGAGCCGGTGAGC

GTGGGTCTCGCGGTATCATTGCAGCACTGGGGCCAGATGGTAAGCCCTCCCGTATCGTAGTTAT

CTACACGACGGGGAGTCAGGCAACTATGGATGAACGAAATAGACAGATCGCTGAGATAGGTGCC

TCACTGATTAAGCATTGGTAACTGTCAGACCAAGTTTACTCATATATACTTTAGATTGATTTAAAAC

TTCATTTTTAATTTAAAAGGATCTAGGTGAAGATCCTTTTTGATAATCTCATGACCAAAATCCCTTA

ACGTGAGTTTTCGTTCCACTGAGCGTCAGACCCCGTAGAAAAGATCAAAGGATCTTCTTGAGATC

CTTTTTTTCTGCGCGTAATCTGCTGCTTGCAAACAAAAAAACCACCGCTACCAGCGGTGGTTTGTT

TGCCGGATCAAGAGCTACCAACTCTTTTTCCGAAGGTAACTGGCTTCAGCAGAGCGCAGATACCA

AATACTGTTCTTCTAGTGTAGCCGTAGTTAGGCCACCACTTCAAGAACTCTGTAGCACCGCCTAC

ATACCTCGCTCTGCTAATCCTGTTACCAGTGGCTGCTGCCAGTGGCGATAAGTCGTGTCTTACCG

GGTTGGACTCAAGACGATAGTTACCGGATAAGGCGCAGCGGTCGGGCTGAACGGGGGGTTCGT

GCACACAGCCCAGCTTGGAGCGAACGACCTACACCGAACTGAGATACCTACAGCGTGAGCTATG

AGAAAGCGCCACGCTTCCCGAAGGGAGAAAGGCGGACAGGTATCCGGTAAGCGGCAGGGTCGG

AACAGGAGAGCGCACGAGGGAGCTTCCAGGGGGAAACGCCTGGTATCTTTATAGTCCTGTCGGG

TTTCGCCACCTCTGACTTGAGCGTCGATTTTTGTGATGCTCGTCAGGGGGGCGGAGCCTATGGA

AAAACGCCAGCAACGCGGCCTTTTTACGGTTCCTGGCCTTTTGCTGGCCTTTTGCTCACATGTTC
```

-continued

TTTCCTGCGTTATCCCTGATTCTGTGGATAACCGTATTACCGCCTTTGAGTGAGCTGATACCGCT

CGCCGCAGCCGAACGACCGAGCGCAGCGAGTCAGTGAGCGAGGAAGCGGAAGAGCGCCCAAT

ACGCAAACCGCCTCTCCCCGCGCGTTGGCCGATTCATTAATGCAGCTGGCACGACAGGTTTCCC

GACTGGAAAGCGGGCAGTGAGCGCAACGCAATTAATGTGAGTTAGCTCACTCATTAGGCACCCC

AGGCTTTACACTTTATGCTTCCGGCTCGTATGTTGTGTGGAATTGTGAGCGGATAACAATTTCACA

CAGGAAACAGCTATGACCATGATTACGCCAAGCGCGCAATTAACCCTCACTAAAGGGAACAAAAG

CTGGAGCTGCAAGCTT pSSI12112 (SEQ ID NO: 3):
AATGTAGTCTTATGCAATACTCTTGTAGTCTTGCAACATGGTAACGATGAGTTAGCAACATGCCTT

ACAAGGAGAGAAAAAGCACCGTGCATGCCGATTGGTGGAAGTAAGGTGGTACGATCGTGCCTTA

TTAGGAAGGCAACAGACGGGTCTGACATGGATTGGACGAACCACTGAATTGCCGCATTGCAGAG

ATATTGTATTTAAGTGCCTAGCTCGATACATAAACGGGTCTCTCTGGTTAGACCAGATCTGAGCCT

GGGAGCTCTCTGGCTAACTAGGGAACCCACTGCTTAAGCCTCAATAAAGCTTGCCTTGAGTGCTT

CAAGTAGTGTGTGCCCGTCTGTTGTGTGACTCTGGTAACTAGAGATCCCTCAGACCCTTTTAGTC

AGTGTGGAAAATCTCTAGCAGTGGCGCCCGAACAGGGACTTGAAAGCGAAAGGGAAACCAGAGG

AGCTCTCTCGACGCAGGACTCGGCTTGCTGAAGCGCGCACGGCAAGAGGCGAGGGGCGGCGA

CTGGTGAGTACGCCAAAAATTTTGACTAGCGGAGGCTAGAAGGAGAGAGATGGGTGCGAGAGCG

TCAGTATTAAGCGGGGGAGAATTAGATCGCGATGGGAAAAAATTCGGTTAAGGCCAGGGGGAAA

GAAAAAATATAAATTAAAACATATAGTATGGGCAAGCAGGGAGCTAGAACGATTCGCAGTTAATCC

TGGCCTGTTAGAAACATCAGAAGGCTGTAGACAAATACTGGGACAGCTACAACCATCCCTTCAGA

CAGGATCAGAAGAACTTAGATCATTATATAATACAGTAGCAACCCTCTATTGTGTGCATCAAAGGA

TAGAGATAAAAGACACCAAGGAAGCTTTAGACAAGATAGAGGAAGAGCAAAACAAAAGTAAGACC

ACCGCACAGCAAGCGGCCGCTGATCTTCAGACCTGGAGGAGGAGATATGAGGGACAATTGGAG

AAGTGAATTATATAAATATAAAGTAGTAAAAATTGAACCATTAGGAGTAGCACCCACCAAGGCAAA

GAGAAGAGTGGTGCAGAGAGAAAAAAGAGCAGTGGGAATAGGAGCTTTGTTCCTTGGGTTCTTG

GGAGCAGCAGGAAGCACTATGGGCGCAGCGTCAATGACGCTGACGGTACAGGCCAGACAATTAT

TGTCTGGTATAGTGCAGCAGCAGAACAATTTGCTGAGGGCTATTGAGGCGCAACAGCATCTGTTG

CAACTCACAGTCTGGGGCATCAAGCAGCTCCAGGCAAGAATCCTGGCTGTGGAAAGATACCTAA

AGGATCAACAGCTCCTGGGGATTTGGGGTTGCTCTGGAAAACTCATTTGCACCACTGCTGTGCCT

TGGAATGCTAGTTGGAGTAATAAATCTCTGGAACAGATTTGGAATCACACGACCTGGATGGAGTG

GGACAGAGAAATTAACAATTACACAAGCTTAATACACTCCTTAATTGAAGAATCGCAAAACCAGCA

AGAAAAGAATGAACAAGAATTATTGGAATTAGATAAATGGGCAAGTTTGTGGAATTGGTTTAACAT

AACAAATTGGCTGTGGTATATAAAATTATTCATAATGATAGTAGGAGGCTTGGTAGGTTTAAGAAT

AGTTTTTGCTGTACTTTCTATAGTGAATAGAGTTAGGCAGGGATATTCACCATTATCGTTTCAGAC

CCACCTCCCAACCCCGAGGGGACCCGAGAGGCCCGAAGGAATAGAAGAAGAAGGTGGAGAGAG

AGACAGAGACAGATCCATTCGATTAGTGAACGGATCTCGACGGTATCGATACTAGTAATTTTCTG

CAGAAAACGTACCCGGGGATCCTCTAGGATCCCACCGAAAGGTTGCTCCTTAACACAGGCTAAG

GACCAGCTTCTTTGGGAGAGAACAGACGCAGGGGCGGGAGGGAAAAAGGGAGAGGCAGACGTC

ACTTCCCCTTGGCGGCTCTGGCAGCAGATTGGTCGGTTGAGTGGCAGAAAGGCAGACGGGGAC

TGGGCAAGGCACTGTCGGTGACATCACGGACAGGGCGACTTCTATGTAGATGAGGCAGCGCAG

AGGCTGCTGCTTCGCCACTTGCTGCTTCGCCACGAAGGAGTTCCCGTGCCCTGGGAGCGGGTTC

-continued

```
AGGACCGCGGATCGGAAGTGAGAATCCCAGCTGTGTGTCAGGGCTGGAAAGGGCTCGGGAGTG

CGCGGGGCAAGTGACCGTGTGTGTAAAGAGTGAGGCGTATGAGGCTGTGTCGGGGCAGAGCCC

GAAGATCCGGGTTGCGGAGGGTGGGCCTGGGAGGGGTGGTGGCCATTTTTTGTCTAACCCTAAC

TGAGAAGGGCGTAGGCGCCGTGCTTTTGCTCCCCGCGCGCTGTTTTTCTCGCTGACTTTCAGCG

GGCGGAAAAGCCTCGGCCTGCCGCCTTCCACCGTTCATTCTAGAGCAAACAAAAAATGTCAGCT

GCTGGCCCGTTCGCCCCTCCCGGGGACCTGCGGCGGGTCGCCTGCCCAGCCCCCGAACCCCG

CCTGGAGGCCGCGGTCGGCCCGGGGCTTCTCCGGAGGCACCCACTGCCACCGCGAAGAGTTG

GGCTCTGTCAGCCGCGGGTCTCTCGGGGGCGAGGGCGAGGTTCAGGCCTTTCAGGCCGCAGG

AAGAGGAACGGAGCGAGTCCCCGCGCGCGGCGCGATTCCCTGAGCTGTGGGACGTGCACCCA

GGACTCGGCTCACACATGCAGTTCGCTTTCCTGTTGGTGGGGGGAACGCCGATCGTGCGCATCC

GTCACCCCTCGCCGGCAATGGGGGCTTGTGAACCCCCAAACCTGACTGACTGGGCCAGTGTGCT

GCAAATTGGCAGGAGACGTGAAGGCACCTCCAAAGTCGACTTTCTGGAGTTTCAAAAACAGACC

GTACATGTCCGCGGTCGCGACGTACCTACCGGGTAGGGGAGGCGCTTTTCCCAAGGCAGTCTG

GAGCATGCGCTTTAGCAGCCCCGCTGGGCACTTGGCGCTACACAAGTGGCCTCTGGCCTCGCA

CACATTCCACATCCACCGGTAGGCGCCAACCGGCTCCGTTCTTTGGTGGCCCCTTCGCGCCACC

TTCTACTCCTCCCCTAGTCAGGAAGTTCCCCCCCGCCCCGCAGCTCGCGTCGTGCAGGACGTGA

CAAATGGAAGTAGCACGTCTCACTAGTCTCGTGCAGATGGACAGCACCGCTGAGCAATGGAAGC

GGGTAGGCCTTTGGGGCAGCGGCCAATAGCAGCTTTGCTCCTTCGCTTTCTGGGCTCAGAGGCT

GGGAAGGGGTGGGTCCGGGGGCGGGCTCAGGGGCGGGCTCAGGGGCGGGGCGGGCGCCCG

AAGTCCTCCGGAGGCCCGGCATTCTGCACGCTTCAAAAGCGCACGTCTGCCGCGCTGTTCTCCT

CTTCCTCATCTCCGGGCCTTTCGACTCTAGACACGTGTTGACAATTAATCATCGGCATAGTATATC

GGCATAGTATAATACGAGAAGGTGAGGAACTAAACCATGGCCAAGCCTTTGTCTCAAGAAGAATC

CACCCTCATTGAAAGAGCAACGGCTACAATCAACAGCATCCCCATCTCTGAAGACTACAGCGTCG

CCAGCGCAGCTCTCTCTAGCGACGGCCGCATCTTCACTGGTGTCAATGTATATCATTTTACTGGG

GGACCTTGTGCAGAACTCGTGGTGCTGGGCACTGCTGCTGCTGCGGCAGCTGGCAACCTGACTT

GTATCGTCGCGATCGGAAATGAGAACAGGGGCATCTTGAGCCCCTGCGGACGGTGCCGACAGG

TGCTTCTCGATCTGCATCCTGGGATCAAAGCCATAGTGAAGGACAGTGATGGACAGCCGACGGC

AGTTGGGATTCGTGAATTGCTGCCCTCTGGTTATGTGTGGGAGGGCTAAGCACAATTCGAGCTC

GGTACGCGTATCGATGGCGCCAGCTGCAGGCGGCCGCCATATGCATCCTAGGCCTATTAATATT

CCGGAGTATACGTAGGCGGCTAACGTTAACAACCGGTACGATGCATTAGTTATTAATAGTAATCAA

TTACGGGGTCATTAGTTCATAGCCCATATATGGAGTTCCGCGTTACATAACTTACGGTAAATGGCC

CGCCTGGCTGACCGCCCAACGACCCCCGCCCATTGACGTCAATAATGACGTATGTTCCCATAGT

AACGCCAATAGGGACTTTCCATTGACGTCAATGGGTGGAGTATTTACGGTAAACTGCCCACTTGG

CAGTACATCAAGTGTATCATATGCCAAGTACGCCCCCTATTGACGTCAATGACGGTAAATGGCCC

GCCTGGCATTATGCCCAGTACATGACCTTATGGGACTTTCCTACTTGGCAGTACATCTACGTATTA

GTCATCGCTATTACCATGGTGATGCGGTTTTGGCAGTACATCAATGGGCGTGGATAGCGGTTTGA

CTCACGGGGATTTCCAAGTCTCCACCCCATTGACGTCAATGGGAGTTTGTTTTGGCACCAAAATC

AACGGGACTTTCCAAAATGTCGTAACAACTCCGCCCCATTGACGCAAATGGGCGGTAGGCGTGT

ACGGTGGGAGGTCTATATAAGCAGAGCTGGTTTAGTGAACCGTCAGATCCGCTAGCCCCACCAT

GCCGCGCGCTCCCCGCTGCCGAGCCGTGCGCTCCCTGCTGCGCAGCCACTACCGCGAGGTGCT

GCCGCTGGCCACGTTCGTGCGGCGCCTGGGGCCCCAGGGCTGGCGGCTGGTGCAGCGCGGG
```

-continued

```
GACCCGGCGGCTTTCCGCGCGCTGGTGGCCCAGTGCCTGGTGTGCGTGCCCTGGGACGCACG

GCCGCCCCCGCCGCCCCCTCCTTCCGCCAGGTGTCCTGCCTGAAGGAGCTGGTGGCCCGAGT

GCTGCAGAGGCTGTGCGAGCGCGGCGCGAAGAACGTGCTGGCCTTCGGCTTCGCGCTGCTGGA

CGGGGCCCGCGGGGGCCCCCCCGAGGCCTTCACCACCAGCGTGCGCAGCTACCTGCCCAACA

CGGTGACCGACGCACTGCGGGGGAGCGGGGCGTGGGGGCTGCTGTTGCGCCGCGTGGGCGA

CGACGTGCTGGTTCACCTGCTGGCACGCTGCGCGCTCTTTGTGCTGGTGGCTCCCAGCTGCGC

CTACCAGGTGTGCGGGCCGCCGCTGTACCAGCTCGGCGCTGCCACTCAGGCCCGGCCCCCGC

CACACGCTAGTGGACCCCGAAGGCGTCTGGGATGCGAACGGGCCTGGAACCATAGCGTCAGGG

AGGCCGGGGTCCCCCTGGGCCTGCCAGCCCCGGGTGCGAGGAGGCGCGGGGGCAGTGCCAG

CCGAAGTCTGCCGTTGCCCAAGAGGCCCAGGCGTGGCGCTGCCCCTGAGGCGGAGCGGACGC

CCGTTGGGCAGGGGTCCTGGGCCCACCCGGGCAGGACGCGTGGACCGAGTGACCGTGGTTTCT

GTGTGGTGTCACCTGCCAGACCCGCCGAAGAAGCCACCTCTTTGGAGGGTGCGCTCTCTGGCAC

GCGCCACTCCCACCCATCCGTGGGCCGCCAGCACCACGCGGGCCCCCCATCCACATCGCGGCC

ACCACGTCCCTGGGACACGCCTTGTCCCCCGGTGTACGCCGAGACCAAGCACTTCCTCTACTCC

TCAGGCGACAAGGAGCAGCTGCGGCCCTCCTTCCTACTCAGCTCTCTGAGGCCCAGCCTGACTG

GCGCTCGGAGGCTCGTGGAGACCATCTTTCTGGGTTCCAGGCCCTGGATGCCAGGGACTCCCC

GCAGGTTGCCCCGCCTGCCCCAGCGCTACTGGCAAATGCGGCCCCTGTTTCTGGAGCTGCTTG

GGAACCACGCGCAGTGCCCCTACGGGGTGCTCCTCAAGACGCACTGCCCGCTGCGAGCTGCGG

TCACCCCAGCAGCCGGTGTCTGTGCCCGGGAGAAGCCCCAGGGCTCTGTGGCGGCCCCCGAG

GAGGAGGACACAGACCCCCGTCGCCTGGTGCAGCTGCTCCGCCAGCACAGCAGCCCCTGGCAG

GTGTACGGCTTCGTGCGGGCCTGCCTGCGCCGGCTGGTGCCCCCAGGCCTCTGGGGCTCCAG

GCACAACGAACGCCGCTTCCTCAGGAACACCAAGAAGTTCATCTCCCTGGGGAAGCATGCCAAG

CTCTCGCTGCAGGAGCTGACGTGGAAGATGAGCGTGCGGGGCTGCGCTTGGCTGCGCAGGAGC

CCAGGGGTTGGCTGTGTTCCGGCCGCAGAGCACCGTCTGCGTGAGGAGATCCTGGCCAAGTTC

CTGCACTGGCTGATGAGTGTGTACGTCGTCGAGCTGCTCAGGTCTTTCTTTTATGTCACGGAGAC

CACGTTTCAAAAGAACAGGCTCTTTTTCTACCGGAAGAGTGTCTGGAGCAAGTTGCAAAGCATTG

GAATCAGACAGCACTTGAAGAGGGTGCAGCTGCGGGAGCTGTCGGAAGCAGAGGTCAGGCAGC

ATCGGGAAGCCAGGCCCGCCCTGCTGACGTCCAGACTCCGCTTCATCCCCAAGCCTGACGGGC

TGCGGCCGATTGTGAACATGGACTACGTCGTGGGAGCCAGAACGTTCCGCAGAGAAAAGAGGG

CCGAGCGTCTCACCTCCAGGGTGAAGGCACTGTTCAGCGTGCTCAACTACGAGCGGGCGCGGC

GCCCCGGCCTCCTGGGCGCCTCTGTGCTGGGCCTGGACGATATCCACAGGGCCTGGCGCACCT

TCGTGCTGCGTGTGCGGGCCCAGGACCCGCCGCCTGAGCTGTACTTTGTCAAGGTGGATGTGA

CGGGCGCGTACGACACCATCCCCCAGGACAGGCTCACGGAGGTCATCGCCAGCATCATCAAAC

CCCAGAACACGTACTGCGTGCGTCGGTATGCCGTGGTCCAGAAGGCCGCCCATGGGCACGTCC

GCAAGGCCTTCAAGAGCACGTCTCTACCTTGACAGACCTCCAGCCGTACATGCGACAGTTCGT

GGCTCACCTGCAGGAGACCAGCCCGCTGAGGGATGCCGTCGTCATCGAGCAGAGCTCCTCCCT

GAATGAGGCCAGCAGTGGCCTCTTCGACGTCTTCCTACGCTTCATGTGCCACCACGCCGTGCGC

ATCAGGGGCAAGTCCTACGTCCAGTGCCAGGGGATCCCGCAGGGCTCCATCCTCTCCACGCTG

CTCTGCAGCCTGTGCTACGGCGACATGGAGAACAAGCTGTTTGCGGGGATTCGGCGGGACGGG

CTGCTCCTGCGTTTGGTGGATGATTTCTTGTTGGTGACACCTCACCTCACCCACGCGAAAACCTT
```

-continued

```
CCTCAGGACCCTGGTCCGAGGTGTCCCTGAGTATGGCTGCGTGGTGAACTTGCGGAAGACAGTG

GTGAACTTCCCTGTAGAAGACGAGGCCCTGGGTGGCACGGCTTTTGTTCAGATGCCGGCCCACG

GCCTATTCCCCTGGTGCGGCCTGCTGCTGGATACCCGGACCCTGGAGGTGCAGAGCGACTACT

CCAGCTATGCCCGGACCTCCATCAGAGCCAGTCTCACCTTCAACCGCGGCTTCAAGGCTGGGAG

GAACATGCGTCGCAAACTCTTTGGGGTCTTGCGGCTGAAGTGTCACAGCCTGTTTCTGGATTTGC

AGGTGAACAGCCTCCAGACGGTGTGCACCAACATCTACAAGATCCTCCTGCTGCAGGCGTACAG

GTTTCACGCATGTGTGCTGCAGCTCCCATTTCATCAGCAAGTTTGGAAGAACCCCACATTTTTCCT

GCGCGTCATCTCTGACACGGCCTCCCTCTGCTACTCCATCCTGAAAGCCAAGAACGCAGGGATG

TCGCTGGGGGCCAAGGGCGCCGCCGGCCCTCTGCCCTCCGAGGCCGTGCAGTGGCTGTGCCA

CCAAGCATTCCTGCTCAAGCTGACTCGACACCGTGTCACCTACGTGCCACTCCTGGGGTCACTC

AGGACAGCCCAGACGCAGCTGAGTCGGAAGCTCCCGGGGACGACGCTGACTGCCCTGGAGGC

CGCAGCCAACCCGGCACTGCCCTCAGACTTCAAGACCATCCTGGACTGAGTCGAAACTCGCGGC

CGCATGCGTCGACGCGTATCGATGCATCTTAAGTAGATGTACCTTTAAGACCAATGACTTACAAG

GCAGCTGTAGATCTTAGCCACTTTTTAAAAGAAAAGGGGGACTGGAAGGGCTAATTCACTCCCA

ACGAAGACAAGATCTGCTTTTTGCTTGTACTGGGTCTCTCTGGTTAGACCAGATCTGAGCCTGGG

AGCTCTCTGGCTAACTAGGGAACCCACTGCTTAAGCCTCAATAAAGCTTGCCTTGAGTGCTTCAA

GTAGTGTGTGCCCGTCTGTTGTGTGACTCTGGTAACTAGAGATCCCTCAGACCCTTTTAGTCAGT

GTGGAAAATCTCTAGCAGTAGTAGTTCATGTCATCTTATTATTCAGTATTTATAACTTGCAAAGAAA

TGAATATCAGAGAGTGAGAGGAACTTGTTTATTGCAGCTTATAATGGTTACAAATAAAGCAATAGC

ATCACAAATTTCACAAATAAAGCATTTTTTTCACTGCATTCTAGTTGTGGTTTGTCCAAACTCATCA

ATGTATCTTATCATGTCTGGCTCTAGCTATCCCGCCCCTAACTCCGCCCATCCCGCCCCTAACTC

CGCCCAGTTCCGCCCATTCTCCGCCCCATGGCTGACTAATTTTTTTATTTATGCAGAGGCCGAG

GCCGCCTCGGCCTCTGAGCTATTCCAGAAGTAGTGAGGAGGCTTTTTTGGAGGCCTAGGGACGT

ACCCAATTCGCCCTATAGTGAGTCGTATTACGCGCGCTCACTGGCCGTCGTTTTACAACGTCGTG

ACTGGGAAAACCCTGGCGTTACCCAACTTAATCGCCTTGCAGCACATCCCCCTTTCGCCAGCTGG

CGTAATAGCGAAGAGGCCCGCACCGATCGCCCTTCCCAACAGTTGCGCAGCCTGAATGGCGAAT

GGGACGCGCCCTGTAGCGGCGCATTAAGCGCGGCGGGTGTGGTGGTTACGCGCAGCGTGACC

GCTACACTTGCCAGCGCCCTAGCGCCCGCTCCTTTCGCTTTCTTCCCTTCCTTTCTCGCCACGTT

CGCCGGCTTTCCCCGTCAAGCTCTAAATCGGGGGCTCCCTTTAGGGTTCCGATTTAGTGCTTTAC

GGCACCTCGACCCCAAAAAACTTGATTAGGGTGATGGTTCACGTAGTGGGCCATCGCCCTGATA

GACGGTTTTTCGCCCTTTGACGTTGGAGTCCACGTTCTTTAATAGTGGACTCTTGTTCCAAACTGG

AACAACACTCAACCCTATCTCGGTCTATTCTTTTGATTTATAAGGGATTTTGCCGATTTCGGCCTAT

TGGTTAAAAAATGAGCTGATTTAACAAAAATTTAACGCGAATTTTAACAAAATATTAACGCTTACAA

TTTAGGTGGCACTTTTCGGGGAAATGTGCGCGGAACCCCTATTTGTTTATTTTTCTAAATACATTC

AAATATGTATCCGCTCATGAGACAATAACCCTGATAAATGCTTCAATAATATTGAAAAGGAAGAG

TATGAGTATTCAACATTTCCGTGTCGCCCTTATTCCCTTTTTTGCGGCATTTTGCCTTCCTGTTTTT

GCTCACCCAGAAACGCTGGTGAAAGTAAAAGATGCTGAAGATCAGTTGGGTGCACGAGTGGGTT

ACATCGAACTGGATCTCAACAGCGGTAAGATCCTTGAGAGTTTTCGCCCCGAAGAACGTTTTCCA
```

-continued

```
ATGATGAGCACTTTTAAAGTTCTGCTATGTGGCGCGGTATTATCCCGTATTGACGCCGGCAAGA
GCAACTCGGTCGCCGCATACACTATTCTCAGAATGACTTGGTTGAGTACTCACCAGTCACAGAAA
AGCATCTTACGGATGGCATGACAGTAAGAGAATTATGCAGTGCTGCCATAACCATGAGTGATAAC
ACTGCGGCCAACTTACTTCTGACAACGATCGGAGGACCGAAGGAGCTAACCGCTTTTTTGCACAA
CATGGGGGATCATGTAACTCGCCTTGATCGTTGGGAACCGGAGCTGAATGAAGCCATACCAAAC
GACGAGCGTGACACCACGATGCCTGTAGCAATGGCAACAACGTTGCGCAAACTATTAACTGGCG
AACTACTTACTCTAGCTTCCCGGCAACAATTAATAGACTGGATGGAGGCGGATAAAGTTGCAGGA
CCACTTCTGCGCTCGGCCCTTCCGGCTGGCTGGTTTATTGCTGATAAATCTGGAGCCGGTGAGC
GTGGGTCTCGCGGTATCATTGCAGCACTGGGGCCAGATGGTAAGCCCTCCCGTATCGTAGTTAT
CTACACGACGGGGAGTCAGGCAACTATGGATGAACGAAATAGACAGATCGCTGAGATAGGTGCC
TCACTGATTAAGCATTGGTAACTGTCAGACCAAGTTTACTCATATATACTTTAGATTGATTTAAAAC
TTCATTTTTAATTTAAAAGGATCTAGGTGAAGATCCTTTTTGATAATCTCATGACCAAAATCCCTTA
ACGTGAGTTTTCGTTCCACTGAGCGTCAGACCCCGTAGAAAAGATCAAAGGATCTTCTTGAGATC
CTTTTTTTCTGCGCGTAATCTGCTGCTTGCAAACAAAAAAACCACCGCTACCAGCGGTGGTTTGTT
TGCCGGATCAAGAGCTACCAACTCTTTTTCCGAAGGTAACTGGCTTCAGCAGAGCGCAGATACCA
AATACTGTTCTTCTAGTGTAGCCGTAGTTAGGCCACCACTTCAAGAACTCTGTAGCACCGCCTAC
ATACCTCGCTCTGCTAATCCTGTTACCAGTGGCTGCTGCCAGTGGCGATAAGTCGTGTCTTACCG
GGTTGGACTCAAGACGATAGTTACCGGATAAGGCGCAGCGGTCGGGCTGAACGGGGGGTTCGT
GCACACAGCCCAGCTTGGAGCGAACGACCTACACCGAACTGAGATACCTACAGCGTGAGCTATG
AGAAAGCGCCACGCTTCCCGAAGGGAGAAAGGCGGACAGGTATCCGGTAAGCGGCAGGGTCGG
AACAGGAGAGCGCACGAGGGAGCTTCCAGGGGGAAACGCCTGGTATCTTTATAGTCCTGTCGGG
TTTCGCCACCTCTGACTTGAGCGTCGATTTTTGTGATGCTCGTCAGGGGGCGGAGCCTATGGA
AAAACGCCAGCAACGCGGCCTTTTTACGGTTCCTGGCCTTTTGCTGGCCTTTTGCTCACATGTTC
TTTCCTGCGTTATCCCCTGATTCTGTGGATAACCGTATTACCGCCTTTGAGTGAGCTGATACCGCT
CGCCGCAGCCGAACGACCGAGCGCAGCGAGTCAGTGAGCGAGGAAGCGGAAGAGCGCCCAAT
ACGCAAACCGCCTCTCCCCGCGCGTTGGCCGATTCATTAATGCAGCTGGCACGACAGGTTTCCC
GACTGGAAAGCGGGCAGTGAGCGCAACGCAATTAATGTGAGTTAGCTCACTCATTAGGCACCCC
AGGCTTTACACTTTATGCTTCCGGCTCGTATGTTGTGTGGAATTGTGAGCGGATAACAATTTCACA
CAGGAAACAGCTATGACCATGATTACGCCAAGCGCGCAATTAACCCTCACTAAAGGGAACAAAAG
CTGGAGCTGCAAGCTT
```

Although the foregoing invention has been described in some detail by way of illustration and example for purposes of clarity of understanding, it is readily apparent to those of ordinary skill in the art in light of the teachings of this invention that certain changes and modifications may be made thereto without departing from the spirit or scope of the appended claims.

Accordingly, the preceding merely illustrates the principles of the invention. It will be appreciated that those skilled in the art will be able to devise various arrangements which, although not explicitly described or shown herein, embody the principles of the invention and are included within its spirit and scope. Furthermore, all examples and conditional language recited herein are principally intended to aid the reader in understanding the principles of the invention and the concepts contributed by the inventors to furthering the art, and are to be construed as being without limitation to such specifically recited examples and conditions. Moreover, all statements herein reciting principles, aspects, and embodiments of the invention as well as specific examples thereof, are intended to encompass both structural and functional equivalents thereof. Additionally, it is intended that such equivalents include both currently known equivalents and equivalents developed in the future, i.e., any elements developed that perform the same function, regardless of structure. The scope of the present invention, therefore, is not intended to be limited to the exemplary embodiments shown and described herein. Rather, the scope and spirit of present invention is embodied by the appended claims.

What is claimed is:

1. A lentiviral vector comprising a coding sequence for functional telomerase reverse transcriptase (TERT) operably linked to a regulatory sequence comprising the cytomegalovirus (CMV) promoter that is capable of driving expression of the coding sequence, wherein the coding sequence is for human TERT and the vector expresses functional human TERT when present in a human cell.

2. The vector of claim 1, wherein the vector further comprises a coding sequence for telomerase RNA (TR).

3. An adeno-associated virus-based vector comprising a coding sequence for functional telomerase reverse transcriptase (TERT) that is operably linked to a cytomegalovirus (CMV) promoter regulatory sequence capable of driving expression of the coding sequence, wherein the coding sequence is for human TERT and the vector expresses functional human TERT when present in a human cell,
and wherein the vector is represented by the formula:
left inverted terminal repeat (LITR)-cytomegalovirus promoter (CMV)-telomerase reverse transcriptase coding sequence (TERT)-SV40 poly-adenylation signal (SV40pA)-right inverted terminal repeat (RITR),
wherein the TERT coding sequence is for human TERT, or a fragment of human TERT that retains TERT activity.

4. A nucleic acid viral vector comprising a coding sequence for functional telomerase reverse transcriptase (TERT) and a coding sequence for telomerase RNA (TR), wherein the vector expresses functional TERT when present in a human cell.

5. The vector of claim 4, wherein the nucleic acid sequence encoding TERT is operably linked to a regulatory sequence comprising the cytomegalovirus (CMV) promoter that is capable of driving expression of the coding sequences.

6. The vector of claim 4, wherein the vector is a non-integrative vector.

7. The vector of claim 6, wherein the vector is an adeno-associated virus-based vector.

8. The vector of claim 4, wherein the vector is a lentivirus-based vector.

9. The vector of claim 4, wherein the vector is represented by the formula:
long terminal repeat (LTR)-U1 promoter (U1)-telomerase RNA coding sequence (TR)-PGK promoter (PGK)-cytomegalovirus promoter (CMV)-telomerase reverse transcriptase coding sequence (TERT)-long terminal repeat (LTR),
wherein the TERT coding sequence is for human TERT, or a fragment of human TERT that retains TERT activity.

10. The vector of claim 7, wherein the vector is represented by the formula:
left inverted terminal repeat (LITR)-U1 promoter (U1)-telomerase RNA coding sequence (TR)-cytomegalovirus promoter (CMV)-telomerase reverse transcriptase coding sequence (TERT)-SV40 poly-adenylation signal (SV40pA)-right inverted terminal repeat (RITR),
wherein the TERT coding sequence is for human TERT, or a fragment of human TERT that retains TERT activity.

11. The vector of claim 10, wherein the vector is an AAV6 vector.

12. The vector of claim 10, wherein the vector is an AAV8 vector.

13. The vector of claim 10, wherein the vector is an AAV9 vector.

14. The vector of claim 1, wherein the vector is represented by the formula:
long terminal repeat (LTR)-cytomegalovirus promoter (CMV)-telomerase reverse transcriptase coding sequence (TERT)-long terminal repeat (LTR),
wherein the TERT coding sequence is for human TERT, or a fragment of human TERT that retains TERT activity.

* * * * *